US011618772B2

(12) United States Patent
Posakony

(10) Patent No.: US 11,618,772 B2
(45) Date of Patent: *Apr. 4, 2023

(54) MODIFICATIONS AND USES OF CONOTOXIN PEPTIDES

(71) Applicant: Kineta Chronic Pain, LLC, Seattle, WA (US)

(72) Inventor: Jeffrey Jerard Posakony, Seattle, WA (US)

(73) Assignee: Kineta Chronic Pain, LLC

( * ) Notice: Subject to any disclaimer, the term of this patent is extended or adjusted under 35 U.S.C. 154(b) by 117 days.

This patent is subject to a terminal disclaimer.

(21) Appl. No.: 17/037,521

(22) Filed: Sep. 29, 2020

(65) Prior Publication Data

US 2021/0122792 A1 Apr. 29, 2021

Related U.S. Application Data

(63) Continuation of application No. 15/525,024, filed as application No. PCT/US2015/059613 on Nov. 6, 2015, now Pat. No. 11,014,970.

(60) Provisional application No. 62/123,123, filed on Nov. 7, 2014.

(51) Int. Cl.
*C07K 14/435* (2006.01)
*A61K 47/54* (2017.01)
*A61K 47/60* (2017.01)
*A61P 29/00* (2006.01)
*A61K 38/00* (2006.01)

(52) U.S. Cl.
CPC ...... *C07K 14/43504* (2013.01); *A61K 47/542* (2017.08); *A61K 47/60* (2017.08); *A61P 29/00* (2018.01); *C07K 14/43509* (2013.01); *A61K 38/00* (2013.01); *C07K 2319/30* (2013.01); *C07K 2319/60* (2013.01)

(58) Field of Classification Search
CPC ................. C07K 14/43504; C07K 14/43509
See application file for complete search history.

(56) References Cited

U.S. PATENT DOCUMENTS

| | | |
|---|---|---|
| 2010/0022749 A1 | 1/2010 | Robinson et al. |
| 2011/0045587 A1 | 2/2011 | Sullivan et al. |
| 2011/0195909 A1 | 8/2011 | Lewis et al. |
| 2012/0149869 A1 | 6/2012 | Watkins et al. |
| 2012/0190827 A1 | 7/2012 | Sheffer et al. |
| 2012/0220539 A1 | 8/2012 | McIntosh et al. |
| 2014/0323701 A1 | 10/2014 | Nash et al. |
| 2018/0362599 A1 | 12/2018 | Posakony et al. |
| 2020/0237924 A1 | 7/2020 | Mercado et al. |

FOREIGN PATENT DOCUMENTS

| | | |
|---|---|---|
| CN | 1379786 A | 11/2002 |
| EP | 1834962 A1 | 9/2007 |
| WO | WO 1996040211 A1 | 12/1996 |
| WO | WO-2014194284 A1 * | 12/2014 ............. A61K 38/00 |
| WO | WO 2014194284 A1 | 12/2014 |

OTHER PUBLICATIONS

Empting et al., "Triazole Bridge": Disulfide-Bond Replacement by Ruthenium-Catalyzed Formation of 1,5-Disubstituted 1,2,3-Triazoles, Angew. Chem. Int. Ed. 2011, 50, 5207-5211 (Year: 2011).*
Gori et al., Stabilization of the Cysteine-Rich Conotoxin MrIA by Using a 1,2,3-Triazole as a Disulfide Bond Mimetic, Angew. Chem. Int. Ed. 2015, 54, 1361-1364 (Year: 2015).*
U.S. Appl. No. 61/843,135, filed Jul. 5, 2013, J. M. McIntosh.
Armishaw et al., 2006, "Alpha-selenoconotoxins, a new class of potent alpha7 neuronal nicotinic receptor antagonists," J Biol Chem., 281(20):14136-14143.
Armishaw, 2010, "Synthetic α-Conotoxin Mutants as Probes for Studying Nicotinic Acetylcholine Receptors and in the Development of Novel Drug Leads," Toxins, 2(6):1471-1499.
Brady et al., 2013, "Strategies for the Development of Conotoxin as New Therapeutic Leads," Marine Drugs, 11(7):2293-2313.
Bulaj et al., 2008, "Folding of Conotoxins: Formation of the Native Disulfide Bridges During Chemical Synthesis and Biosynthesis of Conus Peptides," Antioxid. Redox Signaling, 10(1):141-156.
Castellano et al., 2009, "Low Exchangeability of Selenocysteine, the 21st Amino Acid, in Vertebrate Proteins," Mol. Biol. Evol., 26(9):2031-2040.
Chang et al., 2005, "Conformational impurity of disulfide proteins: detection, quantification, and properties," Anal. Biochem., 342(1):78-85.
Chhabra et al., 2014, "Dicarba analogues of α-conotoxin RgIA. Structure, stability, and activity at potential pain targets," J Med Chem., 57(23):9933-9944.
Chhabra et al., 2014, Supporting Information for "Dicarba Analogues of α-Conotoxin RgIA. Structure, Stability and Activity at Potential Pain Targets," J. Med. Chem., 57(23):9933-9944, pp. 1-15.
Dekan et al., 2011, "α-Conotoxin ImI incorporating stable cystathionine bridges maintains full potency and identical three-dimensional structure," J Am Chem Soc., 133(40):15866-15869.
Ellison et al., 2006, "α-RgIA: A Novel Conotoxin That Specifically and Potently Blocks the α9α10 nAChR," Biochemistiy, 45(5):1511-1517.

(Continued)

Primary Examiner — Lianko G Garyu
(74) Attorney, Agent, or Firm — McCarter & English, LLP; Marcie B. Clarke

(57) ABSTRACT

The present disclosure describes analog conotoxin peptides of the α-conotoxin peptide RgIA. These analog conotoxin peptides block the α9α10 subtype of the nicotinic acetylcholine receptor (nAChR) and can be used for treating pain and inflammation including inflammatory pain, cancer related pain, and neuropathic pain. The RgIA analogs described in the present invention include a variety of sequence modifications and chemical modifications that are introduced to improve the drug-like characteristics of RgIA analogs and thereby increase their therapeutic value.

20 Claims, 10 Drawing Sheets

Specification includes a Sequence Listing.

(56) References Cited

OTHER PUBLICATIONS

Ellison et al., 2008, "α-RgIA, a Novel Conotoxin that Blocks the α9α10 nAChR: Structure and Identification of Key Receptor Binding Residues," J. Mol. Biol., 377(4):1216-1227.
Empting et al., 2011, "Triazole Bridge: Disulfide-Bond Replacement by Ruthenium-Catalyzed Formation of 1,5-Disubstituted 1,2,3-Triazoles," Angew. Chem. Int. Ed., 50(22):5207-5211.
Góngora-Benítez et al., 2014, "Multifaceted Roles of Disulfide Bonds. Peptides as Therapeutics," Chem. Rev., 114(2):901-926.
Gori et al., 2015, "Stabilization of the cysteine-rich conotoxin MrIA by using a 1,2,3-triazole as a disulfide bond mimetic," Angew Chem Int Ed Engl., 54(4):1361-1364 (Epub 2014).
Green et al., 2007, "Conotoxins Containing non-natural Backbone Spacers: Cladistic-Based Design, Chemical Synthesis, and Improved Analgesic Activity," Chemistry and Biology, Current Biology, 14(4):399-407.
Hargittai et al., 2000, "Chemical syntheses and biological activities of lactam analogues of alpha-conotoxin SI," J Med Chem., 43(25):4787-4792.
Harris et al., 2003, "Effect of pegylation on pharmaceuticals," Nat Rev Drug Discov., 2(3):214-221.
Holland-Nell et al., 2011, "Maintaining biological activity by using triazoles as disulfide bond mimetics," Angew Chem Int Ed Engl., 50(22):5204-5206.
International Preliminary Report on Patentability (Chapter I) issued in International Patent Application No. PCT/US2015/059613 (Pub No. WO 2016073949) dated May 9, 2017 (10 pages).
International Search Report and Written Opinion issued in International Patent Application No. PCT/US2015/059613 (Pub No. WO 2016073949) dated Feb. 19, 2016 (12 pages).
Lodotyrosine, from http://www.hmdb.ca/metabolites/HMDB0000021, pp. 1-9, accessed Jul. 15, 2019.
Jin et al. (eds.), 2009, Pharmaceutical Knowledge (II), Military Medical Science Press, p. 212.
Kompella et al., 2013, "Dicarba modification of α-conotoxin RgIA conferring selectivity towards α9α1l0 nicotinic acetylcholine receptors," Biochemical Pharmacology, 86(8):1230.
Kowalczyk et al., 2012, "Synthesis and evaluation of disulfide bond mimetics of amylin-(1-8) as agents to treat osteoporosis" Bioorg Med Chem., 20(8):2661-2668.
Li et al., 2013, "Click Chemistry in Peptide-Based Drug Design," Molecules, 18(8):9797-9817.
Liskamp et al., 2011, "Peptides and Proteins as a Continuing Exciting Source of Inspiration for Peptidomimetics," ChemBiochem, 12(11):1626-1653.
Luo et al., 2013, "Characterization of a Novel Alpha-Conotoxin TxID from Conus textile that Potently Blocks rat Alpha3beta4 Nicotinic Acetylcholine Receptors," Journal of Medicinal Chemistry, 56(23):9655-9663.
Macraild et al., 2009, "Structure and activity of (2, 8)-dicarba-(3, 12)-cystino α-ImI, an α-conotoxin containing a nonreducible cystine analogue," J. Med. Chem., 52(3):755-762.
Mcintosh et al., 2009, "Alpha9 nicotinic acetylcholine receptors and the treatment of pain," Biochem Pharmacol, 78(7):693-702.
Partial Supplementary European Search Report issued in European Patent Application No. 15856496.3 dated Mar. 9, 2018 (18 pages).
Qian et al., 2002, "Characterization of a site-specific PEGylated analog of exendin-4 and determination of the PEGylation site," International Journal of Pharmaceutics, 454(1):553-558.
Romero et al., 2017, "Inhibition of a9a!0 nicotinic acetylcholine receptors prevents chemotherapy-induced neuropathic pain," Proc. Natl. Acad. Sci. USA, 114(10):E1825-E1832.
Schmidt et al., 2006, "Allosteric Disulfide Bonds," Biochemistiy, 45(24):7429-7433.
Supplementary European Search Report issued in European Patent Application No. 15856496.3 dated Jun. 22, 2018 (22 pages).
Tornøe et al., 2004, "Combinatorial Library of Peptidotriazoles: Identification of [1,2,3]-Triazole Inhibitors against a Recombinant Leishmania mexicana Cysteine Protease," J. Comb. Chem., 6(3):312-324.
Van Lierop et al., 2013, "Dicarba α-Conotoxin Vc1.1 Analogues with Differential Selectivity for Nicotinic Acetylcholine and GABAB Receptors," ACS Chemical Biology, 8(8): 1815-1821.
Veronese et al., 2005, "PEGylation, successful approach to drug delivery," Drug Discovery Today, 10(21):1451-1458.
Vincler et al., 2006, "Molecular mechanism for analgesia involving specific antagonism of alpha9alpha10 nicotinic acetylcholine receptors," Proc Natl Acad Sci USA, 103(47):17880-17884.
Ward et al., 2013, "Peptide lipidation stabilizes structure to enhance biological function," Mol Metab., 2(4):468-479.
Xu et al. (eds.), 1996, Medicinal Chemistry, China Medical Science and Technology Press, pp. 209-216.
Xue et al. (eds.), 2011, Application and Technology of Polyethylene glycol in Field of Medicine, Huazhong University of Science and Technology Press, pp. 82-93.
Yang et al., 1983, "Endemic selenium intoxication of humnas in China," The American Journal of Clinical Nutrition, 37(5):872-881.
Email dated Feb. 4, 2020 from A. Antler to S. Marty, 1 page.
Attachment to email dated Feb. 4, 2020 from A. Antler to S. Marty: email dated Sep. 24, 2015 from J. Posakony to R. Jawando, 1 page.
Letter dated Feb. 19, 2020 from S. Marty to A. Antler, 1 page.
Email dated Feb. 28, 2020 from A. Antler to S. Marty, 1 page.
Letter dated Apr. 9, 2020 from S. Marty to A. Antler, 4 pages.
Exhibits UURF0000001-UURF0000007 accompanying S. Marty's letter of Apr. 9, 2020, analysis report dated Nov. 20, 2014, 7 pages.
Exhibits UURF0000008-UURF0000016 accompanying S. Marty's letter of Apr. 9, 2020, analysis report dated Nov. 21, 2014, 7 pages.
Exhibits UURF0000017-UURF0000072 accompanying S. Marty's letter of Apr. 9, 2020, analyses results dated from Dec. 23, 2014 to Dec. 26, 2014, 56 pages.
Exhibits UURF0000073-UURF0000091 accompanying S. Marty's letter of Apr. 9, 2020, analyses results dated from Jan. 13, 2015 to Jan. 20, 2015, 19 pages.
Exhibits UURF0000092-UURF0000099 accompanying S. Marty's letter of Apr. 9, 2020, analyses results dated from Jan. 23, 2015 to Feb. 6, 2015, 8 pages.
Exhibits UURF0000100-UURF0000102 accompanying S. Marty's letter of Apr. 9, 2020, analyses results dated from Feb. 3, 2015 to Feb. 17, 2015, 3 pages.
Exhibits UURF0000103-UURF0000107 accompanying S. Marty's letter of Apr. 9, 2020, analyses results dated from Feb. 24, 2015, 5 pages.
Exhibits UURF0000108-UURF0000119 accompanying S. Marty's letter of Apr. 9, 2020, analyses results dated from Feb. 17, 2015 to Mar. 12, 2015, 12 pages.
Exhibits UURF0000120-UURF0000152 accompanying S. Marty's letter of Apr. 9, 2020, analyses results dated from Apr. 16, 2015 to May 11, 2015, 33 pages.
Exhibits UURF0000153-UURF0000158 accompanying S. Marty's letter of Apr. 9, 2020, lab notebook pages dated from Nov. 19, 2014 to Jan. 26, 2015, 6 pages.
Exhibits UURF0000159-UURF0000160 accompanying S. Marty's letter of Apr. 9, 2020, email from Kineta to J. M. McIntosh dated May 2, 2013, 2 pages.
Exhibits UURF0000161-UURF0000164 accompanying S. Marty's letter of Apr. 9, 2020, emails between Kineta and J. M. McIntosh dated from Dec. 2, 2014 to Dec. 12, 2014, 4 pages.
Exhibits UURF0000165-UURF0000167 accompanying S. Marty's letter of Apr. 9, 2020, email trail including emails between Kineta and J. M. McIntosh dated from Oct. 20, 2014 to Nov. 7, 2014, 3 pages.
Exhibit UURF0000168 accompanying S. Marty's letter of Apr. 9, 2020, email from J. M. McIntosh to Kineta dated Nov. 20, 2014, 1 page.
Exhibits UURF0000169-UURF0000179 accompanying S. Marty's letter of Apr. 9, 2020, emails between Kineta and J. M. McIntosh dated from Jan. 22, 2014 to Jan. 30, 2014, 11 pages.
Exhibits UURF0000180-UURF0000181 accompanying S. Marty's letter of Apr. 9, 2020, 2 pages.

(56) References Cited

OTHER PUBLICATIONS

Exhibit UURF0000182 accompanying S. Marty's letter of Apr. 9, 2020, email from Kineta to J. M. McIntosh dated Aug. 6, 2013, 1 page.
Exhibit UURF0000183 accompanying S. Marty's letter of Apr. 9, 2020, emails between Kineta and S. Christensen (University of Utah) dated from Jul. 15, 2013, 1 page.
Exhibits UURF0000184-UURF0000188 accompanying S. Marty's letter of Apr. 9, 2020, analyses results dated Jul. 11, 2013, 5 pages.
Exhibit UURF0000189 accompanying S. Marty's letter of Apr. 9, 2020, analysis results dated Jul. 9, 2013, 1 page.
Exhibits UURF0000190-UURF0000201 accompanying S. Marty's letter of Apr. 9, 2020, emails between Kineta and J. M. McIntosh dated from May 10, 2013 to May 23, 2013, 12 pages.
Exhibits UURF0000202-UURF0000212 accompanying S. Marty's letter of Apr. 9, 2020, emails between Kineta and J. M. McIntosh dated from May 9, 2013 to May 22, 2013, 11 pages.
Exhibits UURF0000213-UURF0000222 accompanying S. Marty's letter of Apr. 9, 2020, emails between Kineta and J. M. McIntosh dated from May 9, 2013 to May 22, 2013, 10 pages.
Exhibits UURF0000223-UURF0000231 accompanying S. Marty's letter of Apr. 9, 2020, emails between Kineta and J. M. McIntosh and S. Christensen (University of Utah) dated from May 9, 2013 to May 21, 2013, 9 pages.
Exhibit UURF0000232 accompanying S. Marty's letter of Apr. 9, 2020, 1 page.
Exhibits UURF0000233-UURF0000238 accompanying S. Marty's letter of Apr. 9, 2020, emails between Kineta and J. M. McIntosh dated from May 9, 2013 to May 15, 2013, 6 pages.
Exhibits UURF0000239-UURF0000240 accompanying S. Marty's letter of Apr. 9, 2020, emails between Kineta and J. M. McIntosh dated from Jul. 18, 2014 to Jul. 21, 2014, 2 pages.
Exhibit UURF0000241 accompanying S. Marty's letter of Apr. 9, 2020, email from Kineta to J. M. McIntosh dated Aug. 5, 2013, 1 page.
Exhibit UURF0000242 accompanying S. Marty's letter of Apr. 9, 2020, email from S. Christensen (Univesrity of Utah) to J. M. McIntosh dated Feb. 21, 2020, 1 page.
Exhibit UURF0000243 accompanying S. Marty's letter of Apr. 9, 2020, emails between Kineta and J. M. McIntosh dated Jan. 29, 2015, including email from E. Munoz to J. M. McIntosh, 1 page.
Exhibit UURF0000244 accompanying S. Marty's letter of Apr. 9, 2020, email from Kineta to J. M. McIntosh dated Jan. 29, 2015, 1 page.
Exhibit UURF0000245 accompanying S. Marty's letter of Apr. 9, 2020, emails between S. Christensen (University of Utah) and J. M. McIntosh dated Dec. 3, 2015, 1 page.
Exhibits UURF0000246-UURF0000252 accompanying S. Marty's letter of Apr. 9, 2020, emails between Kineta and J. M. McIntosh dated from Febmary 27, 2015 to Mar. 2, 2015, including email from J. M. McIntosh to Kineta dated Feb. 27, 2015, 7 pages.
Exhibits UURF0000253-UURF0000254 accompanying S. Marty's letter of Apr. 9, 2020, emails between Kineta and J. M. McIntosh dated Feb. 27, 2015, including email from J. M. McIntosh to Kineta dated Feb. 27, 2015, 2 pages.
Exhibit UURF0000255 accompanying S. Marty's letter of Apr. 9, 2020, emails between Kineta and J. M. McIntosh dated Feb. 27, 2015, 1 page.
Exhibit UURF0000256 accompanying S. Marty's letter of Apr. 9, 2020, email email from Kineta to J. M. McIntosh dated Feb. 27, 2015, 1 page.
Exhibits UURF0000257-UURF0000260 accompanying S. Marty's letter of Apr. 9, 2020, emails between Kineta and J. M. McIntosh dated from Feb. 4, 2015 to Feb. 5, 2015, 4 pages.
Exhibits UURF0000261-UURF0000263 accompanying S. Marty's letter of Apr. 9, 2020, emails between Kineta and J. M. McIntosh dated from Jan. 30, 2015 to Feb. 5, 2015, 3 pages.
Exhibits UURF0000264-UURF0000265 accompanying S. Marty's letter of Apr. 9, 2020, emails between Kineta and J. M. McIntosh dated from Nov. 4, 2015 to Nov. 5, 2015, 2 pages.
Exhibit UURF0000266 accompanying S. Marty's letter of Apr. 9, 2020, email from Kineta to J. M. McIntosh dated Nov. 4, 2015, 1 page.
Exhibits UURF0000267-UURF0000274 accompanying S. Marty's letter of Apr. 9, 2020, email trail including emails between Kineta, J. M. McIntosh, and patent prosecution counsel dated from May 30 2013 to May 16, 2014, 2014, 8 pages (redacted).
Exhibits UURF0000275-UURF0000280 accompanying S. Marty's letter of Apr. 9, 2020, emails between Kineta and J. M. McIntosh dated Jul. 22, 2014, including email from Kineta to J. M. McIntosh dated Jul. 22, 2014, 6 pages.
Exhibits UURF0000281-UURF0000283 accompanying S. Marty's letter of Apr. 9, 2020, emails between Kineta and J. M. McIntosh dated from Aug. 13, 2014 to Aug. 14, 2015, 3 pages.
Exhibits UURF0000284-UURF0000290 accompanying S. Marty's letter of Apr. 9, 2020, email trail including emails between Kineta, J. M. McIntosh, and patent prosecution counsel dated from Jul. 1, 2013 to May 16, 2014, 7 pages (redacted).
Exhibits UURF0000291-UURF0000299 accompanying S. Marty's letter of Apr. 9, 2020, emails between Kineta and J. M. McIntosh dated from Mar. 22, 2014 to Apr. 24, 2014, 9 pages.
Exhibits UURF0000300-UURF0000301 accompanying S. Marty's letter of Apr. 9, 2020, emails between Kineta and J. M. McIntosh dated Feb. 24, 2015, 2 pages.
Exhibit UURF0000302 accompanying S. Marty's letter of Apr. 9, 2020, emails between Kineta and J. M. McIntosh dated from Feb. 23, 2015 to Feb. 24, 2015, including email from Kineta to J. M, McIntosh dated on Feb. 23, 1 page.
Kineta Pharmacokinetic Study Report CSP PK 01 for period from Mar. 25, 2014 to Mar. 26, 2014, 20 pages.
Emails between Kineta and R. Norton dated from Mar. 27, 2014 to Apr. 21, 2014, 7 pages.
Kineta BAS 05 Report for period from Jul. 2014 to Oct. 2014, 33 pages.
Kineta Monthly Conopeptide Program Update dated Jul. 24, 2014, 43 pages.
Kineta's in vivo pharmacology analyses results, dated Aug. 4, 2014, 4 pages.
Kineta BAS 07 Report for period from Sep. 30, 2014 to Sep. 31, 2014, 8 pages.
Kineta BAM Report for period from Sep. 2014 to Mar. 2015, 24 pages.
Email from J. Posakony to J. Bartron at Kineta dated Sep. 5, 2014, 1 page.
Analyses results including results dated Sep. 11, 2014 and Sep. 16, 2014, 15 pages.
Kineta Quarterly Conopeptide Program Update dated Jan. 26, 2015, 29 pages.
Minutes of Kineta Quarterly Conopeptide Meeting dated Jan. 26, 2015, 2 pages.
Kineta's analyses results dated Feb. 18, 2015 and internal emails dated Feb. 19, 2015, 33 pages.
Email trail including emails between Kineta and Peptides International dated from Mar. 10, 2015 to Mar. 13, 2015, 4 pages.
Minutes of Kineta Monthly Conopeptide Meeting dated Oct. 7, 2015, 2 pages.
Emails between Kineta and J. M. McIntosh dated Oct. 8, 2015, 1 page.
Kineta Study Protocol BAS 14 for period from Nov. 6, 2015 to Nov. 12, 2015, 5 pages.
Kineta BAS Report dated Feb. 2016, 17 pages.
Kineta Monthly Conopeptide Program Update slides dated Feb. 4, 2015 and analyses results dated Mar. 9, 2015, 28 pages.
Emails between Kineta and J. M. McIntosh dated Mar. 27, 2015, including email from J. M. McIntosh to Kineta dated Mar. 27, 2015, 5 pages.
Kineta Meeting Minutes dated Jul. 1, 2015, and quote from Peptides International dated Apr. 2, 2015, 6 pages.
Quote from Peptides International dated Oct. 7, 2015, 1 page.
Analytical data sheet by Peptides International, dated Nov. 25, 2015, 3 pages.
Kineta Certificate of Testing, dated Dec. 7, 2015, 3 pages.
Kineta BAS 15, including analyses results dated Nov. 25, 2015.

(56) References Cited

OTHER PUBLICATIONS

Shipping manifest for shipment from Kineta to J. M. McIntosh, dated Dec. 2, 2015.
Test results by J. M. McIntosh, dated Jan. 8, 2016, 12 pages.
Test results by Kineta, dated Mar. 3, 2016, 9 pages.
Email from Kineta to J. M. McIntosh dated May 2, 2013, 2 pages.
Kineta Conopeptide Program Meeting Slides dated Jun. 11, 2014.
Email from Kineta to J. M. McIntosh dated Jul. 18, 2014, 1 page.
Exclusive License Agreement between Kineta, Inc. and Unviersity of Utah Research Foundation, dated May 17, 2012, 27 pages (redacted).
First Amendment to Exclusive License Agreement between Kineta, Inc. and Unviersity of Utah Research Foundation dated Apr. 30, 2018, 6 pages.
Service Agreement between Kineta Three LLC and the University of Utah, dated Feb. 15, 2014, 9 pages (redacted).
Consulting Agreement between Kineta Chronic Pain, LLC and J. M. McIntosh, dated Feb. 20, 2017, 9 pages (redacted).
Termination Certificate of Consulting Agreement between Kineta Chronic Pain, LLC and J. M. McIntosh, dated Jun. 6, 2017, 1 page.
Email from Kineta to J. M. McIntosh dated Feb. 6, 2015, 1 page.
Minutes of Kineta's meeting with Peptides International, dated Aug. 14, 2015, 1 page.
Email trail including email from S. Christensen (University of Utah) to Kineta dated Aug. 27, 2015, 1 page.
Emails between Kineta and Peptides International dated from Sep. 11, 2015 to Sep. 14, 2015, 3 pages.
DOD Subcontract between Kineta, Inc. and the University of Utah, dated Sep. 30, 2015, 47 pages.
Email trail including emails between Kineta and J. M. McIntosh dated from May 12, 2014 to May 16, 2014, 8 pages.
Email trail including email from J. M. McIntosh to Kineta dated Nov. 20, 2014, 2 pages.
Kineta's research proposal to the U.S. Army, Mar. 2013, 50 pages.
Kineta's laboratory meeting slides, dated Aug. 6, 2014, 11 pages.
Letter dated Jun. 17, 2020 from A. Antler to S. Marty, 7 pages.
Exhibit 1 accompanying A. Antler's letter of Jun. 17, 2020, 1 page.
Exhibit 2 accompanying A. Antler's letter of Jun. 17, 2020, 1 page.
Exhibit 3 accompanying A. Antler's letter of Jun. 17, 2020, 5 pages.
Exhibit 4 accompanying A. Antler's letter of Jun. 17, 2020, 4 pages.
Exhibit 5 accompanying A. Antler's letter of Jun. 17, 2020, 1 page.

\* cited by examiner

SEQUENCE LISTING

```
<160> NUMBER OF SEQ ID NOS: 334

<210> SEQ ID NO 1
<211> LENGTH: 13
<212> TYPE: PRT
<213> ORGANISM: Conus regius

<400> SEQUENCE: 1

Gly Cys Cys Ser Asp Pro Arg Cys Arg Tyr Arg Cys Arg
1               5                   10

<210> SEQ ID NO 2
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
```

```
<223> OTHER INFORMATION: 3-iodo-Tyrosine

<400> SEQUENCE: 2

Gly Cys Cys Ser Asp Pro Arg Cys Arg Xaa Arg Cys Arg
1               5                   10

<210> SEQ ID NO 3
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 3

Gly Cys Cys Thr Asp Pro Arg Cys Xaa Xaa Gln Cys Arg
1               5                   10

<210> SEQ ID NO 4
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 4

Gly Cys Cys Thr Asp Pro Arg Cys Xaa Xaa Gln Cys Arg Arg Arg
1               5                   10                  15

<210> SEQ ID NO 5
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 5

Gly Cys Cys Thr Asp Pro Arg Cys Xaa Xaa Gln Cys Tyr
1               5                   10

<210> SEQ ID NO 6
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
```

```
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 6

Gly Xaa Cys Thr Asp Pro Arg Xaa Xaa Xaa Gln Cys Arg
1               5                   10

<210> SEQ ID NO 7
<211> LENGTH: 13
<212> TYPE: PRT
<213> ORGANISM: Artificial sequence
<220> FEATURE:
<223> OTHER INFORMATION: RgIA analog
<220> FE

```
<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: VARIANT
<222> LOCATION: (8)..(8)
<223> OTHER INFORMATION: des-Xaa, Cys, or selenocysteine
<220> FEATURE:
<221> NAME/KEY: VARIANT
<222> LOCATION: (9)..(9)
<223> OTHER INFORMATION: des-Xaa, Arg or citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: VARIANT
<222> LOCATION: (11)..(11)
<223> OTHER INFORMATION: des-Xaa, Arg, or Gln
<220> FEATURE:
<221> NAME/KEY: VARIANT
<222> LOCATION: (12)..(12)
<223> OTHER INFORMATION: des-Xaa, Cys, or selenocysteine
<220> FEATURE:
<221> NAME/KEY: VARIANT
<222> LOCATION: (13)..(13)
<223> OTHER INFORMATION: des-Xaa, Arg, Tyr, Phe, Trp, Tyr-Tyr, Tyr-Arg,
      Arg-Arg-Arg, Arg-Arg, Arg-Tyr, Arg-Arg-Tyr, or Tyr-Arg-Arg

<400> SEQUENCE: 10

Xaa Xaa Xaa Xaa Asp Pro Arg Xaa Xaa Xaa Xaa Xaa Xaa
1               5                   10

<210> SEQ ID NO 11
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (2)..(2)
<223> OTHER INFORMATION: Cys or selenocysteine
<220> FEATURE:
<221> NAME/KEY: VARIANT
<222> LOCATION: (4)..(4)
<223> OTHER INFORMATION: Ser or Thr
<220> FEATURE:
<221> NAME/KEY: VARIANT
<222> LOCATION: (8)..(8)
<223> OTHER INFORMATION: Cys or selenocysteine
<220> FEATURE:
<221> NAME/KEY: VARIANT
<222> LOCATION: (9)..(9)
<223> OTHER INFORMATION: Arg or citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: VARIANT
<222> LOCATION: (11)..(11)
<223> OTHER INFORMATION: Arg or Gln
<220> FEATURE:
<221> NAME/KEY: VARIANT
```

```
<222> LOCATION: (13)..(13)
<223> OTHER INFORMATION: Arg, Tyr, Phe, Trp, or  Arg-Arg-Arg

<400> SEQUENCE: 11

Gly Xaa Cys Xaa Asp Pro Arg Xaa Xaa Xaa Xaa Cys Xaa
1               5                   10

<210> SEQ ID NO 12
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (2)..(2)
<223> OTHER INFORMATION: Cys or selenocysteine
<220> FEATURE:
<221> NAME/KEY: VARIANT
<222> LOCATION: (8)..(8)
<223> OTHER INFORMATION: Cys or selenocysteine
<220> FEATURE:
<221> NAME/KEY: VARIANT
<222> LOCATION: (9)..(9)
<223> OTHER INFORMATION: Arg or citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: VARIANT
<222> LOCATION: (13)..(13)
<223> OTHER INFORMATION: Arg or Tyr

<400> SEQUENCE: 12

Gly Xaa Cys Thr Asp Pro Arg Xaa Xaa Xaa Gln Cys Xaa
1               5                   10

<210> SEQ ID NO 13
<211> LENGTH: 19
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MISC_FEATURE
<222> LOCATION: (19)..(1)
<223> OTHER INFORMATION: Cyclization

<400> SEQUENCE: 13

Gly Cys Cys Ser Asp Pro Arg Cys Arg Xaa Arg Cys Arg Gly Ala Ala
1               5                   10                  15

Gly Ala Gly

<210> SEQ ID NO 14
<211> LENGTH: 19
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
```

```
<220> FEATURE:
<221> NAME/KEY: MISC_FEATURE
<222> LOCATION: (19)..(1)
<223> OTHER INFORMATION: Cyclization

<400> SEQUENCE: 14

Gly Cys Cys Thr Asp Pro Arg Cys Xaa Xaa Gln Cys Arg Gly Ala Ala
1               5                   10                  15

Gly Ala Gly

<210> SEQ ID NO 15
<211> LENGTH: 21
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MISC_FEATURE
<222> LOCATION: (21)..(1)
<223> OTHER INFORMATION: Cyclization

<400> SEQUENCE: 15

Gly Cys Cys Thr Asp Pro Arg Cys Xaa Xaa Gln Cys Arg Arg Arg Gly
1               5                   10                  15

Ala Ala Gly Ala Gly
            20

<210> SEQ ID NO 16
<211> LENGTH: 19
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MISC_FEATURE
<222> LOCATION: (19)..(1)
<223> OTHER INFORMATION: Cyclization

<400> SEQUENCE: 16

Gly Cys Cys Thr Asp Pro Arg Cys Xaa Xaa Gln Cys Tyr Gly Ala Ala
1               5                   10                  15

Gly Ala Gly

<210> SEQ ID NO 17
<211> LENGTH: 19
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (2)..(2)
<223> OTHER INFORMATION: des-Xaa, Arg or Gln
<220> FEATURE:
```

```
<221> NAME/KEY: VARIANT
<222> LOCATION: (8)..(8)
<223> OTHER INFORMATION: des-Xaa, Arg or Gln
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MISC_FEATURE
<222> LOCATION: (19)..(1)
<223> OTHER INFORMATION: Cyclization

<400> SEQUENCE: 17

Gly Xaa Cys Thr Asp Pro Arg Xaa Xaa Xaa Gln Cys Arg Gly Ala Ala
1               5                   10                  15

Gly Ala Gly

<210> SEQ ID NO 18
<211> LENGTH: 19
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MISC_FEATURE
<222> LOCATION: (19)..(1)
<223> OTHER INFORMATION: Cyclization

<400> SEQUENCE: 18

Gly Cys Cys Thr Asp Pro Arg Cys Arg Xaa Gln Cys Phe Gly Ala Ala
1               5                   10                  15

Gly Ala Gly

<210> SEQ ID NO 19
<211> LENGTH: 19
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MISC_FEATURE
<222> LOCATION: (19)..(1)
<223> OTHER INFORMATION: Cyclization

<400> SEQUENCE: 19

Gly Cys Cys Thr Asp Pro Arg Cys Arg Xaa Gln Cys Tyr Gly Ala Ala
1               5                   10                  15

Gly Ala Gly

<210> SEQ ID NO 20
<211> LENGTH: 19
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (10)..(10)
```

```
<223> OTHER INFORMATION: des-Xaa, Ser, or Thr
<220> FEATURE:
<221> NAME/KEY: MISC_FEATURE
<222> LOCATION: (19)..(1)
<223> OTHER INFORMATION: Cyclization

<400> SEQUENCE: 20

Gly Cys Cys Thr Asp Pro Arg Cys Arg Xaa Gln Cys Trp Gly Ala Ala
1               5                   10                  15

Gly Ala Gly

<210> SEQ ID NO 21
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (13)..(13)
<223> OTHER INFORMATION: AMIDATION

<400> SEQUENCE: 21

Gly Cys Cys Ser Asp Pro Arg Cys Arg Tyr Arg Cys Arg
1               5                   10

<210> SEQ ID NO 22
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 22

Gly Cys Cys Ser Asp Pro Arg Cys Arg Xaa Arg Cys Arg
1               5                   10

<210> SEQ ID NO 23
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 23

Gly Cys Cys Thr Asp Pro Arg Cys Xaa Xaa Gln Cys Arg
1               5                   10

<210> SEQ ID NO 24
<211> LENGTH: 15
```

```
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (15)..(15)
<223> OTHER INFORMATION: AMIDATION

<400> SEQUENCE: 24

Gly Cys Cys Thr Asp Pro Arg Cys Xaa Xaa Gln Cys Arg Arg Arg
1               5                   10                  15

<210> SEQ ID NO 25
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (2)..(2)
<223> OTHER INFORMATION: Cys, any natural amino acid, or any unnatural
      amino acid
<220> FEATURE:
<221> NAME/KEY: VARIANT
<222> LOCATION: (3)..(3)
<223> OTHER INFORMATION: Cys, any natural amino acid, or any unnatural
      amino acid
<220> FEATURE:
<221> NAME/KEY: VARIANT
<222> LOCATION: (8)..(8)
<223> OTHER INFORMATION: Cys, any natural amino acid, or any unnatural
      amino acid
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: VARIANT
<222> LOCATION: (12)..(12)
<223> OTHER INFORMATION: Cys, any natural amino acid, or any unnatural
      amino acid
<220> FEATURE:
<221> NAME/KEY: MOD_RES
<222> LOCATION: (13)..(13)
<223> OTHER INFORMATION: AMIDATION

<400> SEQUENCE: 25

Gly Xaa Xaa Thr Asp Pro Arg Xaa Xaa Xaa Gln Xaa Tyr
1               5                   10

<210> SEQ ID NO 26
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
```

```
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 26

Gly Xaa Cys Thr Asp Pro Arg Xaa Xaa Xaa Gln Cys Arg
1               5                   10

<210> SEQ ID NO 27
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 27

Gly Cys Cys Thr Asp Pro Arg Cys Arg Xaa Gln Cys Phe
1               5                   10

<210> SEQ ID NO 28
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 28

Gly Cys Cys Thr Asp Pro Arg Cys Arg Xaa Gln Cys Tyr
1               5                   10

<210> SEQ ID NO 29
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION
```

```
<400> SEQUENCE: 29

Gly Cys Cys Thr Asp Pro Arg Cys Arg Xaa Gln Cys Trp
1               5                   10

<210> SEQ ID NO 30
<211> LENGTH: 13
<212> TYPE: PRT
<213> ORGANISM: Artificial sequence
<220> FEATURE:
<223> OTHER INFORMATION: RgIA analog

<400> SEQUENCE: 30

Gly Cys Cys Ser Asp Pro Arg Cys Arg Tyr Arg Cys His
1               5                   10

<210> SEQ ID NO 31
<211> LENGTH: 13
<212> TYPE: PRT
<213> ORGANISM: Artificial sequence
<220> FEATURE:
<223> OTHER INFORMATION: RgIA analog

<400> SEQUENCE: 31

Gly Cys Cys Ser Asp Pro Arg Cys Arg Tyr Arg Cys Lys
1               5                   10

<210> SEQ ID NO 32
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (10)..(10)
<223> OTHER INFORMATION: O-phospho-Tyr, O-sulfo-Tyr, or O-fluoro-Tyr

<400> SEQUENCE: 32

Gly Cys Cys Ser Asp Pro Arg Cys Arg Xaa Arg Cys Arg
1               5                   10

<210> SEQ ID NO 33
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: mono-fluoro-Glycine

<400> SEQUENCE: 33

Xaa Cys Cys Ser Asp Pro Arg Cys Arg Tyr Arg Cys Arg
1               5                   10

<210> SEQ ID NO 34
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: di-fluoro-Glycine

<400> SEQUENCE: 34
```

Xaa Cys Cys Ser Asp Pro Arg Cys Arg Tyr Arg Cys Arg
1               5                   10

<210> SEQ ID NO 35
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro

<400> SEQUENCE: 35

Gly Cys Cys Ser Asp Xaa Arg Cys Arg Tyr Arg Cys Arg
1               5                   10

<210> SEQ ID NO 36
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp

<400> SEQUENCE: 36

Gly Cys Cys Ser Xaa Pro Arg Cys Arg Tyr Arg Cys Arg
1               5                   10

<210> SEQ ID NO 37
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (7)..(7)
<223> OTHER INFORMATION: D-Arg

<400> SEQUENCE: 37

Gly Cys Cys Ser Asp Pro Xaa Cys Arg Tyr Arg Cys Arg
1               5                   10

<210> SEQ ID NO 38
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro

<400> SEQUENCE: 38

Gly Cys Cys Ser Xaa Xaa Arg Cys Arg Tyr Arg Cys Arg
1               5                   10

<210> SEQ ID NO 39
<211> LENGTH: 13
<212> TYPE: PRT

-continued

<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg

<400> SEQUENCE: 39

Gly Cys Cys Ser Asp Xaa Xaa Cys Arg Tyr Arg Cys Arg
1 5 10

<210> SEQ ID NO 40
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg

<400> SEQUENCE: 40

Gly Cys Cys Ser Xaa Xaa Xaa Cys Arg Tyr Arg Cys Arg
1 5 10

<210> SEQ ID NO 41
<211> LENGTH: 13
<212> TYPE: PRT
<213> ORGANISM: Artificial sequence
<220> FEATURE:
<223> OTHER INFORMATION: RgIA analog

<400> SEQUENCE: 41

Gly Cys Cys Ser Asp Pro Arg Cys Arg Tyr His Cys Arg
1 5 10

<210> SEQ ID NO 42
<211> LENGTH: 13
<212> TYPE: PRT
<213> ORGANISM: Artificial sequence
<220> FEATURE:
<223> OTHER INFORMATION: RgIA analog

<400> SEQUENCE: 42

Gly Cys Cys Ser Asp Pro Arg Cys Arg Tyr Lys Cys Arg
1 5 10

<210> SEQ ID NO 43
<211> LENGTH: 13
<212> TYPE: PRT
<213> ORGANISM: Artificial sequence
<220> FEATURE:
<223> OTHER INFORMATION: RgIA analog

<400> SEQUENCE: 43

Pro Cys Cys Ser Asp Pro Arg Cys Arg Tyr Arg Cys Arg

<210> SEQ ID NO 44
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 44

Gly Cys Cys Ser Asp Pro Arg Cys Arg Xaa Arg Cys His
1               5                   10

<210> SEQ ID NO 45
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 45

Gly Cys Cys Ser Asp Pro Arg Cys Arg Xaa Arg Cys Lys
1               5                   10

<210> SEQ ID NO 46
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (10)..(10)
<223> OTHER INFORMATION: O-phospho-Tyr, O-sulfo-Tyr, or O-fluoro-Tyr

<400> SEQUENCE: 46

Gly Cys Cys Ser Asp Pro Arg Cys Arg Xaa Arg Cys His
1               5                   10

<210> SEQ ID NO 47
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: mono-fluoro-Glycine
<220> FEATURE:
<221> NAME/KEY: MOD_RES
<222> LOCATION: (10)..(10)
<223> OTHER INFORMATION: 3-iodo-Tyrosine

<400> SEQUENCE: 47

Xaa Cys Cys Ser Asp Pro Arg Cys Arg Xaa Arg Cys Arg
1               5                   10

<210> SEQ ID NO 48
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: di-fluoro-Glycine
<220> FEATURE:
<221> NAME/KEY: MOD_RES
<222> LOCATION: (10)..(10)
<223> OTHER INFORMATION: 3-iodo-Tyrosine

<400> SEQUENCE: 48

Xaa Cys Cys Ser Asp Pro Arg Cys Arg Xaa Arg Cys Arg
1               5                   10

<210> SEQ ID NO 49
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (10)..(10)
<223> OTHER INFORMATION: 3-iodo-Tyrosine

<400> SEQUENCE: 49

Gly Cys Cys Ser Asp Xaa Arg Cys Arg Xaa Arg Cys Arg
1               5                   10

<210> SEQ ID NO 50
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (10)..(10)
<223> OTHER INFORMATION: 3-iodo-Tyrosine

<400> SEQUENCE: 50

Gly Cys Cys Ser Xaa Pro Arg Cys Arg Xaa Arg Cys Arg
1               5                   10

<210> SEQ ID NO 51
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 51

Gly Cys Cys Ser Asp Pro Xaa Cys Arg Xaa Arg Cys Arg
1               5                   10

```
<210> SEQ ID NO 52
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (10)..(10)
<223> OTHER INFORMATION: 3-iodo-Tyrosine

<400> SEQUENCE: 52

Gly Cys Cys Ser Xaa Xaa Arg Cys Arg Xaa Arg Cys Arg
1               5                   10

<210> SEQ ID NO 53
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 53

Gly Cys Cys Ser Asp Xaa Xaa Cys Arg Xaa Arg Cys Arg
1               5                   10

<210> SEQ ID NO 54
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 54

Gly Cys Cys Ser Xaa Xaa Xaa Cys Arg Xaa Arg Cys Arg
1               5                   10
```

```
<210> SEQ ID NO 55
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 55

Gly Cys Cys Ser Asp Pro Arg Cys Arg Xaa His Cys Arg
1               5                   10

<210> SEQ ID NO 56
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 56

Gly Cys Cys Ser Asp Pro Arg Cys Arg Xaa Lys Cys Arg
1               5                   10

<210> SEQ ID NO 57
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 57

Pro Cys Cys Ser Asp Pro Arg Cys Arg Xaa Arg Cys Arg
1               5                   10

<210> SEQ ID NO 58
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 58

Gly Cys Cys Ser Asp Pro Arg Cys His Xaa Arg Cys Arg
1               5                   10

<210> SEQ ID NO 59
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine
```

<400> SEQUENCE: 59

Gly Cys Cys Ser Asp Pro Arg Cys Lys Xaa Arg Cys Arg
1               5                   10

<210> SEQ ID NO 60
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 60

Gly Cys Cys Thr Asp Pro Arg Cys Arg Xaa Arg Cys His
1               5                   10

<210> SEQ ID NO 61
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 61

Gly Cys Cys Thr Asp Pro Arg Cys Arg Xaa Arg Cys Lys
1               5                   10

<210> SEQ ID NO 62
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (10)..(10)
<223> OTHER INFORMATION: O-phospho-Tyr, O-sulfo-Tyr, or O-fluoro-Tyr

<400> SEQUENCE: 62

Gly Cys Cys Thr Asp Pro Arg Cys Arg Xaa Arg Cys Arg
1               5                   10

<210> SEQ ID NO 63
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: mono-fluoro-Glycine
<220> FEATURE:
<221> NAME/KEY: MOD_RES
<222> LOCATION: (10)..(10)
<223> OTHER INFORMATION: 3-iodo-Tyrosine

<400> SEQUENCE: 63

Xaa Cys Cys Thr Asp Pro Arg Cys Arg Xaa Arg Cys Arg
1               5                   10

```
<210> SEQ ID NO 64
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: di-fluoro-Glycine
<220> FEATURE:
<221> NAME/KEY: MOD_RES
<222> LOCATION: (10)..(10)
<223> OTHER INFORMATION: 3-iodo-Tyrosine

<400> SEQUENCE: 64

Xaa Cys Cys Thr Asp Pro Arg Cys Arg Xaa Arg Cys Arg
1               5                   10

<210> SEQ ID NO 65
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (10)..(10)
<223> OTHER INFORMATION: 3-iodo-Tyrosine

<400> SEQUENCE: 65

Gly Cys Cys Thr Asp Xaa Arg Cys Arg Xaa Arg Cys Arg
1               5                   10

<210> SEQ ID NO 66
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (10)..(10)
<223> OTHER INFORMATION: 3-iodo-Tyrosine

<400> SEQUENCE: 66

Gly Cys Cys Thr Xaa Pro Arg Cys Arg Xaa Arg Cys Arg
1               5                   10

<210> SEQ ID NO 67
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 67
```

Gly Cys Cys Thr Asp Pro Xaa Cys Arg Xaa Arg Cys Arg
1               5                   10

<210> SEQ ID NO 68
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (10)..(10)
<223> OTHER INFORMATION: 3-iodo-Tyrosine

<400> SEQUENCE: 68

Gly Cys Cys Thr Xaa Xaa Arg Cys Arg Xaa Arg Cys Arg
1               5                   10

<210> SEQ ID NO 69
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 69

Gly Cys Cys Thr Asp Xaa Xaa Cys Arg Xaa Arg Cys Arg
1               5                   10

<210> SEQ ID NO 70
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 70

```
Gly Cys Cys Thr Xaa Xaa Xaa Cys Arg Xaa Arg Cys Arg
1               5                   10
```

<210> SEQ ID NO 71
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 71

```
Gly Cys Cys Thr Asp Pro Arg Cys Arg Xaa His Cys Arg
1               5                   10
```

<210> SEQ ID NO 72
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 72

```
Gly Cys Cys Thr Asp Pro Arg Cys Arg Xaa Lys Cys Arg
1               5                   10
```

<210> SEQ ID NO 73
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 73

```
Pro Cys Cys Thr Asp Pro Arg Cys Arg Xaa Arg Cys Arg
1               5                   10
```

<210> SEQ ID NO 74
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 74

```
Gly Cys Cys Thr Asp Pro Arg Cys His Xaa Arg Cys Arg
1               5                   10
```

<210> SEQ ID NO 75
<211> LENGTH: 13
<212> TYPE: PRT
<213> ORGANISM: Artificial sequence
<220> FEATURE:
<223> OTHER INFORMATION: RgIA analog

```
<220> FEATURE:
<221> NAME/KEY: MOD_RES
<222> LOCATION: (10)..(10)
<223> OTHER INFORMATION: 3-iodo-Tyrosine

<400> SEQUENCE: 75

Gly Cys Cys Thr Asp Pro Arg Cys Lys Xaa Arg Cys Arg
1               5                   10

<210> SEQ ID NO 76
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 76

Gly Cys Cys Thr Asp Pro Arg Cys Xaa Xaa Gln Cys His Arg Arg
1               5                   10                  15

<210> SEQ ID NO 77
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 77

Gly Cys Cys Thr Asp Pro Arg Cys Xaa Xaa Gln Cys Lys Arg Arg
1               5                   10                  15

<210> SEQ ID NO 78
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 78

Gly Cys Cys Thr Asp Pro Arg Cys Xaa Xaa Gln Cys Arg His Arg
1               5                   10                  15

<210> SEQ ID NO 79
<211> LENGTH: 15
<212> TYPE: PRT
<213> ORGANISM: Artificial sequence
<220> FEATURE:
```

```
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 79

Gly Cys Cys Thr Asp Pro Arg Cys Xaa Xaa Gln Cys Arg Lys Arg
1               5                   10                  15

<210> SEQ ID NO 80
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 80

Gly Cys Cys Thr Asp Pro Arg Cys Xaa Xaa Gln Cys Arg Arg His
1               5                   10                  15

<210> SEQ ID NO 81
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 81

Gly Cys Cys Thr Asp Pro Arg Cys Xaa Xaa Gln Cys Arg Arg Lys
1               5                   10                  15

<210> SEQ ID NO 82
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: VARIANT
<222> LOCATION: (10)..(10)
<223> OTHER INFORMATION: O-phospho-Tyr, O-sulfo-Tyr, or O-fluoro-Tyr

<400> SEQUENCE: 82

Gly Cys Cys Thr Asp Pro Arg Cys Xaa Xaa Gln Cys Arg Arg Arg
1               5                   10                  15
```

```
<210> SEQ ID NO 83
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: mono-fluoro-Glycine
<220> FEATURE:

```
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 86

Gly Cys Cys Thr Xaa Pro Arg Cys Xaa Xaa Gln Cys Arg Arg Arg
1               5                   10                  15

<210> SEQ ID NO 87
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 87

Gly Cys Cys Thr Asp Pro Xaa Cys Xaa Xaa Gln Cys Arg Arg Arg
1               5                   10                  15

<210> SEQ ID NO 88
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 88

Gly Cys Cys Thr Xaa Xaa Arg Cys Xaa Xaa Gln Cys Arg Arg Arg
1               5                   10                  15

<210> SEQ ID NO 89
<211> LENGTH: 15
<212> TYPE: PRT
<213> ORGANISM: Artificial sequence
```

-continued

```
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 89

Gly Cys Cys Thr Asp Xaa Xaa Cys Xaa Xaa Gln Cys Arg Arg Arg
1               5                   10                  15

<210> SEQ ID NO 90
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 90

Gly Cys Cys Thr Xaa Xaa Xaa Cys Xaa Xaa Gln Cys Arg Arg Arg
1               5                   10                  15

<210> SEQ ID NO 91
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 91

Pro Cys Cys Thr Asp Pro Arg Cys Xaa Xaa Gln Cys Arg Arg Arg
1               5                   10                  15
```

```
<210> SEQ ID NO 92
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: VARIANT
<222> LOCATION: (10)..(10)
<223> OTHER INFORMATION: O-phospho-Tyr, O-sulfo-Tyr, or O-fluoro-Tyr

<400> SEQUENCE: 92

Gly Cys Cys Thr Asp Pro Arg Cys Xaa Xaa Gln Cys Tyr
 1               5                  10

<210> SEQ ID NO 93
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: VARIANT
<222> LOCATION: (13)..(13)
<223> OTHER INFORMATION: O-phospho-Tyr, O-sulfo-Tyr, or O-fluoro-Tyr

<400> SEQUENCE: 93

Gly Cys Cys Thr Asp Pro Arg Cys Xaa Xaa Gln Cys Xaa
 1               5                  10

<210> SEQ ID NO 94
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: mono-fluoro-Glycine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 94

Xaa Cys Cys Thr Asp Pro Arg Cys Xaa Xaa Gln Cys Tyr
 1               5                  10

<210> SEQ ID NO 95
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
```

```
<222> LOCATION: (1)..(1)
<223> OTHER INFORMATION: di-fluoro-Glycine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 95

Xaa Cys Cys Thr Asp Pro Arg Cys Xaa Xaa Gln Cys Tyr
1               5                   10

<210> SEQ ID NO 96
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 96

Gly Cys Cys Thr Asp Xaa Arg Cys Xaa Xaa Gln Cys Tyr
1               5                   10

<210> SEQ ID NO 97
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 97

Gly Cys Cys Thr Xaa Pro Arg Cys Xaa Xaa Gln Cys Tyr
1               5                   10

<210> SEQ ID NO 98
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
```

<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 98

Gly Cys Cys Thr Asp Pro Xaa Cys Xaa Xaa Gln Cys Tyr
1               5                   10

<210> SEQ ID NO 99
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 99

Gly Cys Cys Thr Xaa Xaa Arg Cys Xaa Xaa Gln Cys Tyr
1               5                   10

<210> SEQ ID NO 100
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 100

Gly Cys Cys Thr Asp Xaa Xaa Cys Xaa Xaa Gln Cys Tyr
1               5                   10

<210> SEQ ID NO 101
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES

```
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 101

Gly Cys Cys Thr Xaa Xaa Xaa Cys Xaa Xaa Gln Cys Tyr
1               5                   10

<210> SEQ ID NO 102
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 102

Pro Cys Cys Thr Asp Pro Arg Cys Xaa Xaa Gln Cys Tyr
1               5                   10

<210> SEQ ID NO 103
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 103

Gly Xaa Cys Thr Asp Pro Arg Xaa Xaa Xaa Gln Cys His
1               5                   10

<210> SEQ ID NO 104
<211> LENGTH: 13
<212> TYPE: PRT
<213> ORGANISM: Artificial sequence
```

```
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 104

Gly Xaa Cys Thr Asp Pro Arg Xaa Xaa Xaa Gln Cys Lys
1               5                   10

<210> SEQ ID NO 105
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: VARIANT
<222> LOCATION: (10)..(10)
<223> OTHER INFORMATION: O-phospho-Tyr, O-sulfo-Tyr, or O-fluoro-Tyr

<400> SEQUENCE: 105

Gly Xaa Cys Thr Asp Pro Arg Xaa Xaa Xaa Gln Cys Arg
1               5                   10

<210> SEQ ID NO 106
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: mono-fluoro-Glycine
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
```

```
<223> OTHER INFORMATION: 3-iodo-Tyrosine

<400> SEQUENCE: 106

Xaa Xaa Cys Thr Asp Pro Arg Xaa Xaa Xaa Gln Cys Arg
1               5                   10

<210> SEQ ID NO 107
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: di-fluoro-Glycine
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 107

Xaa Xaa Cys Thr Asp Pro Arg Xaa Xaa Xaa Gln Cys Arg
1               5                   10

<210> SEQ ID NO 108
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 108

Gly Xaa Cys Thr Asp Xaa Arg Xaa Xaa Xaa Gln Cys Arg
1               5                   10

<210> SEQ ID NO 109
<211> LENGTH: 13
<212> TYPE: PRT
<213> ORGANISM: Artificial sequence
<220> FEATURE:
```

```
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 109

Gly Xaa Cys Thr Xaa Pro Arg Xaa Xaa Xaa Gln Cys Arg
1               5                   10

<210> SEQ ID NO 110
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 110

Gly Xaa Cys Thr Asp Pro Xaa Xaa Xaa Xaa Gln Cys Arg
1               5                   10

<210> SEQ ID NO 111
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
```

```
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 111

Gly Xaa Cys Thr Xaa Xaa Arg Xaa Xaa Xaa Gln Cys Arg
1               5                   10

<210> SEQ ID NO 112
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 112

Gly Xaa Cys Thr Asp Xaa Xaa Xaa Xaa Xaa Gln Cys Arg
1               5                   10

<210> SEQ ID NO 113
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
```

```
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 113

Gly Xaa Cys Thr Xaa Xaa Xaa Xaa Xaa Xaa Gln Cys Arg
1               5                   10

<210> SEQ ID NO 114
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 114

Pro Xaa Cys Thr Asp Pro Arg Xaa Xaa Xaa Gln Cys Arg
1               5                   10

<210> SEQ ID NO 115
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (10)..(10)
<223> OTHER INFORMATION: O-phospho-Tyr, O-sulfo-Tyr, or O-fluoro-Tyr

<400> SEQUENCE: 115

Gly Cys Cys Thr Asp Pro Arg Cys Arg Xaa Gln Cys Phe
1               5                   10

<210> SEQ ID NO 116
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: mono-fluoro-Glycine
<220> FEATURE:
<221> NAME/KEY: MOD_RES
<222> LOCATION: (10)..(10)
<223> OTHER INFORMATION: 3-iodo-Tyrosine
```

```
<400> SEQUENCE: 116

Xaa Cys Cys Thr Asp Pro Arg Cys Arg Xaa Gln Cys Phe
1               5                   10

<210> SEQ ID NO 117
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: di-fluoro-Glycine
<220> FEATURE:
<221> NAME/KEY: MOD_RES
<222> LOCATION: (10)..(10)
<223> OTHER INFORMATION: 3-iodo-Tyrosine

<400> SEQUENCE: 117

Xaa Cys Cys Thr Asp Pro Arg Cys Arg Xaa Gln Cys Phe
1               5                   10

<210> SEQ ID NO 118
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (10)..(10)
<223> OTHER INFORMATION: 3-iodo-Tyrosine

<400> SEQUENCE: 118

Gly Cys Cys Thr Asp Xaa Arg Cys Arg Xaa Gln Cys Phe
1               5                   10

<210> SEQ ID NO 119
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (10)..(10)
<223> OTHER INFORMATION: 3-iodo-Tyrosine

<400> SEQUENCE: 119

Gly Cys Cys Thr Xaa Pro Arg Cys Arg Xaa Gln Cys Phe
1               5                   10

<210> SEQ ID NO 120
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (7)..(7)
<223> OTHER INFORMATION: D-Arg
```

```
<220> FEATURE:
<221> NAME/KEY: MOD_RES
<222> LOCATION: (10)..(10)
<223> OTHER INFORMATION: 3-iodo-Tyrosine

<400> SEQUENCE: 120

Gly Cys Cys Thr Asp Pro Xaa Cys Arg Xaa Gln Cys Phe
1               5                   10

<210> SEQ ID NO 121
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (10)..(10)
<223> OTHER INFORMATION: 3-iodo-Tyrosine

<400> SEQUENCE: 121

Gly Cys Cys Thr Xaa Xaa Arg Cys Arg Xaa Gln Cys Phe
1               5                   10

<210> SEQ ID NO 122
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 122

Gly Cys Cys Thr Asp Xaa Xaa Cys Arg Xaa Gln Cys Phe
1               5                   10

<210> SEQ ID NO 123
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
```

```
<220> FEATURE:
<221> NAME/KEY: MOD_RES
<222> LOCATION: (10)..(10)
<223> OTHER INFORMATION: 3-iodo-Tyrosine

<400> SEQUENCE: 123

Gly Cys Cys Thr Xaa Xaa Xaa Cys Arg Xaa Gln Cys Phe
1               5                   10

<210> SEQ ID NO 124
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 124

Pro Cys Cys Thr Asp Pro Arg Cys Arg Xaa Gln Cys Phe
1               5                   10

<210> SEQ ID NO 125
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (10)..(10)
<223> OTHER INFORMATION: O-phospho-Tyr, O-sulfo-Tyr, or O-fluoro-Tyr

<400> SEQUENCE: 125

Gly Cys Cys Thr Asp Pro Arg Cys Arg Xaa Gln Cys Tyr
1               5                   10

<210> SEQ ID NO 126
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: VARIANT
<222> LOCATION: (13)..(13)
<223> OTHER INFORMATION: O-phospho-Tyr, O-sulfo-Tyr, or O-fluoro-Tyr

<400> SEQUENCE: 126

Gly Cys Cys Thr Asp Pro Arg Cys Arg Xaa Gln Cys Xaa
1               5                   10

<210> SEQ ID NO 127
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: mono-fluoro-Glycine
<220> FEATURE:
<221> NAME/KEY: MOD_RES
<222> LOCATION: (10)..(10)
```

<223> OTHER INFORMATION: 3-iodo-Tyrosine

<400> SEQUENCE: 127

Xaa Cys Cys Thr Asp Pro Arg Cys Arg Xaa Gln Cys Tyr
1               5                   10

<210> SEQ ID NO 128
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: di-fluoro-Glycine
<220> FEATURE:
<221> NAME/KEY: MOD_RES
<222> LOCATION: (10)..(10)
<223> OTHER INFORMATION: 3-iodo-Tyrosine

<400> SEQUENCE: 128

Xaa Cys Cys Thr Asp Pro Arg Cys Arg Xaa Gln Cys Tyr
1               5                   10

<210> SEQ ID NO 129
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (10)..(10)
<223> OTHER INFORMATION: 3-iodo-Tyrosine

<400> SEQUENCE: 129

Gly Cys Cys Thr Asp Xaa Arg Cys Arg Xaa Gln Cys Tyr
1               5                   10

<210> SEQ ID NO 130
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (10)..(10)
<223> OTHER INFORMATION: 3-iodo-Tyrosine

<400> SEQUENCE: 130

Gly Cys Cys Thr Xaa Pro Arg Cys Arg Xaa Gln Cys Tyr
1               5                   10

<210> SEQ ID NO 131
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES -continued

```
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 131

Gly Cys Cys Thr Asp Pro Xaa Cys Arg Xaa Gln Cys Tyr
1               5                   10

<210> SEQ ID NO 132
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (10)..(10)
<223> OTHER INFORMATION: 3-iodo-Tyrosine

<400> SEQUENCE: 132

Gly Cys Cys Thr Xaa Xaa Arg Cys Arg Xaa Gln Cys Tyr
1               5                   10

<210> SEQ ID NO 133
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 133

Gly Cys Cys Thr Asp Xaa Xaa Cys Arg Xaa Gln Cys Tyr
1               5                   10

<210> SEQ ID NO 134
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
```

```
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 134

Gly Cys Cys Thr Xaa Xaa Xaa Cys Arg Xaa Gln Cys Tyr
1               5                   10

<210> SEQ ID NO 135
<211> LENGTH: 13
<212> TYPE: PRT
<213> ORGANISM: Artificial sequence
<220> FEATURE:
<223> OTHER INFORMATION: RgIA analog
<220> FE

```
<221> NAME/KEY: MOD_RES
<222> LOCATION: (10)..(10)
<223> OTHER INFORMATION: 3-iodo-Tyrosine

<400> SEQUENCE: 138

Xaa Cys Cys Thr Asp Pro Arg Cys Arg Xaa Gln Cys Trp
1               5                   10

<210> SEQ ID NO 139
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (10)..(10)
<223> OTHER INFORMATION: 3-iodo-Tyrosine

<400> SEQUENCE: 139

Gly Cys Cys Thr Asp Xaa Arg Cys Arg Xaa Gln Cys Trp
1               5                   10

<210> SEQ ID NO 140
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (10)..(10)
<223> OTHER INFORMATION: 3-iodo-Tyrosine

<400> SEQUENCE: 140

Gly Cys Cys Thr Xaa Pro Arg Cys Arg Xaa Gln Cys Trp
1               5                   10

<210> SEQ ID NO 141
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 141

Gly Cys Cys Thr Asp Pro Xaa Cys Arg Xaa Gln Cys Trp
1               5                   10

<210> SEQ ID NO 142
<211> LENGTH: 13
<212> TYPE: PRT
<213> ORGANISM: Artificial sequence
<220> FEATURE:
<223> OTHER INFORMATION: RgIA analog
```

```
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (10)..(10)
<223> OTHER INFORMATION: 3-iodo-Tyrosine

<400> SEQUENCE: 142

Gly Cys Cys Thr Xaa Xaa Arg Cys Arg Xaa Gln Cys Trp
1               5                   10

<210> SEQ ID NO 143
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 143

Gly Cys Cys Thr Asp Xaa Xaa Cys Arg Xaa Gln Cys Trp
1               5                   10

<210> SEQ ID NO 144
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (5)..(5)
<223> OTHER INFORMATION: D-Asp
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 144

Gly Cys Cys Thr Xaa Xaa Xaa Cys Arg Xaa Gln Cys Trp
1               5                   10

<210> SEQ ID NO 145
<211> LENGTH: 13
<212> TYPE: PRT
<213> ORGANISM: Artificial sequence
<220> FEATURE:
<223> OTHER INFORMATION: RgIA analog
```

```
<220> FEATURE:
<221> NAME/KEY: MOD_RES
<222> LOCATION: (10)..(10)
<223> OTHER INFORMATION: 3-iodo-Tyrosine

<400> SEQUENCE: 145

Pro Cys Cys Thr Asp Pro Arg Cys Arg Xaa Gln Cys Trp
1               5                   10

<210> SEQ ID NO 146
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 146

Gly Xaa Cys Thr Asp Pro Arg Cys Xaa Xaa Gln Cys Tyr
1               5                   10

<210> SEQ ID NO 147
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 147

Gly Cys Xaa Thr Asp Pro Arg Cys Xaa Xaa Gln Cys Tyr
1               5                   10

<210> SEQ ID NO 148
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
```

```
<400> SEQUENCE: 148

Gly Cys Cys Thr Asp Pro Arg Xaa Xaa Xaa Gln Cys Tyr
1               5                   10

<210> SEQ ID NO 149
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 149

Gly Cys Cys Thr Asp Pro Arg Cys Xaa Xaa Gln Xaa Tyr
1               5                   10

<210> SEQ ID NO 150
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 150

Gly Xaa Cys Thr Asp Pro Arg Xaa Xaa Xaa Gln Cys Tyr
1               5                   10

<210> SEQ ID NO 151
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
```

```
<220> FEATURE:
<221> NAME/KEY: MOD_RES
<222> LOCATION: (12)..(12)
<223> OTHER INFORMATION: Selenocysteine

<400> SEQUENCE: 151

Gly Cys Xaa Thr Asp Pro Arg Cys Xaa Xaa Gln Xaa Tyr
1               5                   10

<210> SEQ ID NO 152
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 152

Gly Xaa Xaa Thr Asp Pro Arg Cys Xaa Xaa Gln Cys Tyr
1               5                   10

<210> SEQ ID NO 153
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 153

Gly Cys Cys Thr Asp Pro Arg Xaa Xaa Xaa Gln Xaa Tyr
1               5                   10

<210> SEQ ID NO 154
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
```

```
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 154

Gly Xaa Cys Thr Asp Pro Arg Cys Xaa Xaa Gln Xaa Tyr
1               5                   10

<210> SEQ ID NO 155
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine

<400> SEQUENCE: 155

Gly Xaa Xaa Thr Asp Pro Arg Xaa Xaa Xaa Gln Cys Tyr
1               5                   10

<210> SEQ ID NO 156
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine
```

<400> SEQUENCE: 156

Gly Cys Xaa Thr Asp Pro Arg Xaa Xaa Xaa Gln Xaa Tyr
1               5                   10

<210> SEQ ID NO 157
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 157

Gly Xaa Cys Thr Asp Pro Arg Xaa Xaa Xaa Gln Xaa Tyr
1               5                   10

<210> SEQ ID NO 158
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 158

Gly Xaa Xaa Thr Asp Pro Arg Cys Xaa Xaa Gln Xaa Tyr
1               5                   10

<210> SEQ ID NO 159
<211> LENGTH: 13
<212> TYPE: PRT
<213> ORGANISM: Artificial sequence
<220> FEATURE:
<223> OTHER INFORMATION: RgIA analog
<220> FEATURE:

```
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 159

Gly Xaa Xaa Thr Asp Pro Arg Xaa Xaa Xaa Gln Xaa Tyr
1               5                   10

<210> SEQ ID NO 160
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine

<400> SEQUENCE: 160

Gly Xaa Cys Thr Asp Pro Arg Cys Arg Xaa Gln Cys Tyr
1               5                   10

<210> SEQ ID NO 161
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine

<400> SEQUENCE: 161

Gly Cys Xaa Thr Asp Pro Arg Cys Arg Xaa Gln Cys Tyr
1               5                   10

<210> SEQ ID NO 162
<211> LENGTH: 13
<212> TYPE: PRT
<213> ORGANISM: Artificial sequence
<220> FEATURE:
<223> OTHER INFORMATION: RgIA analog
<220> FEATURE:
```

```
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine

<400> SEQUENCE: 162

Gly Cys Cys Thr Asp Pro Arg Xaa Arg Xaa Gln Cys Tyr
1               5                   10

<210> SEQ ID NO 163
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 163

Gly Cys Cys Thr Asp Pro Arg Cys Arg Xaa Gln Xaa Tyr
1               5                   10

<210> SEQ ID NO 164
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine

<400> SEQUENCE: 164

Gly Xaa Cys Thr Asp Pro Arg Xaa Arg Xaa Gln Cys Tyr
1               5                   10

<210> SEQ ID NO 165
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine
```

```
<400> SEQUENCE: 165

Gly Cys Xaa Thr Asp Pro Arg Cys Arg Xaa Gln Xaa Tyr
1               5                   10

<210> SEQ ID NO 166
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine

<400> SEQUENCE: 166

Gly Xaa Xaa Thr Asp Pro Arg Cys Arg Xaa Gln Cys Tyr
1               5                   10

<210> SEQ ID NO 167
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 167

Gly Cys Cys Thr Asp Pro Arg Xaa Arg Xaa Gln Xaa Tyr
1               5                   10

<210> SEQ ID NO 168
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 168

Gly Xaa Cys Thr Asp Pro Arg Cys Arg Xaa Gln Xaa Tyr
1               5                   10
```

<210> SEQ ID NO 169
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine

<400> SEQUENCE: 169

Gly Xaa Xaa Thr Asp Pro Arg Xaa Arg Xaa Gln Cys Tyr
1               5                   10

<210> SEQ ID NO 170
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 170

Gly Cys Xaa Thr Asp Pro Arg Xaa Arg Xaa Gln Xaa Tyr
1               5                   10

<210> SEQ ID NO 171
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine
<220> FEATURE:

```
<221> NAME/KEY: MOD_RES
<222> LOCATION: (12)..(12)
<223> OTHER INFORMATION: Selenocysteine

<400> SEQUENCE: 171

Gly Xaa Cys Thr Asp Pro Arg Xaa Arg Xaa Gln Xaa Tyr
1               5                   10

<210> SEQ ID NO 172
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 172

Gly Xaa Xaa Thr Asp Pro Arg Cys Arg Xaa Gln Xaa Tyr
1               5                   10

<210> SEQ ID NO 173
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (3)..(3)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (12)..(12)
<223> OTHER INFORMATION: Selenocysteine

<400> SEQUENCE: 173

Gly Xaa Xaa Thr Asp Pro Arg Xaa Arg Xaa Gln Xaa Tyr
1               5                   10

<210> SEQ ID NO 174
<211> LENGTH: 14
<212> TYPE: PRT
<213> ORGANISM: Artificial sequence
<220> FEATURE:
<223> OTHER INFORMATION: RgIA analog
<220> FEATURE:
```

<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (5)..(5)
<223> OTHER INFORMATION: 2-amino ethoxyacetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)
<223> OTHER INFORMATION: des-Xaa, Arg, Tyr, Phe, Trp, Tyr-Tyr, Tyr-Arg, Arg-Arg-Arg, Arg-Arg, Arg-Tyr, Arg-Arg-Tyr, or Tyr-Arg-Arg

<400> SEQUENCE: 174

Xaa Xaa Xaa Xaa Xaa Asp Pro Arg Xaa Xaa Xaa Xaa Xaa Xaa
1               5                   10

<210> SEQ ID NO 175
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (6)..(6)
<223> OTHER INFORMATION: 2-amino ethoxyacetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)
<223> OTHER INFORMATION: des-Xaa, Arg, Tyr, Phe, Trp, Tyr-Tyr, Tyr-Arg,
      Arg-Arg-Arg, Arg-Arg, Arg-Tyr, Arg-Arg-Tyr, or Tyr-Arg-Arg

<400> SEQUENCE: 175

Xaa Xaa Xaa Xaa Asp Xaa Pro Arg Xaa Xaa Xaa Xaa Xaa Xaa
1               5                   10

<210> SEQ ID NO 176
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (7)..(7)
<223> OTHER INFORMATION: 2-amino ethoxyacetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)

```
<223> OTHER INFORMATION: des-Xaa, Arg, Tyr, Phe, Trp, Tyr-Tyr, Tyr-Arg,
      Arg-Arg-Arg, Arg-Arg, Arg-Tyr, Arg-Arg-Tyr, or Tyr-Arg-Arg

<400> SEQUENCE: 176

Xaa Xaa Xaa Xaa Asp Pro Xaa Arg Xaa Xaa Xaa Xaa Xaa Xaa
1               5                   10

<210> SEQ ID NO 177
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (8)..(8)
<223> OTHER INFORMATION: 2-amino ethoxyacetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)
<223> OTHER INFORMATION: des-Xaa, Arg, Tyr, Phe, Trp, Tyr-Tyr, Tyr-Arg,
      Arg-Arg-Arg, Arg-Arg, Arg-Tyr, Arg-Arg-Tyr, or Tyr-Arg-Arg

<400> SEQUENCE: 177

Xaa Xaa Xaa Xaa Asp Pro Arg Xaa Xaa Xaa Xaa Xaa Xaa Xaa
1               5                   10

<210> SEQ ID NO 178
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (1)..(1)
<223> OTHER INFORMATION: des-Xaa or Gly
<220> FEATURE:
<221> NAME/KEY: VARIANT
```

```
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (5)..(5)
<223> OTHER INFORMATION: 2-[2-[ethoxy]ethoxy]acetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)
<223> OTHER INFORMATION: des-Xaa, Arg, Tyr, Phe, Trp, Tyr-Tyr, Tyr-Arg,
      Arg-Arg-Arg, Arg-Arg, Arg-Tyr, Arg-Arg-Tyr, or Tyr-Arg-Arg

<400> SEQUENCE: 178

Xaa Xaa Xaa Xaa Xaa Asp Pro Arg Xaa Xaa Xaa Xaa Xaa Xaa
1               5                   10

<210> SEQ ID NO 179
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (6)..(6)
<223> OTHER INFORMATION: 2-[2-[ethoxy]ethoxy]acetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
```

```
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)
<223> OTHER INFORMATION: des-Xaa, Arg, Tyr, Phe, Trp, Tyr-Tyr, Tyr-Arg,
     Arg-Arg-Arg, Arg-Arg, Arg-Tyr, Arg-Arg-Tyr, or Tyr-Arg-Arg

<400> SEQUENCE: 179

Xaa Xaa Xaa Xaa Asp Xaa Pro Arg Xaa Xaa Xaa Xaa Xaa Xaa
1               5                   10

<210> SEQ ID NO 180
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (7)..(7)
<223> OTHER INFORMATION: 2-[2-[ethoxy]ethoxy]acetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)
<223> OTHER INFORMATION: des-Xaa, Arg, Tyr, Phe, Trp, Tyr-Tyr, Tyr-Arg,
     Arg-Arg-Arg, Arg-Arg, Arg-Tyr, Arg-Arg-Tyr, or Tyr-Arg-Arg

<400> SEQUENCE: 180
```

-continued

Xaa Xaa Xaa Xaa Asp Pro Xaa Arg Xaa Xaa Xaa Xaa Xaa Xaa
1               5                   10

<210> SEQ ID NO 181
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (8)..(8)
<223> OTHER INFORMATION: 2-[2-[ethoxy]ethoxy]acetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)
<223> OTHER INFORMATION: des-Xaa, Arg, Tyr, Phe, Trp, Tyr-Tyr, Tyr-Arg,
     Arg-Arg-Arg, Arg-Arg, Arg-Tyr, Arg-Arg-Tyr, or Tyr-Arg-Arg

<400> SEQUENCE: 181

Xaa Xaa Xaa Xaa Asp Pro Arg Xaa Xaa Xaa Xaa Xaa Xaa Xaa
1               5                   10

<210> SEQ ID NO 182
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)

```
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (5)..(5)
<223> OTHER INFORMATION: 2-[2-[2-[ethoxy]ethoxy]ethoxy]acetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)
<223> OTHER INFORMATION: des-Xaa, Arg, Tyr, Phe, Trp, Tyr-Tyr, Tyr-Arg,
      Arg-Arg-Arg, Arg-Arg, Arg-Tyr, Arg-Arg-Tyr, or Tyr-Arg-Arg

<400> SEQUENCE: 182

Xaa Xaa Xaa Xaa Xaa Asp Pro Arg Xaa Xaa Xaa Xaa Xaa Xaa
1               5                   10

<210> SEQ ID NO 183
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (6)..(6)
<223> OTHER INFORMATION: 2-[2-[2-[ethoxy]ethoxy]ethoxy]acetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
```

```
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)
<223> OTHER INFORMATION: des-Xaa, Arg, Tyr, Phe, Trp, Tyr-Tyr, Tyr-Arg,
      Arg-Arg-Arg, Arg-Arg, Arg-Tyr, Arg-Arg-Tyr, or Tyr-Arg-Arg

<400> SEQUENCE: 183

Xaa Xaa Xaa Xaa Asp Xaa Pro Arg Xaa Xaa Xaa Xaa Xaa Xaa
1               5                   10

<210> SEQ ID NO 184
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (7)..(7)
<223> OTHER INFORMATION: 2-[2-[2-[ethoxy]ethoxy]ethoxy]acetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)
<223> OTHER INFORMATION: des-Xaa, Arg, Tyr, Phe, Trp, Tyr-Tyr, Tyr-Arg,
      Arg-Arg-Arg, Arg-Arg, Arg-Tyr, Arg-Arg-Tyr, or Tyr-Arg-Arg

<400> SEQUENCE: 184

Xaa Xaa Xaa Xaa Asp Pro Xaa Arg Xaa Xaa Xaa Xaa Xaa Xaa
1               5                   10

<210> SEQ ID NO 185
```

```
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (1)..(1)
<223> OTHER INFORMATION: des-Xaa or Gly
<220> FEATURE:
<221> NAME/KEY: VARIANT
<222> LOCATION: (2)..(2)
<223> OTHER INFORMATION: des-Xaa, Cys, or selenocysteine
<220> FEATURE:
<221> NAME/KEY: VARIANT
<222> LOCATION: (3)..(3)
<223> OTHER INFORMATION: des-Xaa, Cys, or selenocysteine
<220> FEATURE:
<221> NAME/KEY: VARIANT
<222> LOCATION: (4)..(4)
<223> OTHER INFORMATION: des-Xaa, Ser, or Thr
<220> FEATURE:
<221> NAME/KEY: MISC_FEATURE
<222> LOCATION: (8)..(8)
<223> OTHER INFORMATION: 2-[2-[2-[ethoxy]ethoxy]ethoxy]acetic acid
<220> FEATURE:
<221> NAME/KEY: VARIANT
<222> LOCATION: (9)..(9)
<223> OTHER INFORMATION: des-Xaa, Cys, or selenocysteine
<220> FEATURE:
<221> NAME/KEY: VARIANT
<222> LOCATION: (10)..(10)
<223> OTHER INFORMATION: des-Xaa, Arg, citrulline, or omega-nitro-Arg
<220> FEATURE:
<221> NAME/KEY: VARIANT
<222> LOCATION: (11)..(11)
<223> OTHER INFORMATION: des-Xaa, Tyr, or mono-iodo-Tyr
<220> FEATURE:
<221> NAME/KEY: VARIANT
<222> LOCATION: (12)..(12)
<223> OTHER INFORMATION: des-Xaa, Arg, or Gln
<220> FEATURE:
<221> NAME/KEY: VARIANT
<222> LOCATION: (13)..(13)
<223> OTHER INFORMATION: des-Xaa, Cys, or selenocysteine
<220> FEATURE:
<221> NAME/KEY: VARIANT
<222> LOCATION: (14)..(14)
<223> OTHER INFORMATION: des-Xaa, Arg, Tyr, Phe, Trp, Tyr-Tyr, Tyr-Arg,
     Arg-Arg-Arg, Arg-Arg, Arg-Tyr, Arg-Arg-Tyr, or Tyr-Arg-Arg

<400> SEQUENCE: 185

Xaa Xaa Xaa Xaa Asp Pro Arg Xaa Xaa Xaa Xaa Xaa Xaa Xaa
1               5                   10

<210> SEQ ID NO 186
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation

<400> SEQUENCE: 186

Gly Cys Cys Ser Asp Pro Arg Cys Arg Tyr Arg Cys Arg
1               5                   10

<210> SEQ ID NO 187
<211> LENGTH: 13
<212> TYPE: PRT
<213> ORGANISM: Artificial sequence
<220> FEATURE:
```

```
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr

<400> SEQUENCE: 187

Gly Cys Cys Ser Asp Pro Arg Cys Arg Xaa Arg Cys Arg
1               5                   10

<210> SEQ ID NO 188
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr

<400> SEQUENCE: 188

Gly Cys Cys Thr Asp Pro Arg Cys Xaa Xaa Gln Cys Arg
1               5                   10

<210> SEQ ID NO 189
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr

<400> SEQUENCE: 189

Gly Cys Cys Thr Asp Pro Arg Cys Xaa Xaa Gln Cys Arg Arg Arg
1               5                   10                  15

<210> SEQ ID NO 190
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
```

```
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr

<400> SEQUENCE: 190

Gly Cys Cys Thr Asp Pro Arg Cys Xaa Xaa Gln Cys Tyr
1               5                   10

<210> SEQ ID NO 191
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (2)..(2)
<223> OTHER INFORMATION: des-Xaa, Arg, or Gln
<220> FEATURE:
<221> NAME/KEY: VARIANT
<222> LOCATION: (8)..(8)
<223> OTHER INFORMATION: des-Xaa, Arg, or Gln
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr

<400> SEQUENCE: 191

Gly Xaa Cys Thr Asp Pro Arg Xaa Xaa Xaa Gln Cys Arg
1               5                   10

<210> SEQ ID NO 192
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr

<400> SEQUENCE: 192

Gly Cys Cys Thr Asp Pro Arg Cys Arg Xaa Gln Cys Phe
1               5                   10

<210> SEQ ID NO 193
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
```

```
<223> OTHER INFORMATION: des-Xaa, Ser, or Thr

<400> SEQUENCE: 193

Gly Cys Cys Thr Asp Pro Arg Cys Arg Xaa Gln Cys Tyr
1               5                   10

<210> SEQ ID NO 194
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr

<400> SEQUENCE: 194

Gly Cys Cys Thr Asp Pro Arg Cys Arg Xaa Gln Cys Trp
1               5                   10

<210> SEQ ID NO 195
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: MOD_RES
<222> LOCATION: (13)..(13)
<223> OTHER INFORMATION: AMIDATION

<400> SEQUENCE: 195

Gly Cys Cys Ser Asp Pro Arg Cys Arg Tyr Arg Cys Arg
1               5                   10

<210> SEQ ID NO 196
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: AMIDATION

<400> SEQUENCE: 196

Gly Cys Cys Ser Asp Pro Arg Cys Arg Xaa Arg Cys Arg
1               5                   10

<210> SEQ ID NO 197
<211> LENGTH: 13
<212> TYPE: PRT
<213> ORGANISM: Artificial sequence
```

-continued

```
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: AMIDATION

<400> SEQUENCE: 197

Gly Cys Cys Thr Asp Pro Arg Cys Xaa Xaa Gln Cys Arg
1               5                   10

<210> SEQ ID NO 198
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (15)..(15)
<223> OTHER INFORMATION: AMIDATION

<400> SEQUENCE: 198

Gly Cys Cys Thr Asp Pro Arg Cys Xaa Xaa Gln Cys Arg Arg Arg
1               5                   10                  15

<210> SEQ ID NO 199
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: AMIDATION

<400> SEQUENCE: 199
```

Gly Cys Cys Thr Asp Pro Arg Cys Xaa Xaa Gln Cys Tyr
1               5                   10

<210> SEQ ID NO 200
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (2)..(2)
<223> OTHER INFORMATION: des-Xaa, Arg, or Gln
<220> FEATURE:
<221> NAME/KEY: VARIANT
<222> LOCATION: (8)..(8)
<223> OTHER INFORMATION: des-Xaa, Arg, or Gln
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: AMIDATION

<400> SEQUENCE: 200

Gly Xaa Cys Thr Asp Pro Arg Xaa Xaa Xaa Gln Cys Arg
1               5                   10

<210> SEQ ID NO 201
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: AMIDATION

<400> SEQUENCE: 201

Gly Cys Cys Thr Asp Pro Arg Cys Arg Xaa Gln Cys Phe
1               5                   10

<210> SEQ ID NO 202
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)

```
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: AMIDATION

<400> SEQUENCE: 202

Gly Cys Cys Thr Asp Pro Arg Cys Arg Xaa Gln Cys Tyr
1               5                   10

<210> SEQ ID NO 203
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: AMIDATION

<400> SEQUENCE: 203

Gly Cys Cys Thr Asp Pro Arg Cys Arg Xaa Gln Cys Trp
1               5                   10

<210> SEQ ID NO 204
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: MOD_RES
<222> LOCATION: (13)..(13)
<223> OTHER INFORMATION: D-isomer

<400> SEQUENCE: 204

Gly Cys Cys Ser Asp Pro Arg Cys Arg Tyr Arg Cys Arg
1               5                   10

<210> SEQ ID NO 205
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer

<400> SEQUENCE: 205
```

-continued

```
Gly Cys Cys Ser Asp Pro Arg Cys Arg Xaa Arg Cys Arg
1               5                   10

<210> SEQ ID NO 206
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer

<400> SEQUENCE: 206

Gly Cys Cys Thr Asp Pro Arg Cys Xaa Xaa Gln Cys Arg
1               5                   10

<210> SEQ ID NO 207
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (15)..(15)
<223> OTHER INFORMATION: D-isomer

<400> SEQUENCE: 207

Gly Cys Cys Thr Asp Pro Arg Cys Xaa Xaa Gln Cys Arg Arg Arg
1               5                   10                  15

<210> SEQ ID NO 208
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
```

```
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer

<400> SEQUENCE: 208

Gly Cys Cys Thr Asp Pro Arg Cys Xaa Xaa Gln Cys Tyr
1               5                   10

<210

```
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer

<400> SEQUENCE: 211

Gly Cys Cys Thr Asp Pro Arg Cys Arg Xaa Gln Cys Tyr
1               5                   10

<210> SEQ ID NO 212
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer

<400> SEQUENCE: 212

Gly Cys Cys Thr Asp Pro Arg Cys Arg Xaa Gln Cys Trp
1               5                   10

<210> SEQ ID NO 213
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: MOD_RES
<222> LOCATION: (13)..(13)
<223> OTHER INFORMATION: D-isomer
<220> FEATURE:
<221> NAME/KEY: MOD_RES
<222> LOCATION: (13)..(13)
<223> OTHER INFORMATION: AMIDATION

<400> SEQUENCE: 213

Gly Cys Cys Ser Asp Pro Arg Cys Arg Tyr Arg Cys Arg
1               5                   10

<210> SEQ ID NO 214
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
```

```
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer
<220> FEATURE:
<221> NAME/KEY: MOD_RES
<222> LOCATION: (13)..(13)
<223> OTHER INFORMATION: AMIDATION

<400> SEQUENCE: 214

Gly Cys Cys Ser Asp Pro Arg Cys Arg Xaa Arg Cys Arg
1               5                   10

<210> SEQ ID NO 215
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer
<220> FEATURE:
<221> NAME/KEY: MOD_RES
<222> LOCATION: (13)..(13)
<223> OTHER INFORMATION: AMIDATION

<400> SEQUENCE: 215

Gly Cys Cys Thr Asp Pro Arg Cys Xaa Xaa Gln Cys Arg
1               5                   10

<210> SEQ ID NO 216
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (15)..(15)
<223> OTHER INFORMATION: D-isomer
<220> FEATURE:
<221> NAME/KEY: MOD_RES
<222> LOCATION: (15)..(15)
<223> OTHER INFORMATION: AMIDATION
```

<400> SEQUENCE: 216

Gly Cys Cys Thr Asp Pro Arg Cys Xaa Xaa Gln Cys Arg Arg Arg
1               5                   10                  15

<210> SEQ ID NO 217
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer
<220> FEATURE:
<221> NAME/KEY: MOD_RES
<222> LOCATION: (13)..(13)
<223> OTHER INFORMATION: AMIDATION

<400> SEQUENCE: 217

Gly Cys Cys Thr Asp Pro Arg Cys Xaa Xaa Gln Cys Arg
1               5                   10

<210> SEQ ID NO 218
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (2)..(2)
<223> OTHER INFORMATION: des-Xaa, Arg, or Gln
<220> FEATURE:
<221> NAME/KEY: VARIANT
<222> LOCATION: (8)..(8)
<223> OTHER INFORMATION: des-Xaa, Arg, or Gln
<220> FEATURE:
<221> NAME/KEY: VARIANT
<222> LOCATION: (9)..(9)
<223> OTHER INFORMATION: des-Xaa, Tyr, or mono-iodo-Tyr
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer
<220> FEATURE:
<221> NAME/KEY: MOD_RES
<222> LOCATION: (13)..(13)
<223> OTHER INFORMATION: AMIDATION

<400> SEQUENCE: 218

Gly Xaa Cys Thr Asp Pro Arg Xaa Xaa Xaa Gln Cys Arg
1               5                   10

```
<210> SEQ ID NO 219
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer
<220> FEATURE:
<221> NAME/KEY: MOD_RES
<222> LOCATION: (13)..(13)
<223> OTHER INFORMATION: AMIDATION

<400> SEQUENCE: 219

Gly Cys Cys Thr Asp Pro Arg Cys Arg Xaa Gln Cys Phe
1               5                   10

<210> SEQ ID NO 220
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer
<220> FEATURE:
<221> NAME/KEY: MOD_RES
<222> LOCATION: (13)..(13)
<223> OTHER INFORMATION: AMIDATION

<400> SEQUENCE: 220

Gly Cys Cys Thr Asp Pro Arg Cys Arg Xaa Gln Cys Tyr
1               5                   10

<210> SEQ ID NO 221
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: Acylation
<220> FEATURE:
<221> NAME/KEY: VARIANT
<222> LOCATION: (10)..(10)
<223> OTHER INFORMATION: des-Xaa, Ser, or Thr
<220> FEATURE:
<221> NAME/KEY: MOD_RES
<222> LOCATION: (13)..(13)
<223> OTHER INFORMATION: D-isomer
<220> FEATURE:
```

```
<221> NAME/KEY: MOD_RES
<222> LOCATION: (13)..(13)
<223> OTHER INFORMATION: AMIDATION

<400> SEQUENCE: 221

Gly Cys Cys Thr Asp Pro Arg Cys Arg Xaa Gln Cys Trp
1               5                   10

<210> SEQ ID NO 222
<211> LENGTH: 15
<212> TYPE: PRT
<213> ORGANISM: Artificial sequence
<220> FEATURE:
<223> OTHER INFORMATION: RgIA analog
<220> FEAT -continued

```
<220> FEATURE:
<221> NAME/KEY: MOD_RES
<222> LOCATION: (9)..(9)
<223> OTHER INFORMATION: 7-carboxy-Glu
<220> FEATURE:
<221> NAME/KEY: MOD_RES
<222> LOCATION: (10)..(10)
<223> OTHER INFORMATION: 3-iodo-Tyrosine

<400> SEQUENCE: 225

Gly Cys Cys Thr Asp Pro Arg Cys Xaa Xaa Gln Cys Trp
1               5                   10

<210> SEQ ID NO 226
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: 7-carboxy-Glu
<220> FEATURE:
<221> NAME/KEY: MOD_RES
<222> LOCATION: (10)..(10)
<223> OTHER INFORMATION: 3-iodo-Tyrosine

<400> SEQUENCE: 226

Gly Cys Cys Thr Asp Pro Arg Cys Xaa Xaa Gln Cys Tyr Tyr
1               5                   10

<210> SEQ ID NO 227
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: 7-carboxy-Glu
<220> FEATURE:
<221> NAME/KEY: MOD_RES
<222> LOCATION: (10)..(10)
<223> OTHER INFORMATION: 3-iodo-Tyrosine

<400> SEQUENCE: 227

Gly Cys Cys Thr Asp Pro Arg Cys Xaa Xaa Gln Cys Tyr Arg
1               5                   10

<210> SEQ ID NO 228
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 228

Gly Cys Cys Thr Asp Pro Arg Cys Arg Xaa Gln Cys Arg Arg Arg
1               5                   10                  15

<210> SEQ ID NO 229
<211> LENGTH: 15
<212> TYPE: PRT
<213> ORGANISM: Artificial sequence
<220> FEATURE:
```

```
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 229

Gly Cys Cys Thr Asp Pro Arg Cys Arg Xaa Gln Cys Tyr Arg Arg
1               5                   10                  15

<210> SEQ ID NO 230
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 230

Gly Cys Cys Thr Asp Pro Arg Cys Arg Xaa Gln Cys Arg Arg Tyr
1               5                   10                  15

<210> SEQ ID NO 231
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 231

Gly Cys Cys Thr Asp Pro Arg Cys Arg Xaa Gln Cys Tyr Tyr
1               5                   10

<210> SEQ ID NO 232
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: 3-iodo-Tyrosine

<400> SEQUENCE: 232

Gly Cys Cys Thr Asp Pro Arg Cys Arg Xaa Gln Cys Tyr Arg
1               5                   10

<210> SEQ ID NO 233
<211> LENGTH: 16
<212> TYPE: PRT
<213> ORGANISM: Artificial sequence
<220> FEATURE:
<223> OTHER INFORMATION: RgIA analog

<400> SEQUENCE: 233

Gly Cys Cys Ser Asp Pro Arg Cys Asn Tyr Asp His Pro Glu Ile Cys
1               5                   10                  15

<210> SEQ ID NO 234
<211> LENGTH: 16
<212> TYPE: PRT
```

```
<213> ORGANISM: Artificial sequence
<220> FEATURE:
<223> OTHER INFORMATION: RgIA analog
<220> FEATURE:
<221> NAME/KEY: MOD_RES
<222> LOCATION: (16)..(16)
<223> OTHER INFORMATION: AMIDATION

<400> SEQUENCE: 234

Gly Cys Cys Ser Asp Pro Arg Cys Asn Tyr Asp His Pro Glu Ile Cys
1               5                   10                  15

<210> SEQ ID NO 235
<211> LENGTH: 16
<212> TYPE: PRT
<213> ORGANISM: Artificial sequence
<220> FEATURE:
<223> OTHER INFORMATION: RgIA analog

<400> SEQUENCE: 235

Gly Cys Cys Ser His Pro Ala Cys Ser Val Asn His Pro Glu Leu Cys
1               5                   10                  15

<210> SEQ ID NO 236
<211> LENGTH: 16
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (16)..(16)
<223> OTHER INFORMATION: AMIDATION

<400> SEQUENCE: 236

Gly Cys Cys Ser His Pro Ala Cys Ser Val Asn His Pro Glu Leu Cys
1               5                   10                  15

<210> SEQ ID NO 237
<211> LENGTH: 13
<212> TYPE: PRT
<213> ORGANISM: Artificial sequence
<220> FEATURE:
<223> OTHER INFORMATION: RgIA analog

<400> SEQUENCE: 237

Gly Cys Cys Thr Asp Pro Arg Cys Arg Tyr Arg Cys Arg
1               5                   10

<210> SEQ ID NO 238
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: hydroxy-Pro

<400> SEQUENCE: 238

Gly Cys Cys Ser Asp Xaa Gln Arg Cys Arg Tyr Arg Cys Arg
1               5                   10

<210> SEQ ID NO 239
<211> LENGTH: 13
<212> TYPE: PRT
<213> ORGANISM: Artificial sequence
<220> FEATURE:
```

<223> OTHER INFORMATION: RgIA analog
<220> FEATURE:
<221> NAME/KEY: MOD_RES
<222> LOCATION: (6)..(6)
<223> OTHER INFORMATION: hydroxy-Pro

<400> SEQUENCE: 239

Gly Cys Cys Thr Asp Xaa Arg Cys Arg Tyr Arg Cys Arg
1               5                   10

<210> SEQ ID NO 240
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: mono-halo Tyr

<400> SEQUENCE: 240

Gly Cys Cys Ser Asp Pro Arg Cys Arg Xaa Arg Cys Arg
1               5                   10

<210> SEQ ID NO 241
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (10)..(10)
<223> OTHER INFORMATION: mono-halo Tyr

<400> SEQUENCE: 241

Gly Cys Cys Thr Asp Pro Arg Cys Arg Xaa Arg Cys Arg
1               5                   10

<210> SEQ ID NO 242
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: mono-halo Tyr
<220> FEATURE:
<221> NAME/KEY: MOD_RES
<222> LOCATION: (7)..(7)
<223> OTHER INFORMATION: hydroxy-Pro
<220> FEATURE:
<221> NAME/KEY: MOD_RES
<222> LOCATION: (11)..(11)
<223> OTHER INFORMATION: mono-halo Tyr

<400> SEQUENCE: 242

Xaa Gly Cys Cys Ser Asp Xaa Arg Cys Arg Xaa Arg Cys Arg
1               5                   10

<210> SEQ ID NO 243
<211> LENGTH: 14
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: mono-halo Tyr
<220> FEATURE:
<221> NAME/KEY: MOD_RES
<222> LOCATION: (7)..(7)
<223> OTHER INFORMATION: hydroxy-Pro
<220> FEATURE:
<221> NAME/KEY: MOD_RES
<222> LOCATION: (11)..(11)
<223> OTHER INFORMATION: mono-halo Tyr

<400> SEQUENCE: 243

Xaa Gly Cys Cys Thr Asp Xaa Arg Cys Arg Xaa Arg Cys Arg
1               5                   10

<210> SEQ ID NO 244
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (9)..(9)
<223> OTHER INFORMATION: homo-Arg or ornithine

<400> SEQUENCE: 244

Gly Cys Cys Ser Asp Pro Arg Cys Xaa Tyr Arg Cys Arg
1               5                   10

<210> SEQ ID NO 245
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: 7-carboxy-Glu
<220> FEATURE:
<221> NAME/KEY: MOD_RES
<222> LOCATION: (10)..(10)
<223> OTHER INFORMATION: 3-iodo-Tyrosine

<400> SEQUENCE: 245

Gly Cys Cys Ser Asp Pro Arg Cys Xaa Xaa Arg Cys Arg
1               5                   10

<210> SEQ ID NO 246
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine
<220> FEATURE:
<221> NAME/KEY: MOD_RES
<222> LOCATION: (9)..(9)
<223> OTHER INFORMATION: 7-carboxy-Glu
<220> FEATURE:
<221> NAME/KEY: MOD_RES
<222> LOCATION: (10)..(10)
<223> OTHER INFORMATION: 3-iodo-Tyrosine

<400> SEQUENCE: 246

```
Gly Xaa Cys Thr Asp Pro Arg Xaa Xaa Xaa Gln Cys Lys
1               5                   10
```

<210> SEQ ID NO 247
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: Selenocysteine
<220> FEATURE:
<221> NAME/KEY: MOD_RES
<222> LOCATION: (8)..(8)
<223> OTHER INFORMATION: Selenocysteine

<400> SEQUENCE: 247

```
Gly Xaa Cys Ser Asp Pro Arg Xaa Arg Tyr Arg Cys Arg
1               5                   10
```

<210> SEQ ID NO 248
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<220> FEATURE:
<221> NAME/KEY: MOD_RES
<222> LOCATION: (10)..(10)
<223> OTHER INFORMATION: 3-iodo-Tyrosine

<400> SEQUENCE: 248

```
Gly Cys Cys Thr Asp Pro Arg Cys Xaa Xaa Arg Cys Arg
1               5                   10
```

<210> SEQ ID NO 249
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: 7-carboxy-Glu

<400> SEQUENCE: 249

```
Gly Cys Cys Ser Asp Pro Arg Cys Xaa Tyr Arg Cys Arg
1               5                   10
```

<210> SEQ ID NO 250
<211> LENGTH: 13
<212> TYPE: PRT
<213> ORGANISM: Artificial sequence
<220> FEATURE:
<223> OTHER INFORMATION: RgIA analog

<400> SEQUENCE: 250

```
Gly Cys Cys Ser Asp Pro Arg Cys Arg Tyr Gln Cys Arg
1               5                   10
```

<210> SEQ ID NO 251
<211> LENGTH: 13
<212> TYPE: PRT

```
<213> ORGANISM: Artificial sequence
<220> FEATURE:
<223> OTHER INFORMATION: RgIA analog

<400> SEQUENCE: 251

Gly Cys Cys Ser Asp Pro Arg Cys Phe Trp Arg Cys Arg
1               5                   10

<210> SEQ ID NO 252
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: homocysteine

<400> SEQUENCE: 252

Gly Xaa Cys Ser Asp Pro Arg Cys Arg Tyr Arg Cys Arg
1               5                   10

<210> SEQ ID NO 253
<211> LENGTH: 13
<212> TYPE: PRT
<213> ORGANISM: Artificial sequence
<220> FEATURE:
<223> OTHER INFORMATION: RgIA analog

<400> SEQUENCE: 253

Gly Cys Cys Ala Asp Pro Arg Cys Arg Tyr Arg Cys Arg
1               5                   10

<210> SEQ ID NO 254
<211> LENGTH: 13
<212> TYPE: PRT
<213> ORGANISM: Artificial sequence
<220> FEATURE:
<223> OTHER INFORMATION: RgIA analog

<400> SEQUENCE: 254

Gly Cys Cys Tyr Asp Pro Arg Cys Arg Tyr Arg Cys Arg
1               5                   10

<210> SEQ ID NO 255
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (8)..(8)
<223> OTHER INFORMATION: homocysteine

<400> SEQUENCE: 255

Gly Cys Cys Ser Asp Pro Arg Xaa Arg Tyr Arg Cys Arg
1               5                   10

<210> SEQ ID NO 256
<211> LENGTH: 13
<212> TYPE: PRT
<213> ORGANISM: Artificial sequence
<220> FEATURE:
<223> OTHER INFORMATION: RgIA analog

<400> SEQUENCE: 256
```

Gly Cys Cys Ser Asp Pro Arg Cys Gly Tyr Arg Cys Arg
1               5                   10

<210> SEQ ID NO 257
<211> LENGTH: 13
<212> TYPE: PRT
<213> ORGANISM: Artificial sequence
<220> FEATURE:
<223> OTHER INFORMATION: RgIA analog

<400> SEQUENCE: 257

Gly Cys Cys Ser Asp Pro Arg Cys Ala Tyr Arg Cys Arg
1               5                   10

<210> SEQ ID NO 258
<211> LENGTH: 13
<212> TYPE: PRT
<213> ORGANISM: Artificial sequence
<220> FEATURE:
<223> OTHER INFORMATION: RgIA analog

<400> SEQUENCE: 258

Gly Cys Cys Ser Asp Pro Arg Cys Val Tyr Arg Cys Arg
1               5                   10

<210> SEQ ID NO 259
<211> LENGTH: 13
<212> TYPE: PRT
<213> ORGANISM: Artificial sequence
<220> FEATURE:
<223> OTHER INFORMATION: RgIA analog

<400> SEQUENCE: 259

Gly Cys Cys Ser Asp Pro Arg Cys Leu Tyr Arg Cys Arg
1               5                   10

<210> SEQ ID NO 260
<211> LENGTH: 13
<212> TYPE: PRT
<213> ORGANISM: Artificial sequence
<220> FEATURE:
<223> OTHER INFORMATION: RgIA analog

<400> SEQUENCE: 260

Gly Cys Cys Ser Asp Pro Arg Cys Ile Tyr Arg Cys Arg
1               5                   10

<210> SEQ ID NO 261
<211> LENGTH: 13
<212> TYPE: PRT
<213> ORGANISM: Artificial sequence
<220> FEATURE:
<223> OTHER INFORMATION: RgIA analog

<400> SEQUENCE: 261

Gly Cys Cys Ser Asp Pro Arg Cys Met Tyr Arg Cys Arg
1               5                   10

<210> SEQ ID NO 262
<211> LENGTH: 13
<212> TYPE: PRT
<213> ORGANISM: Artificial sequence
<220> FEATURE:
<223> OTHER INFORMATION: RgIA analog

<400> SEQUENCE: 262

Gly Cys Cys Ser Asp Pro Arg Cys Phe Tyr Arg Cys Arg

-continued 1 5 10

<210> SEQ ID NO 263
<211> LENGTH: 13
<212> TYPE: PRT
<213> ORGANISM: Artificial sequence
<220> FEATURE:
<223> OTHER INFORMATION: RgIA analog

<400> SEQUENCE: 263

Gly Cys Cys Ser Asp Pro Arg Cys Trp Tyr Arg Cys Arg
1 5 10

<210> SEQ ID NO 264
<211> LENGTH: 13
<212> TYPE: PRT
<213> ORGANISM: Artificial sequence
<220> FEATURE:
<223> OTHER INFORMATION: RgIA analog

<400> SEQUENCE: 264

Gly Cys Cys Ser Asp Pro Arg Cys Pro Tyr Arg Cys Arg
1 5 10

<210> SEQ ID NO 265
<211> LENGTH: 13
<212> TYPE: PRT
<213> ORGANISM: Artificial sequence
<220> FEATURE:
<223> OTHER INFORMATION: RgIA analog

<400> SEQUENCE: 265

Gly Cys Cys Ser Asp Pro Arg Cys Ser Tyr Arg Cys Arg
1 5 10

<210> SEQ ID NO 266
<211> LENGTH: 13
<212> TYPE: PRT
<213> ORGANISM: Artificial sequence
<220> FEATURE:
<223> OTHER INFORMATION: RgIA analog

<400> SEQUENCE: 266

Gly Cys Cys Ser Asp Pro Arg Cys Thr Tyr Arg Cys Arg
1 5 10

<210> SEQ ID NO 267
<211> LENGTH: 13
<212> TYPE: PRT
<213> ORGANISM: Artificial sequence
<220> FEATURE:
<223> OTHER INFORMATION: RgIA analog

<400> SEQUENCE: 267

Gly Cys Cys Ser Asp Pro Arg Cys Cys Tyr Arg Cys Arg
1 5 10

<210> SEQ ID NO 268
<211> LENGTH: 13
<212> TYPE: PRT
<213> ORGANISM: Artificial sequence
<220> FEATURE:
<223> OTHER INFORMATION: RgIA analog

<400> SEQUENCE: 268

Gly Cys Cys Ser Asp Pro Arg Cys Tyr Tyr Arg Cys Arg
1 5 10

```
<210> SEQ ID NO 269
<211> LENGTH: 13
<212> TYPE: PRT
<213> ORGANISM: Artificial sequence
<220> FEATURE:
<223> OTHER INFORMATION: RgIA analog

<400> SEQUENCE: 269

Gly Cys Cys Ser Asp Pro Arg Cys Asn Tyr Arg Cys Arg
1               5                   10

<210> SEQ ID NO 270
<211> LENGTH: 13
<212> TYPE: PRT
<213> ORGANISM: Artificial sequence
<220> FEATURE:
<223> OTHER INFORMATION: RgIA analog

<400> SEQUENCE: 270

Gly Cys Cys Ser Asp Pro Arg Cys Gln Tyr Arg Cys Arg
1               5                   10

<210> SEQ ID NO 271
<211> LENGTH: 13
<212> TYPE: PRT
<213> ORGANISM: Artificial sequence
<220> FEATURE:
<223> OTHER INFORMATION: RgIA analog

<400> SEQUENCE: 271

Gly Cys Cys Ser Asp Pro Arg Cys Asp Tyr Arg Cys Arg
1               5                   10

<210> SEQ ID NO 272
<211> LENGTH: 13
<212> TYPE: PRT
<213> ORGANISM: Artificial sequence
<220> FEATURE:
<223> OTHER INFORMATION: RgIA analog

<400> SEQUENCE: 272

Gly Cys Cys Ser Asp Pro Arg Cys Glu Tyr Arg Cys Arg
1               5                   10

<210> SEQ ID NO 273
<211> LENGTH: 13
<212> TYPE: PRT
<213> ORGANISM: Artificial sequence
<220> FEATURE:
<223> OTHER INFORMATION: RgIA analog

<400> SEQUENCE: 273

Gly Cys Cys Ser Asp Pro Arg Cys Lys Tyr Arg Cys Arg
1               5                   10

<210> SEQ ID NO 274
<211> LENGTH: 13
<212> TYPE: PRT
<213> ORGANISM: Artificial sequence
<220> FEATURE:
<223> OTHER INFORMATION: RgIA analog

<400> SEQUENCE: 274

Gly Cys Cys Ser Asp Pro Arg Cys His Tyr Arg Cys Arg
1               5                   10
```

<210> SEQ ID NO 275
<211> LENGTH: 13
<212> TYPE: PRT
<213> ORGANISM: Artificial sequence
<220> FEATURE:
<223> OTHER INFORMATION: RgIA analog

<400> SEQUENCE: 275

Gly Cys Cys Ser Asp Pro Arg Cys Arg Phe Arg Cys Arg
1               5                   10

<210> SEQ ID NO 276
<211> LENGTH: 13
<212> TYPE: PRT
<213> ORGANISM: Artificial sequence
<220> FEATURE:
<223> OTHER INFORMATION: RgIA analog

<400> SEQUENCE: 276

Gly Cys Cys Ser Asp Pro Arg Cys Arg Tyr His Cys Arg
1               5                   10

<210> SEQ ID NO 277
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (9)..(9)
<223> OTHER INFORMATION: omega-nitro-Arg
<220> FEATURE:
<221> NAME/KEY: MOD_RES
<222> LOCATION: (10)..(10)
<223> OTHER INFORMATION: 3-iodo-Tyrosine

<400> SEQUENCE: 277

Gly Cys Cys Ser Asp Pro Arg Cys Xaa Xaa Arg Cys Arg
1               5                   10

<210> SEQ ID NO 278
<211> LENGTH: 12
<212> TYPE: PRT
<213> ORGANISM: Artificial sequence
<220> FEATURE:
<223> OTHER INFORMATION: RgIA analog

<400> SEQUENCE: 278

Gly Cys Cys Ser Asp Pro Arg Cys Arg Tyr Arg Cys
1               5                   10

<210> SEQ ID NO 279
<211> LENGTH: 13
<212> TYPE: PRT
<213> ORGANISM: Artificial sequence
<220> FEATURE:
<223> OTHER INFORMATION: RgIA analog

<400> SEQUENCE: 279

Gly Cys Cys Ser Glu Pro Arg Cys Arg Tyr Arg Cys Arg
1               5                   10

<210> SEQ ID NO 280
<211> LENGTH: 13
<212> TYPE: PRT
<213> ORGANISM: Artificial sequence
<220> FEATURE:

<223> OTHER INFORMATION: RgIA analog

<400> SEQUENCE: 280

Gly Cys Cys Ser Asp Val Arg Cys Arg Tyr Ar

Arg Cys Gly
        35

<210> SEQ ID NO 286
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: mono-halo Tyr
<220> FEATURE:
<221> NAME/KEY: MOD_RES
<222> LOCATION: (6)..(6)
<223> OTHER INFORMATION: hydroxy-Pro
<220> FEATURE:
<221> NAME/KEY: MOD_RES
<222> LOCATION: (10)..(10)
<223> OTHER INFORMATION: mono-halo Tyr

<400> SEQUENCE: 286

Xaa Gly Cys Cys Ser Xaa Arg Cys Arg Xaa Arg Cys Arg
1               5                   10

<210> SEQ ID NO 287
<211> LENGTH: 32
<212> TYPE: PRT
<213> ORGANISM: Artificial sequence
<220> FEATURE:
<223> OTHER INFORMATION: RgIA analog

<400> SEQUENCE: 287

Ser Asn Lys Arg Lys Asn Ala Ala Met Leu Asp Met Ile Ala Gln His
1               5                   10                  15

Ala Ile Arg Gly Cys Cys Ser Asp Pro Arg Cys Arg Tyr Arg Cys Arg
            20                  25                  30

<210> SEQ ID NO 288
<211> LENGTH: 16
<212> TYPE: PRT
<213> ORGANISM: Artificial sequence
<220> FEATURE:
<223> OTHER INFORMATION: RgIA analog

<400> SEQUENCE: 288

Asp Glu Cys Cys Ser Asn Pro Ala Cys Arg Val Asn Asn Pro His Val
1               5                   10                  15

<210> SEQ ID NO 289
<211> LENGTH: 39
<212> TYPE: PRT
<213> ORGANISM: Artificial sequence
<220> FEATURE:
<223> OTHER INFORMATION: RgIA analog

<400> SEQUENCE: 289

Ser Asp Gly Arg Asn Val Ala Ala Lys Ala Phe His Arg Ile Gly Arg
1               5                   10                  15

Thr Ile Arg Asp Glu Cys Cys Ser Asn Pro Ala Cys Arg Val Asn Asn
            20                  25                  30

Pro His Val Cys Arg Arg Arg
        35

<210> SEQ ID NO 290
<211> LENGTH: 20

```
<212> TYPE: PRT
<213> ORGANISM: Artificial sequence
<220> FEATURE:
<223> OTHER INFORMATION: RgIA analog

<400> SEQUENCE: 290

Asp Glu Cys Cys Ser Asn Pro Ala Cys Arg Leu Asn Asn Pro His Ala
1               5                   10                  15

Cys Arg Arg Arg
            20

<210> SEQ ID NO 291
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: gamma-carboxy-Glu (Gla)

<400> SEQUENCE: 291

Asp Xaa Cys Cys Ser Asn Pro Ala Cys Arg Leu Asn Asn Pro His Ala
1               5                   10                  15

Cys Arg Arg Arg
            20

<210> SEQ ID NO 292
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (7)..(7)
<223> OTHER INFORMATION: hydroxy-Pro

<400> SEQUENCE: 292

Asp Glu Cys Cys Ser Asn Xaa Ala Cys Arg Leu Asn Asn Pro His Ala
1               5                   10                  15

Cys Arg Arg Arg
            20

<210> SEQ ID NO 293
<211> LENGTH: 21
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: gamma-carboxy-Glu (Gla)
<220> FEATURE:
<221> NAME/KEY: MOD_RES
<222> LOCATION: (3)..(3)
<223> OTHER INFORMATION: gamma-carboxy-Glu (Gla)
<220> FEATURE:
<221> NAME/KEY: MOD_RES
<222> LOCATION: (8)..(8)
<223> OTHER INFORMATION: hydroxy-Pro

<400> SEQUENCE: 293

Xaa Asp Xaa Cys Cys Ser Asn Xaa Ala Cys Arg Leu Asn Asn Pro His
1               5                   10                  15

Ala Cys Arg Arg Arg
```

-continued

```
                20

<210> SEQ ID NO 294
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (14)..(14)
<223> OTHER INFORMATION: hydroxy-Pro

<400> SEQUENCE: 294

Asp Glu Cys Cys Ser Asn Pro Ala Cys Arg Leu Asn Asn Xaa His Ala
1               5                   10                  15

Cys Arg Arg Arg
            20

<210> SEQ ID NO 295
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: gamma-carboxy-Glu (Gla)
<220> FEATURE:
<221> NAME/KEY: MOD_RES
<222> LOCATION: (3)..(3)
<223> OTHER INFORMATION: gamma-carboxy-Glu (Gla)
<220> FEATURE:
<221> NAME/KEY: MOD_RES
<222> LOCATION: (14)..(14)
<223> OTHER INFORMATION: hydroxy-Pro

<400> SEQUENCE: 295

Xaa Asp Xaa Cys Cys Ser Asn Pro Ala Cys Arg Leu Asn Xaa His Ala
1               5                   10                  15

Cys Arg Arg Arg
            20

<210> SEQ ID NO 296
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (7)..(7)
<223> OTHER INFORMATION: hydroxy-Pro
<220> FEATURE:
<221> NAME/KEY: MOD_RES
<222> LOCATION: (14)..(14)
<223> OTHER INFORMATION: hydroxy-Pro

<400> SEQUENCE: 296

Asp Glu Cys Cys Ser Asn Xaa Ala Cys Arg Leu Asn Asn Xaa His Ala
1               5                   10                  15

Cys Arg Arg Arg
            20

<210> SEQ ID NO 297
<211> LENGTH: 21
<212> TYPE: PRT
<213> ORGANISM: Artificial sequence
```

```
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: gamma-carboxy-Glu (Gla)
<220> FEATURE:
<221> NAME/KEY: MOD_RES
<222> LOCATION: (3)..(3)
<223> OTHER INFORMATION: gamma-carboxy-Glu (Gla)
<220> FEATURE:
<221> NAME/KEY: MOD_RES
<222> LOCATION: (8)..(8)
<223> OTHER INFORMATION: hydroxy-Pro
<220> FEATURE:
<221> NAME/KEY: MOD_RES
<222> LOCATION: (15)..(15)
<223> OTHER INFORMATION: hydroxy-Pro

<400> SEQUENCE: 297

Xaa Asp Xaa Cys Cys Ser Asn Xaa Ala Cys Arg Leu Asn Asn Xaa His
1               5                   10                  15

Ala Cys Arg Arg Arg
            20

<210> SEQ ID NO 298
<211> LENGTH: 20
<212> TYPE: PRT
<213> ORGANISM: Artificial sequence
<220> FEATURE:
<223> OTHER INFORMATION: RgIA analog

<400> SEQUENCE: 298

Asp Glu Cys Cys Ser Asn Pro Ala Cys Arg Leu Asn Asn Pro His Val
1               5                   10                  15

Cys Arg Arg Arg
            20

<210> SEQ ID NO 299
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (2)..(2)
<223> OTHER INFORMATION: gamma-carboxy-Glu (Gla)

<400> SEQUENCE: 299

Asp Xaa Cys Cys Ser Asn Pro Ala Cys Arg Leu Asn Asn Pro His Val
1               5                   10                  15

Cys Arg Arg Arg
            20

<210> SEQ ID NO 300
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (7)..(7)
<223> OTHER INFORMATION: gamma-carboxy-Glu (Gla)

<400> SEQUENCE: 300

Asp Glu Cys Cys Ser Asn Xaa Ala Cys Arg Leu Asn Asn Pro His Val
1               5                   10                  15
```

Cys Arg Arg Arg
            20

<210> SEQ ID NO 301
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: gamma-carboxy-Glu (Gla)
<220> FEATURE:
<221> NAME/KEY: MOD_RES
<222> LOCATION: (3)..(3)
<223> OTHER INFORMATION: gamma-carboxy-Glu (Gla)
<220> FEATURE:
<221> NAME/KEY: MOD_RES
<222> LOCATION: (8)..(8)
<223> OTHER INFORMATION: hydroxy-Pro

<400> SEQUENCE: 301

Xaa Asp Xaa Cys Cys Ser Asn Xaa Ala Cys Arg Leu Asn Pro His Val
1               5                   10                  15

Cys Arg Arg Arg
            20

<210> SEQ ID NO 302
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (14)..(14)
<223> OTHER INFORMATION: hydroxy-Pro

<400> SEQUENCE: 302

Asp Glu Cys Cys Ser Asn Pro Ala Cys Arg Leu Asn Asn Xaa His Val
1               5                   10                  15

Cys Arg Arg Arg
            20

<210> SEQ ID NO 303
<211> LENGTH: 21
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: gamma-carboxy-Glu (Gla)
<220> FEATURE:
<221> NAME/KEY: MOD_RES
<222> LOCATION: (3)..(3)
<223> OTHER INFORMATION: gamma-carboxy-Glu (Gla)
<220> FEATURE:
<221> NAME/KEY: MOD_RES
<222> LOCATION: (8)..(8)
<223> OTHER INFORMATION: hydroxy-Pro

<400> SEQUENCE: 303

Xaa Asp Xaa Cys Cys Ser Asn Xaa Ala Cys Arg Leu Asn Asn Pro His
1               5                   10                  15

Val Cys Arg Arg Arg
            20

```
<210> SEQ ID NO 304
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (7)..(7)
<223> OTHER INFORMATION: hydroxy-Pro
<220> FEATURE:
<221> NAME/KEY: MOD_RES
<222> LOCATION: (14)..(14)
<223> OTHER INFORMATION: hydroxy-Pro

<400> SEQUENCE: 304

Asp Glu Cys Cys Ser Asn Xaa Ala Cys Arg Leu Asn Asn Xaa His Val
1               5                   10                  15

Cys Arg Arg Arg
            20

<210> SEQ ID NO 305
<211> LENGTH: 21
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: gamma-carboxy-Glu (Gla)
<220> FEATURE:
<221> NAME/KEY: MOD_RES
<222> LOCATION: (3)..(3)
<223> OTHER INFORMATION: gamma-carboxy-Glu (Gla)
<220> FEATURE:
<221> NAME/KEY: MOD_RES
<222> LOCATION: (8)..(8)
<223> OTHER INFORMATION: hydroxy-Pro
<220> FEATURE:
<221> NAME/KEY: MOD_RES
<222> LOCATION: (15)..(15)
<223> OTHER INFORMATION: hydroxy-Pro

<400> SEQUENCE: 305

Xaa Asp Xaa Cys Cys Ser Asn Xaa Ala Cys Arg Leu Asn Asn Xaa His
1               5                   10                  15

Val Cys Arg Arg Arg
            20

<210> SEQ ID NO 306
<211> LENGTH: 16
<212> TYPE: PRT
<213> ORGANISM: Artificial sequence
<220> FEATURE:
<223> OTHER INFORMATION: RgIA analog

<400> SEQUENCE: 306

Gly Cys Cys Ser His Pro Ala Cys Asn Val Asp His Pro Glu Ile Cys
1               5                   10                  15

<210> SEQ ID NO 307
<211> LENGTH: 64
<212> TYPE: PRT
<213> ORGANISM: Artificial sequence
<220> FEATURE:
<223> OTHER INFORMATION: RgIA analog

<400> SEQUENCE: 307
```

```
Met Phe Thr Val Phe Leu Leu Val Val Leu Ala Thr Thr Val Val Ser
1               5                   10                  15

Phe Thr Ser Asp Arg Ala Phe Arg Gly Arg Asn Ser Ala Ala Asn Asp
                20                  25                  30

Lys Arg Ser Asp Leu Ala Ala Leu Ser Val Arg Gly Cys Cys Ser
                35                  40                  45

His Pro Ala Cys Ser Val Asn His Pro Glu Leu Cys Gly Arg Arg
    50                  55                  60
```

<210> SEQ ID NO 308
<211> LENGTH: 21
<212> TYPE: PRT
<213> ORGANISM: Artificial sequence
<220> FEATURE:
<223> OTHER INFORMATION: RgIA analog

<400> SEQUENCE: 308

```
Glu Cys Cys Thr Asn Pro Val Cys His Ala Glu His Gln His Glu Leu
1               5                   10                  15

Cys Ala Arg Arg Arg
                20
```

<210> SEQ ID NO 309
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (11)..(11)
<223> OTHER INFORMATION: 7-carboxy-Glu

<400> SEQUENCE: 309

```
Glu Cys Cys Thr Asn Pro Val Cys His Ala Xaa His Gln Glu Leu Cys
1               5                   10                  15

Ala Arg Arg Arg
                20
```

<210> SEQ ID NO 310
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (11)..(11)
<223> OTHER INFORMATION: 7-carboxy-Glu
<220> FEATURE:
<221> NAME/KEY: MOD_RES
<222> LOCATION: (14)..(14)
<223> OTHER INFORMATION: 7-carboxy-Glu

<400> SEQUENCE: 310

```
Glu Cys Cys Thr Asn Pro Val Cys His Ala Xaa His Gln Xaa Leu Cys
1               5                   10                  15

Ala Arg Arg Arg
                20
```

<210> SEQ ID NO 311
<211> LENGTH: 20
<212> TYPE: PRT
<213> ORGANISM: Artificial sequence
<220> FEATURE:

```
<223> OTHER INFORMATION: RgIA analog
<220> FEATURE:
<221> NAME/KEY: MOD_RES
<222> LOCATION: (11)..(11)
<223> OTHER INFORMATION: 3-iodo-Tyrosine
<220> FEATURE:
<221> NAME/KEY: MOD_RES
<222> LOCATION: (14)..(14)
<223> OTHER INFORMATION: 7-carboxy-Glu

<400> SEQUENCE: 311

Glu Cys Cys Thr Asn Pro Val Cys His Ala Xaa His Gln Xaa Leu Cys
1               5                   10                  15

Ala Arg Arg Arg
        20

<210> SEQ ID NO 312
<211> LENGTH: 21
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: 7-carboxy-Glu

<400> SEQUENCE: 312

Xaa Cys Cys Thr Asn Pro Val Cys His Ala Glu His Gln His Glu Leu
1               5                   10                  15

Cys Ala Arg Arg Arg
        20

<210> SEQ ID NO 313
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: 7-carboxy-Glu
<220> FEATURE:
<221> NAME/KEY: MOD_RES
<222> LOCATION: (11)..(11)
<223> OTHER INFORMATION: 7-carboxy-Glu

<400> SEQUENCE: 313

Xaa Cys Cys Thr Asn Pro Val Cys His Ala Xaa His Gln Glu Leu Cys
1               5                   10                  15

Ala Arg Arg Arg
        20

<210> SEQ ID NO 314
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: 7-carboxy-Glu
<220> FEATURE:
<221> NAME/KEY: MOD_RES
<222> LOCATION: (11)..(11)
<223> OTHER INFORMATION: 7-carboxy-Glu
<220> FEATURE:
<221> NAME/KEY: MOD_RES
```

```
<222> LOCATION: (14)..(14)
<223> OTHER INFORMATION: 7-carboxy-Glu

<400> SEQUENCE: 314

Xaa Cys Cys Thr Asn Pro Val Cys His Ala Xaa His Gln Xaa Leu Cys
1               5                   10                  15

Ala Arg Arg Arg
            20

<210> SEQ ID NO 315
<211> LENGTH: 20
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (1)..(1)
<223> OTHER INFORMATION: 7-carboxy-Glu
<220> FEATURE:
<221> NAME/KEY: MOD_RES
<222> LOCATION: (11)..(11)
<223> OTHER INFORMATION: 3-iodo-Tyrosine
<220> FEATURE:
<221> NAME/KEY: MOD_RES
<222> LOCATION: (14)..(14)
<223> OTHER INFORMATION: 7-carboxy-Glu

<400> SEQUENCE: 315

Xaa Cys Cys Thr Asn Pro Val Cys His Ala Xaa His Gln Xaa Leu Cys
1               5                   10                  15

Ala Arg Arg Arg
            20

<210> SEQ ID NO 316
<211> LENGTH: 15
<212> TYPE: PRT
<213> ORGANISM: Artificial sequence
<220> FEATURE:
<223> OTHER INFORMATION: RgIA analog

<400> SEQUENCE: 316

Gly Cys Cys Ser His Pro Val Cys Ser Ala Met Ser Pro Ile Cys
1               5                   10                  15

<210> SEQ ID NO 317
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: VARIANT
<222> LOCATION: (13)..(13)
<223> OTHER INFORMATION: des-Xaa, Arg, or citrulline

<400> SEQUENCE: 317

Gly Cys Cys Ser His Pro Val Cys Ser Ala Met Ser Xaa Ile Cys
1               5                   10                  15

<210> SEQ ID NO 318
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
```

```
<223> OTHER INFORMATION: hydroxy-Pro
<220> FEATURE:
<221> NAME/KEY: VARIANT
<222> LOCATION: (13)..(13)
<223> OTHER INFORMATION: des-Xaa, Arg, or citrulline

<400> SEQUENCE: 318

Gly Cys Cys Ser His Xaa Val Cys Ser Ala Met Ser Xaa Ile Cys
1               5                   10                  15

<210> SEQ ID NO 319
<211> LENGTH: 15
<212> TYPE: PRT
<213> ORGANISM: Artificial sequence
<220> FEATURE:
<223> OTHER INFORMATION: RgIA analog
<220> FEATURE:
<221> NAME/KEY: MOD_RES
<222> LOCATION: (6)..(6)
<223> OTHER INFORMATION: hydroxy-Pro

<400> SEQUENCE: 319

Gly Cys Cys Ser His Xaa Val Cys Ser Ala Met Ser Pro Ile Cys
1               5                   10                  15

<210> SEQ ID NO 320
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MISC_FEATURE
<222> LOCATION: (2)..(8)
<223> OTHER INFORMATION: Amino acid at position 2 and amino acid at
      position 8 form a bridge
<220> FEATURE:
<221> NAME/KEY: MISC_FEATURE
<222> LOCATION: (3)..(12)
<223> OTHER INFORMATION: Amino acid at position 3 and amino acid at
      position 12 form a bridge
<220> FEATURE:
<221> NAME/KEY: VARIANT
<222> LOCATION: (2)..(2)
<223> OTHER INFORMATION: Any natural amino acid, or any unnatural amino
      acid
<220> FEATURE:
<221> NAME/KEY: VARIANT
<222> LOCATION: (3)..(3)
<223> OTHER INFORMATION: Any natural amino acid, or any unnatural amino
      acid
<220> FEATURE:
<221> NAME/KEY: VARIANT
<222> LOCATION: (8)..(8)
<223> OTHER INFORMATION: Any natural amino acid, or any unnatural amino
      acid
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: VARIANT
<222> LOCATION: (12)..(12)
<223> OTHER INFORMATION: Any natural amino acid, or any unnatural amino
      acid
<220> FEATURE:
<221> NAME/KEY: MOD_RES
<222> LOCATION: (13)..(13)
<223> OTHER INFORMATION: AMIDATION

<400> SEQUENCE: 320
```

```
Gly Xaa Xaa Thr Asp Pro Arg Xaa Xaa Xaa Gln Xaa Tyr
1               5                   10

<210> SEQ ID NO 321
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MISC_FEATURE
<222> LOCATION: (2)..(12)
<223> OTHER INFORMATION: Amino acid at position 2 and amino acid at
      position 12 form a bridge
<220> FEATURE:
<221> NAME/KEY: MISC_FEATURE
<222> LOCATION: (3)..(8)
<223> OTHER INFORMATION: Amino acid at position 3 and amino acid at
      position 8 form a bridge
<220> FEATURE:
<221> NAME/KEY: VARIANT
<222> LOCATION: (2)..(2)
<223> OTHER INFORMATION: Any natural amino acid, or any unnatural amino
      acid
<220> FEATURE:
<221> NAME/KEY: VARIANT
<222> LOCATION: (3)..(3)
<223> OTHER INFORMATION: Any natural amino acid, or any unnatural amino
      acid
<220> FEATURE:
<221> NAME/KEY: VARIANT
<222> LOCATION: (8)..(8)
<223> OTHER INFORMATION: Any natural amino acid, or any unnatural amino
      acid
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: VARIANT
<222> LOCATION: (12)..(12)
<223> OTHER INFORMATION: Any natural amino acid, or any unnatural amino
      acid
<220> FEATURE:
<221> NAME/KEY: MOD_RES
<222> LOCATION: (13)..(13)
<223> OTHER INFORMATION: AMIDATION

<400> SEQUENCE: 321

Gly Xaa Xaa Thr Asp Pro Arg Xaa Xaa Xaa Gln Xaa Tyr
1               5                   10

<210> SEQ ID NO 322
<211> LENGTH: 13
<212> TYPE: PRT
<213> ORGANISM: Artificial sequence
<220> FEATURE:
<223> OTHER INFORMATION: RgIA analog
<220> FEATURE:
<221> NAME/KEY: MISC_FEATURE
<222> LOCATION: (2)..(3)
<223> OTHER INFORMATION: Amino acid at position 2 and amino acid at
      position 3 form a bridge
<220> FEATURE:
<221> NAME/KEY: MISC_FEATURE
<222> LOCATION: (8)..(12)
<223> OTHER INFORMATION: Amino acid at position 8 and amino acid at
      position 12 form a bridge
<220> FEATURE:
<221> NAME/KEY: VARIANT
<222> LOCATION: (2)..(2)
```

```
<223> OTHER INFORMATION: Any natural amino acid, or any unnatural amino
      acid
<220> FEATURE:
<221> NAME/KEY: VARIANT
<222> LOCATION: (3)..(3)
<223> OTHER INFORMATION: Any natural amino acid, or any unnatural amino
      acid
<220> FEATURE:
<221> NAME/KEY: VARIANT
<222> LOCATION: (8)..(8)
<223> OTHER INFORMATION: Any natural amino acid, or any unnatural amino
      acid
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: VARIANT
<222> LOCATION: (12)..(12)
<223> OTHER INFORMATION: Any natural amino acid, or any unnatural amino
      acid
<220> FEATURE:
<221> NAME/KEY: MOD_RES
<222> LOCATION: (13)..(13)
<223> OTHER INFORMATION: AMIDATION

<400> SEQUENCE: 322

Gly Xaa Xaa Thr Asp Pro Arg Xaa Xaa Xaa Gln Xaa Tyr
1               5                   10

<210> SEQ ID NO 323
<211> LENGTH: 13
<212> TYPE: PRT
<213> ORGANISM: Artificial sequence
<220> FEATURE:
<223> OTHER INFORMATION: RgIA analog with a lactam bridge between
      position 2 and position 8
<220> FEATURE:
<221> NAME/KEY: DISULFID
<222> LOCATION: (3)..(12)
<220> FEATURE:
<221> NAME/KEY: MISC_FEATURE
<222> LOCATION: (2)..(8)
<223> OTHER INFORMATION: Amino acid at position 2 and amino acid at
      position 8 form a lactam bridge
<220> FEATURE:
<221> NAME/KEY: VARIANT
<222> LOCATION: (2)..(2)
<223> OTHER INFORMATION: Glu or Lys
<220> FEATURE:
<221> NAME/KEY: VARIANT
<222> LOCATION: (8)..(8)
<223> OTHER INFORMATION: Glu or Lys
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 323

Gly Xaa Cys Thr Asp Pro Arg Xaa Xaa Xaa Gln Cys Tyr
1               5                   10

<210> SEQ ID NO 324
```

```
<211> LENGTH: 13
<212> TYPE: PRT
<213> ORGANISM: Artificial sequence
<220> FEATURE:
<223> OTHER INFORMATION: RgIA analog with a lactam bridge between
      position 3 and position 12
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: Amino acid at position 3 and amino acid at
      position 12 form a lactam bridge
<220> FEATURE:
<221> NAME/KEY: VARIANT
<222> LOCATION: (3)..(3)
<223> OTHER INFORMATION: Glu or Lys
<220> FEATURE:
<221> NAME/KEY: VARIANT
<222> LOCATION: (12)..(12)
<223> OTHER INFORMATION: Glu or Lys
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 324

Gly Cys Xaa Thr Asp Pro Arg Cys Xaa Xaa Gln Xaa Tyr
1               5                   10

<210> SEQ ID NO 325
<211> LENGTH: 13
<212> TYPE: PRT
<213> ORGANISM: Artificial sequence
<220> FEATURE:
<223> OTHER INFORMATION: RgIA analog with Lactam bridge #1
<220> FEATURE:
<221> NAME/KEY: DISULFID
<222> LOCATION: (3)..(12)
<220> FEATURE:
<221> NAME/KEY: MISC_FEATURE
<222> LOCATION: (2)..(8)
<223> OTHER INFORMATION: Glu at position 2 and Lys at position 8 form a
      lactam bridge
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 325

Gly Glu Cys Thr Asp Pro Arg Lys Xaa Xaa Gln Cys Tyr
1               5                   10

<210> SEQ ID NO 326
<211> LENGTH: 13
<212> TYPE: PRT
<213> ORGANISM: Artificial sequence
<220> FEATURE:
```

```
<223> OTHER INFORMATION: RgIA analog with Lactam bridge #2
<220> FEATURE:
<221> NAME/KEY: DISULFID
<222> LOCATION: (3)..(12)
<220> FEATURE:
<221> NAME/KEY: MISC_FEATURE
<222> LOCATION: (2)..(8)
<223> OTHER INFORMATION: Lys at position 2 and Glu at position 8 form a
      lactam bridge
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 326

Gly Lys Cys Thr Asp Pro Arg Glu Xaa Xaa Gln Cys Tyr
1               5                   10

<210> SEQ ID NO 327
<211> LENGTH: 13
<212> TYPE: PRT
<213> ORGANISM: Artificial sequence
<220> FEATURE:
<223> OTHER INFORMATION: RgIA analog with Lactam bridge #3
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: Glu at position 3 and Lys at position 12 form a
      lactam bridge
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 327

Gly Cys Glu Thr Asp Pro Arg Cys Xaa Xaa Gln Lys Tyr
1               5                   10

<210> SEQ ID NO 328
<211> LENGTH: 13
<212> TYPE: PRT
<213> ORGANISM: Artificial sequence
<220> FEATURE:
<223> OTHER INFORMATION: RgIA analog with Lactam bridge #4
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: Lys at position 3 and Glu at position 12 form a
      lactam bridge
<220> FEATURE:
<221> NAME/KEY: MOD_RES
<222> LOCATION: (9)..(9)
<223> OTHER INFORMATION: Citrulline
```

```
-continued

<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 328

Gly Cys Lys Thr Asp Pro Arg Cys Xaa Xaa Gln Glu Tyr
1               5                   10

<210> SEQ ID NO 329
<211> LENGTH: 13
<212> TYPE: PRT
<213> ORGANISM: Artificial sequence
<220> FEATURE:
<223> OTHER INFORMATION: RgIA analog with a triazole bridge between
      position 2 and position 8
<220> FEATURE:
<221> NAME/KEY: DISULFID
<222> LOCATION: (3)..(12)
<220> FEATURE:
<221> NAME/KEY: MISC_FEATURE
<222> LOCATION: (2)..(8)
<223> OTHER INFORMATION: Amino acid at position 2 and amino acid at
      position 8 form a triazole bridge
<220> FEATURE:
<221> NAME/KEY: VARIANT
<222> LOCATION: (2)..(2)
<223> OTHER INFORMATION: (S)-Propargyl glycine or (S)-5-azidonorvaline
<220> FEATURE:
<221> NAME/KEY: VARIANT
<222> LOCATION: (8)..(8)
<223> OTHER INFORMATION: (S)-Propargyl glycine or (S)-5-azidonorvaline
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 329

Gly Xaa Cys Thr Asp Pro Arg Xaa Xaa Xaa Gln Cys Tyr
1               5                   10

<210> SEQ ID NO 330
<211> LENGTH: 13
<212> TYPE: PRT
<213> ORGANISM: Artificial sequence
<220> FEATURE:
<223> OTHER INFORMATION: RgIA analog with a triazole bridge between
      position 3 and position 12
<220> FEATURE:
<221> NAME/KEY: DISULFID
<222> LOCATION: (2)..(8)
<220> FEATURE:
<221> NAME/KEY: MISC_FEATURE
<222> LOCATION: (3)..(12)
<223> OTHER INFORMATION: Amino acid at position 3 and amino acid at
      position 12 form a triazole bridge
<220> FEATURE:
<221> NAME/KEY: VARIANT
<222> LOCATION: (3)..(3)
<223> OTHER INFORMATION: (S)-Propargyl glycine or (S)-5-azidonorvaline
<220> FEATURE:
<221> NAME/KEY: VARIANT
<222> LOCATION: (12)..(12)
```

```
<223> OTHER INFORMATION: (S)-Propargyl glycine or (S)-5-azidonorvaline
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 330

Gly Cys Xaa Thr Asp Pro Arg Cys Xaa Xaa Gln Xaa Tyr
1               5                   10

<210> SEQ ID NO 331
<211> LENGTH: 13
<212> TYPE: PRT
<213> ORGANISM: Artificial sequence
<220> FEATURE:
<223> OTHER INFORMATION: RgIA analog with Triazole bridge #1
<220> FEATURE:
<221> NAME/KEY: DISULFID
<222> LOCATION: (3)..(12)
<220> FEATURE:
<221> NAME/KEY: MISC_FEATURE
<222> LOCATION: (2)..(8)
<223> OTHER INFORMATION: (S)-Propargyl glycine at position 2 and
      (S)-5-azidonorvaline at position 8 form a triazole bridge
<220> FEATURE:
<221> NAME/KEY: MOD_RES
<222> LOCATION: (2)..(2)
<223> OTHER INFORMATION: (S)-Propargyl glycine
<220> FEATURE:
<221> NAME/KEY: MOD_RES
<222> LOCATION: (8)..(8)
<223> OTHER INFORMATION: (S)-5-Azidonorvaline
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 331

Gly Xaa Cys Thr Asp Pro Arg Xaa Xaa Xaa Gln Cys Tyr
1               5                   10

<210> SEQ ID NO 332
<211> LENGTH: 13
<212> TYPE: PRT
<213> ORGANISM: Artificial sequence
<220> FEATURE:
<223> OTHER INFORMATION: RgIA analog with Triazole bridge #2
<220> FEATURE:
<221> NAME/KEY: DISULFID
<222> LOCATION: (3)..(12)
<220> FEATURE:
<221> NAME/KEY: MISC_FEATURE
<222> LOCATION: (2)..(8)
<223> OTHER INFORMATION: (S)-5-Azidonorvaline at position 2 and
      (S)-propargyl glycine at position 8 form a triazole bridge
<220> FEATURE:
<221> NAME/KEY: MOD_RES
<222> LOCATION: (2)..(2)
<223> OTHER INFORMATION: (S)-5-Azidonorvaline
```

```
<220> FEATURE:
<221> NAME/KEY: MOD_RES
<222> LOCATION: (8)..(8)
<223> OTHER INFORMATION: (S)-Propargyl glycine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 332

Gly Xaa Cys Thr Asp Pro Arg Xaa Xaa Xaa Gln Cys Tyr
 1               5                  10

<210> SEQ ID NO 333
<211> LENGTH: 13
<212> TYPE: PRT
<213> ORGANISM: Artificial sequence
<220> FEATURE:
<223> OTHER INFORMATION: RgIA analog with Triazole bridge #3
<220> FEATURE:
<221> NAME/KEY: DISULFID
<222> LOCATION: (2)..(8)
<220> FEAT

```
<223> OTHER INFORMATION: (S)-5-Azidonorvaline at position 3 and
      (S)-propargyl glycine at position 12 form a triazole bridge
<220> FEATURE:
<221> NAME/KEY: MOD_RES
<222> LOCATION: (3)..(3)
<223> OTHER INFORMATION: (S)-5-Azidonorvaline
<220> FEATURE:
<221> NAME/KEY: MOD_RES
<222> LOCATION: (12)..(12)
<223> OTHER INFORMATION: (S)-Propargyl glycine
<220> FEATURE:
<221> NAME/KEY: MOD_RES
<222> LOCATION: (9)..(9)
<223> OTHER INFORMATION: Citrulline
<220> FEATURE:
<221> NAME/KEY: MOD_RES
<222> LOCATION: (10)..(10)
<223> OTHER INFORMATION: 3-iodo-Tyrosine
<220> FEATURE:
<221> NAME/KEY: MOD_RES
<222> LOCATION: (13)..(13)
<223> OTHER INFORMATION: AMIDATION

<400> SEQUENCE: 334

Gly Cys Xaa Thr Asp Pro Arg Cys Xaa Xaa Gln Xaa Tyr
1               5                   10
```

MODIFICATIONS AND USES OF CONOTOXIN PEPTIDES

CROSS-REFERENCE TO RELATED APPLICATIONS

This application is a continuation of U.S. application Ser. No. 15/525,024, which is a U.S. National Stage of International Application No. PCT/US2015/059613, filed Nov. 6, 2015, which claims the benefit of U.S. Provisional Patent Application No. 62/123,123 filed Nov. 7, 2014, the entire contents of each of which are incorporated by reference herein.

REFERENCE TO SEQUENCE LISTING SUBMITTED ELECTRONICALLY

This application incorporates by reference a Sequence Listing submitted as a text file entitled "14520-012-999_SE-Q_LISTING.txt" created on Sep. 21, 2020 and having a size of 143,643 bytes.

FIELD OF THE DISCLOSURE

The disclosure provides modified sequences of conotoxin peptides, pharmaceutical compositions of conotoxin peptides, and methods of use thereof for treating pain and other disorders.

BACKGROUND OF THE DISCLOSURE

Predatory marine snails in the genus Conus have venoms that are rich in neuropharmacologically active peptides (conotoxin peptides or cone snail proteins "CSP"). There are approximately 500 species in Conus, and among those that have been examined so far, a conserved feature is the presence of α-conotoxin peptides in their venom. Native α-Conotoxin peptides are highly disulfide cross-linked peptides with C1-C3 and C2-C4 disulfide bonds.

Due to high sequence variability of their non-cysteine residues, α-conotoxins are extremely diverse and each Conus species has a unique complement of α-conotoxin peptides. α-Conotoxin peptides are synthesized as large precursors, and the mature toxin is generated by a proteolytic cleavage toward the C-terminus of the precursor. In contrast to the variable inter-cysteine sequences of the mature toxins, the precursors and the genes encoding them are quite conserved both among α-conotoxin peptides in a given Conus species and from species to species.

α-Conotoxin peptides have generally been shown to be nicotinic acetylcholine receptor (nAChR) antagonists (McIntosh, et al., 1999; Janes, 2005; Dutton et al., 2001; Arias et al., 2000). nAChRs are a group of acetylcholine gated ion channels that are part of the ligand gated ion channel superfamily. They are pentamers of transmembrane subunits surrounding a central ion conducting channel. Many different subunits have been identified, and most fall into two main subfamilies (α subunits and β subunits). The subunits can associate in various combinations in the receptor pentamers, leading to a diverse family of receptor subtypes. Most of the subtypes contain subunits from both the α and β subunit families, e.g., the human adult muscle subtype contains two α subunits and a β subunit (in addition to a δ and an ε subunit), and the α4β2 central nervous system subtype is composed of α4 and β2 subunits. Examples of nAChRs that are composed of only α subunits are the α7 and α9 subtypes (homopentamers) and the α9α10 subtype (an all α heteropentamer). Phylogenetic analysis shows that the α7, α9, and α10 subunits are more closely related to each other than they are to other nAChR subunits.

The α9 and α10 nAChR subunits are expressed in diverse tissues. In the inner ear α9α10 nAChRs mediate synaptic transmission between efferent olivocochlear fibers and cochlear hair cells. The α9 and α10 subunits are also found in dorsal root ganglion neurons, lymphocytes, skin keratinocytes, and the pars tuberalis of the pituitary. In addition, the α9 nAChR subunit is active in breast cancer. α-Conotoxin peptide RgIA (SEQ ID NO:1) has been shown to block α9α10 nAChR (Ellison, et al., 2006). Certain analogs of RgIA have also been shown to block α9α10 nAChR as demonstrated in US 2009/0203616, US 2012/0220539, and WO 2008/011006.

In general, the therapeutic potential of peptide drug candidates can be improved either by formulation or by their non-covalent or covalent chemical modification. The practical utilization of peptides as therapeutics has been limited by relative low solubility and physicochemical stability, both in formulation as drug products and in vivo after administration to an animal or a human. Parenteral peptide drugs, in particular, are rapidly cleared from circulation by kidney filtration or the reticuloendothelial system. They are also often susceptible to rapid degradation by circulating proteases. Finally, peptides can be immunogenic which can limit their therapeutic use due to risk of removal by antibodies or, in some instances, incidence of inflammatory reactions (e.g., anaphylactic-like reactions). In addition, oral delivery of peptides is hampered by the lack of dedicated peptide transporters in the intestines that allow the uptake of peptides of lengths greater than 2-4 amino acids, as well as the difficulty of passage though the low pH environment of the stomach.

SUMMARY OF THE DISCLOSURE

The present disclosure relates to modifications to α-conotoxin peptides including RgIA and RgIA analogs in order to increase their potential for use in therapeutics for pain and inflammation. These changes include amino acid modifications, which as used herein include deletions, substitutions, and additions. These changes also include attaching non amino acid functional groups or molecules to the peptides such as fatty acid chains, acetyl groups, PEGylation, and/or glycosylation groups. Additional changes include RgIA analogs modified to contain glycine-alanine N- to C-terminus bridges that effectively cyclize the peptides. These approaches increase desirable drug-like properties including peptide stability in vitro and in vivo, increase their half-life in circulation, increase their oral bioavailability such as by facilitation of passage through the stomach and increase in absorption, and reduce renal/hepatic clearance once in circulation. These modifications of analog conotoxin peptides are used to block the α9α10 subtype of the nicotinic acetylcholine receptor (nAChR) with very high selectivity and affinity and thereby produce analgesic and anti-inflammatory effects in inflammatory, neuropathic, cancer, and other disease states.

BRIEF DESCRIPTION OF THE FIGURES

FIG. 2A shows CSP-2 and CSP-2-NH2 stability in rat serum at time 0-2 hours; CSP-2-NH2 shows increased stability compared to CSP-2 over time. FIG. 2B shows CSP-4 and CSP-4-NH2 stability in human plasma (Citrate) during time 0-24 hours; CSP-4-NH2 shows increased stability compared to CSP-4 over time. Measurements taken at time=0 were taken within 30 seconds of mixing peptide with serum.

FIG. 3A: SEQ ID NO:320; FIG. 3B: SEQ ID NO:321; and FIG. 3C: SEQ ID NO:322.

DETAILED DESCRIPTION

Figure 1A:
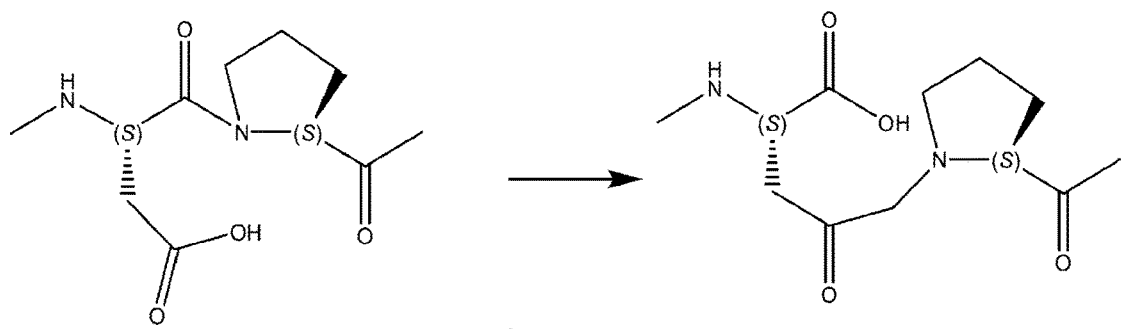
FIGS. 1A-1G show modifications to RgIA to constrain the isomerization of the conserved aspartate residue in the conserved sequence Asp-Pro-Arg. Isomerization is shown in FIG. 1A. Modifications are shown in FIGS. 1B-1G.

The present disclosure relates to the α-conotoxin peptide RgIA (SEQ ID NO:1), conotoxin peptides that are analogs of the α-conotoxin peptide RgIA, as well as modifications thereof (collectively "RgIA analogs" herein). These RgIA analogs block the α9α10 subtype of the nicotinic acetylcholine receptor (nAChR) and can be used to treat pain and inflammation. These pain conditions include musculoskeletal pain, inflammatory pain, cancer pain, neuropathic pain syndromes including diabetes neuropathic pain, chemotherapy induced pain, postherpetic neuralgia, idiopathic neuropathic peripheral pain, phantom limb pain, orthopedic pain including osteoarthritis, and autoimmune/inflammatory-induced pain including rheumatoid arthritis pain. The RgIA analogs can also be used in further drug development as described herein.

Marine snails produce a number of peptides that have neurotoxic effects on prey. Peptides from the genus Conus typically range from 12 to 30 amino acids in length and contain 4 or more cysteine residues; the conotoxins of the subtype alpha contain and form two disulfide bonds in a C1-03 and C2-C4 connectivity. α-Conotoxin peptides bind nAChRs. One of these, RgIA (SEQ ID NO:1), is selective for α9α10 nAChRs that have been demonstrated to have analgesic properties in several models of neuropathic pain and inflammation. In addition to the conserved cysteine residues, the proline residue is also conserved and the DPR region functions in binding to the α9α10 nAChR. The arginine residue at position 9 is associated with increased selectivity for the human α9α10 nAChR.

Previously described (PCT/US2014/040374) analogs of RgIA that have desired drug-like characteristics such as increased affinity for the human α9α10 nAChR target compared to the parent RgIA and increased in vitro and in vivo stability (Table 1). Previously described RgIA analogs are also disclosed in U.S. Pat. Nos. 6,797,808; 7,279,549; 7,666,840; 7,902,153; 8,110,549; 8,487,075; and 8,735,541; and in U.S. patent application Ser. Nos. 12/307,953 and 13/289,494; the sequences of which are incorporated by reference. The present disclosure also relates to additional analogs of RgIA as listed in Table 2.

The present disclosure describes a series of modifications that can be made to RgIA analogs, including those listed in Tables 1 and 2, to improve their drug like characteristics for their therapeutic use including as analgesics.

TABLE 1

| Analog | Sequence | SEQ ID NO. |
|---|---|---|
| CSP-P | GCCSDPRCRYRCR | 1 |
| CSP-1 | GCCSDPRCRX12RCR | 2 |
| CSP-2 | GCCTDPRCX11X12QCR | 3 |
| CSP-3 | GCCTDPRCX11X12QCRRR | 4 |
| CSP-4 | GCCTDPRCX11X12QCY | 5 |
| CSP-5 | GX13CTDPRX13X11X12QCR | 6 |
| CSP-6 | GCCTDPRCRX12QCF | 7 |
| CSP-7 | GCCTDPRCRX12QCY | 8 |
| CSP-8 | GCCTDPRCRX12QCW | 9 |

X11 = Citrulline
X12 = 3-iodo-Tyrosine
X13 = Selenocysteine

TABLE 2

| Sequence | SEQ ID NO. |
|---|---|
| GCCTDPRCX21X12QCYRR | 222 |
| GCCTDPRCX21X12QCRRY | 223 |
| GCCTDPRCX21X12QCF | 224 |
| GCCTDPRCX21X12QCW | 225 |
| GCCTDPRCX21X12QCYY | 226 |
| GCCTDPRCX21X12QCYR | 227 |
| GCCTDPRCRX12QCRRR | 228 |
| GCCTDPRCRX12QCYRR | 229 |
| GCCTDPRCRX12QCRRY | 230 |
| GCCTDPRCRX12QCYY | 231 |
| GCCTDPRCRX12QCYR | 232 |
| GCCSDPRCNYDHPEIC-COOH | 233 |
| GCCSDPRCNYDHPEIC-amide | 234 |
| GCCSHPACSVNHPELC-COOH | 235 |
| GCCSHPACSVNHPELC-amide | 236 |
| GCCTDPRCRYRCR | 237 |
| GCCSDX14QRCRYRCR | 238 |
| GCCTDX14RCRYRCR | 239 |
| GCCSDPRCRX15RCR | 240 |
| GCCTDPRCRX15RCR | 241 |
| X15GCCSDX14RCRX15RCR | 242 |

TABLE 2-continued

| Sequence | SEQ ID NO. |
|---|---|
| X15GCCTDX14RCRX15RCR | 243 |
| GCCSDPRCX16YRCR | 244 |
| GCCSDPRCX21X12RCR | 245 |
| GX13CTDPRX13X21X12QCK | 246 |
| GX13CSDPRX13RYRCR | 247 |
| GCCTDPRCX21X12RCR | 248 |
| GCCSDPRCX21YRCR | 249 |
| GCCSDPRCRYQCR | 250 |
| GCCSDPRCFWRCR | 251 |
| GX17CSDPRCRYRCR | 252 |
| GCCADPRCRYRCR | 253 |
| GCCYDPRCRYRCR | 254 |
| GCCSDPRX17RYRCR | 255 |
| GCCSDPRCGYRCR | 256 |
| GCCSDPRCAYRCR | 257 |
| GCCSDPRCVYRCR | 258 |
| GCCSDPRCLYRCR | 259 |
| GCCSDPRCIYRCR | 260 |
| GCCSDPRCMYRCR | 261 |
| GCCSDPRCFYRCR | 262 |
| GCCSDPRCWYRCR | 263 |
| GCCSDPRCPYRCR | 264 |
| GCCSDPRCSYRCR | 265 |
| GCCSDPRCTYRCR | 266 |
| GCCSDPRCCYRCR | 267 |
| GCCSDPRCYYRCR | 268 |
| GCCSDPRCNYRCR | 269 |
| GCCSDPRCQYRCR | 270 |
| GCCSDPRCDYRCR | 271 |
| GCCSDPRCEYRCR | 272 |
| GCCSDPRCKYRCR | 273 |
| GCCSDPRCHYRCR | 274 |
| GCCSDPRCRFRCR | 275 |
| GCCSDPRCRYHCR | 276 |
| GCCSDPRCX18X12RCR | 277 |
| GCCSDPRCRYRC | 278 |
| GCCSEPRCRYRCR | 279 |
| GCCSDVRCRYRCR | 280 |
| GCCSDPRCAYRCR | 281 |

TABLE 2-continued

| Sequence | SEQ ID NO. |
|---|---|
| GCCSHPACRYRCR | 282 |
| GCCSDPRCX19YRCR | 283 |
| ACCSDRRCRWRC | 284 |
| FDGRNAPADDKASDLIAQIVRRACCSDRRCRWRCG | 285 |
| X15GCCSX14RCRX15RCR | 286 |
| SNKRKNAAMLDMIAQHAIRGCCSDPRCRYRCR | 287 |
| DECCSNPACRVNNPHV | 288 |
| SDGRNVAAKAFHRIGRTIRDECCSN-PACRVNNPHVCRRR | 289 |
| DECCSNPACRLNNPHACRRR | 290 |
| DX20CCSNPACRLNNPHACRRR | 291 |
| DECCSNX14ACRLNNPHACRRR | 292 |
| X20DX20CCSNX14ACRLNNPHACRRR | 293 |
| DECCSNPACRLNNX14HACRRR | 294 |
| X20DX20CCSNPACRLNX14HACRRR | 295 |
| DECCSNX14ACRLNNX14HACRRR | 296 |
| X20DX20CCSNX14ACRLNNX14HACRRR | 297 |
| DECCSNPACRLNNPHVCRRR | 298 |
| DX20CCSNPACRLNNPHVCRRR | 299 |
| DECCSNX20ACRLNNPHVCRRR | 300 |
| X20DX20CCSNX14ACRLNPHVCRRR | 301 |
| DECCSNPACRLNNX214HVCRRR | 302 |
| X20DX20CCSNX14ACRLNNPHVCRRR | 303 |
| DECCSNX14ACRLNNX14HVCRRR | 304 |
| X20DX20CCSNX14ACRLNNX14HVCRRR | 305 |
| GCCSHPACNVDHPEIC | 306 |
| MFTVFLLVVLATTVVSFTSDRAFRGRNSAANDKRSDLAALSVRRGCCSHPACSVNHPELCGRRR | 307 |
| ECCTNPVCHAEHQHELCARRR | 308 |
| ECCTNPVCHAX21HQELCARRR | 309 |
| ECCTNPVCHAX21HQX21LCARRR | 310 |
| ECCTNPVCHA3HQX21LCARRR | 311 |
| X21CCTNPVCHAEHQHELCARRR | 312 |
| X21CCTNPVCHAX21HQELCARRR | 313 |
| X21CCTNPVCHAX21HQX21LCARRR | 314 |
| X21CCTNPVCHA3HQX21LCARRR | 315 |
| GCCSHPVCSAMSPIC | 316 |
| GCCSHPVCSAMSX1IC | 317 |
| GCCSHX14VCSAMSX1IC | 318 |
| GCCSHX14VCSAMSPIC | 319 |

X11 = Citrulline
X12 = 3-iodo-Tyrosine
X13 = Selenocysteine
X14 = hydroxy-Pro
X15 = mono-halo Tyr including iodo-Tyr, bromo-Tyr
X16 = homo-Arg or ornithine
X17 = homocysteine
X18 = omega-nitro-Arg
X19 = D-Arg
X20 = γ-carboxy-Glu (Gla)
X21 = 7-carboxy-Glu In various embodiments, analog RgIA analogs disclosed herein have the formula X10 X6 X7 X3 D P R X8 X1 X12 X4 X9 X5 (SEQ ID NO:10), wherein X1 is des-X1, Arg or citrulline; X3 is des-X3, Ser, or Thr; X4 is des-X4, Arg or Gln; X5 is des-X5, Arg, Tyr, Phe, Trp, Tyr-Tyr, Tyr-Arg, Arg-Arg-Arg, Arg-Arg, Arg-Tyr, Arg-Arg-Tyr, or Tyr-Arg-Arg; X6 is des-X6, Cys, or selenocysteine; X7 is des-X7, Cys, or selenocysteine; X8 is des-X8, Cys, or selenocysteine; X9 is des-X9, Cys, or selenocysteine; and X10 is des-X10 or Gly. In one embodiment, X10 is Gly, X6 is Cys or selenocysteine, X7 is Cys, X3 is Ser or Thr; X8 is Cys or selenocysteine, X1 is Arg or citrulline, X4 is Arg or Gln, X9 is Cys, and X5 is Arg, Tyr, Phe, Trp, or Arg-Arg-Arg (SEQ ID NO:11). In one embodiment, X10 is Gly, X6 is Cys or selenocysteine, X7 is Cys, X3 is Thr, X8 is Cys or selenocysteine, X1 is Arg or citrulline, X4 is Gln, X9 is Cys, and X5 is Arg or Tyr (SEQ ID NO:12).

Figure 1B:
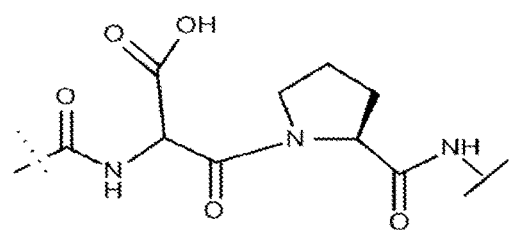
Figure 1C:
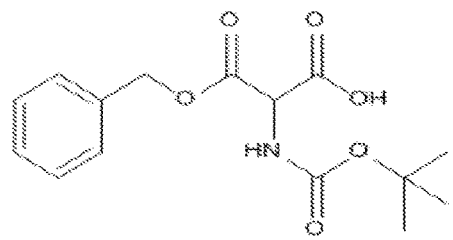

In various embodiments modifications to the RgIA and its analogs are made so as to prevent the isomerization of the conserved aspartate residue to isoaspartate in the conserved tripeptide sequence "Asp-Pro-Arg". This isomerization is shown in FIG. 1A. This approach prevents this isomerization and results in stable RgIA analogs that maintain their pharmacological properties of high affinity and high selectivity in binding to the intended target, namely α9α10 nAChRs. Therefore, despite the small globular size of RgIA conotoxin peptides, the peptide bond replacements and the proposed strategies presented hereby result in bioactive, potent, and more stable peptides. Three different chemical approaches are used and evaluated. In the first teaching, the aspartic acid is replaced with amino malonic acid (FIG. 1B; 2-amino propandioic acid), which is equivalent to an aspartic acid with a shortened side chain. This derivative with the shortened side chain cannot form 5-membered succinic acid anhydride intermediate that is necessary for production of the isomer. Synthesis can be accomplished via standard peptide chemistry using a suitably protected amino malonic acid (e.g., FIG. 10).

In the next two teachings, a non-peptide bond is engineered to join the aspartic acid replacement and the proline via N-alkylation of the proline; both examples are non-hydrolysable and therefore not susceptible to isomerization.

Figure 1D:
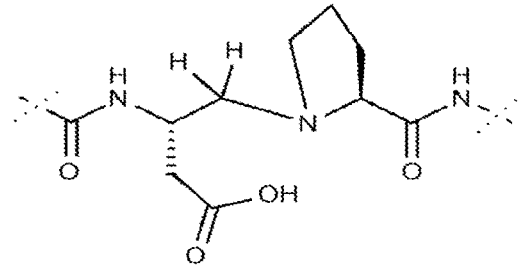
Figure 1E:
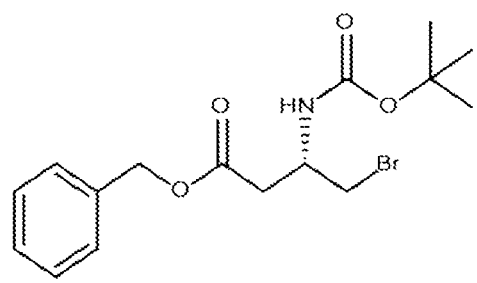

The second approach replaces the peptide-chain carbonyl group of aspartic acid with a methylene group (FIG. 1D) to afford a 'reduced peptide bond'. This can be prepared by alkylating the proline with an appropriately protected Asp replacement such as (3S)-4-bromo-3-[[(1,1-dimethylethoxy)carbonyl]amino]-butanoic acid (FIG. 1E) which itself is incorporated into the peptide chain via standard peptide chemistry.

Figure 1F:
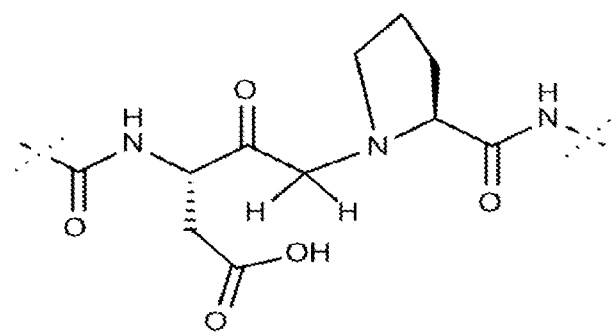
Figure 1G:
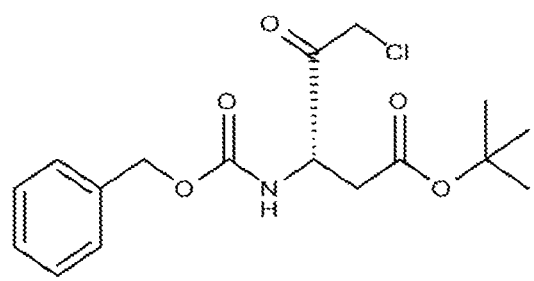

The third approach replaces the peptide chain carbonyl group of aspartic acid with a ketomethyl group (FIG. 1F) which is the equivalent of inserting a methylene group in the peptide chain between Asp and Pro. This can be prepared by alkylating the proline with an appropriately protected Asp replacement such as 1,1-dimethylethyl-(3S)-5-chloro-4-oxo-3-[[(phenylmethoxy)carbonyl]amino]-pentanoate (FIG. 1G), which itself is incorporated into the peptide chain via standard peptide chemistry.

In various embodiments, amino acid modifications can increase peptide stability by replacement of amino acid residues that may be prone to enzymatic cleavage. Such modifications include: replacement of any L-amino acid with the corresponding D-amino acid; replacement of Gly with a neutral amino acid, including Val, Nor-Val, Leu, or Ile; replacement of Arg with His or Lys; replacement of Pro with Gly; replacement of Gly with Pro, and/or replacement of cysteine with selenocysteine. Illustrative peptide sequences with such modifications are described in Table 4.

TABLE 4

Modified peptide sequences with amino acid modifications

| Sequence | SEQ ID NO. |
| --- | --- |
| GCCSDPRCRYRCH | 30 |
| GCCSDPRCRYRCK | 31 |
| GCCSDPRCRX22RCR | 32 |
| X23CCSDPRCRYRCR | 33 |
| X24CCSDPRCRYRCR | 34 |
| GCCSDX25RCRYRCR | 35 |
| GCCSX26PRCRYRCR | 36 |
| GCCSDPX27CRYRCR | 37 |
| GCCSX26X25RCRYRCR | 38 |
| GCCSDX25X27CRYRCR | 39 |
| GCCSX26X25X27CRYRCR | 40 |
| GCCSDPRCRYHCR | 41 |
| GCCSDPRCRYKCR | 42 |
| PCCSDPRCRYRCR | 43 |
| GCCSDPRCRX12RCH | 44 |
| GCCSDPRCRX12RCK | 45 |
| GCCSDPRCRX22RCH | 46 |
| X23CCSDPRCRX12RCR | 47 |
| X24CCSDPRCRX12RCR | 48 |
| GCCSDX25RCRX12RCR | 49 |
| GCCSX26PRCRX12RCR | 50 |
| GCCSDPX27CRX12RCR | 51 |
| GCCSX26X25RCRX12RCR | 52 |
| GCCSDX25X27CRX12RCR | 53 |
| GCCSX26X25X27CRX12RCR | 54 |

TABLE 4-continued

Modified peptide sequences with amino acid modifications

| Sequence | SEQ ID NO. |
| --- | --- |
| GCCSDPRCRX12HCR | 55 |
| GCCSDPRCRX12KCR | 56 |
| PCCSDPRCRX12RCR | 57 |
| GCCSDPRCHX12RCR | 58 |
| GCCSDPRCKX12RCR | 59 |
| GCCTDPRCRX12RCH | 60 |
| GCCTDPRCRX12RCK | 61 |
| GCCTDPRCRX22RCR | 62 |
| X23CCTDPRCRX12RCR | 63 |
| X24CCTDPRCRX12RCR | 64 |
| GCCTDX25RCRX12RCR | 65 |
| GCCTX26PRCRX12RCR | 66 |
| GCCTDPX27CRX12RCR | 67 |
| GCCTX26X25RCRX12RCR | 68 |
| GCCTDX25X27CRX12RCR | 69 |
| GCCTX26X25X27CRX12RCR | 70 |
| GCCTDPRCRX12HCR | 71 |
| GCCTDPRCRX12KCR | 72 |
| PCCTDPRCRX12RCR | 73 |
| GCCTDPRCHX12RCR | 74 |
| GCCTDPRCKX12RCR | 75 |
| GCCTDPRCX11X12QCHRR | 76 |
| GCCTDPRCX11X12QCKRR | 77 |
| GCCTDPRCX11X12QCRHR | 78 |
| GCCTDPRCX11X12QCRKR | 79 |
| GCCTDPRCX11X12QCRRH | 80 |
| GCCTDPRCX11X12QCRRK | 81 |
| GCCTDPRCX11X22QCRRR | 82 |
| X23CCTDPRCX11X12QCRRR | 83 |
| X24CCTDPRCX11X12QCRRR | 84 |
| GCCTDX25RCX11X12QCRRR | 85 |
| GCCTX26PRCX11X12QCRRR | 86 |
| GCCTDPX27CX11X12QCRRR | 87 |
| GCCTX26X25RCX11X12QCRRR | 88 |
| GCCTDX25X27CX11X12QCRRR | 89 |
| GCCTX26X25X27CX11X12QCRRR | 90 |
| PCCTDPRCX11X12QCRRR | 91 |
| GCCTDPRCX11X22QCY | 92 |

TABLE 4-continued

Modified peptide sequences with amino acid modifications

| Sequence | SEQ ID NO. |
|---|---|
| GCCTDPRCX11X12QCX22 | 93 |
| X23CCTDPRCX11X12QCY | 94 |
| X24CCTDPRCX11X12QCY | 95 |
| GCCTDX25RCX11X12QCY | 96 |
| GCCTX26PRCX11X12QCY | 97 |
| GCCTDPX27CX11X12QCY | 98 |
| GCCTX26X25RCX11X12QCY | 99 |
| GCCTDX25X27CX11X12QCY | 100 |
| GCCTX26X25X27CX11X12QCY | 101 |
| PCCTDPRCX11X12QCY | 102 |
| GX13CTDPRX13X11X12QCH | 103 |
| GX13CTDPRX13X11X12QCK | 104 |
| GX13CTDPRX13X11X22QCR | 105 |
| X23X13CTDPRX13X11X12QCR | 106 |
| X24X13CTDPRX13X11X12QCR | 107 |
| GX13CTDX25RX13X11X12QCR | 108 |
| GX13CTX26PRX13X11X12QCR | 109 |
| GX13CTDPX27X13X11X12QCR | 110 |
| GX13CTX26X25RX13X11X12QCR | 111 |
| GX13CTDX25X27X13X11X12QCR | 112 |
| GX13CTX26X25X27X13X11X12QCR | 113 |
| PX13CTDPRX13X11X12QCR | 114 |
| GCCTDPRCRX22QCF | 115 |
| X23CCTDPRCRX12QCF | 116 |
| X24CCTDPRCRX12QCF | 117 |
| GCCTDX25RCRX12QCF | 118 |
| GCCTX26PRCRX12QCF | 119 |
| GCCTDPX27CRX12QCF | 120 |
| GCCTX26X25RCRX12QCF | 121 |
| GCCTDX25X27CRX12QCF | 122 |
| GCCTX26X25X27CRX12QCF | 123 |
| PCCTDPRCRX12QCF | 124 |
| GCCTDPRCRX22QCY | 125 |
| GCCTDPRCRX12QCX22 | 126 |
| X23CCTDPRCRX12QCY | 127 |
| X24CCTDPRCRX12QCY | 128 |
| GCCTDX25RCRX12QCY | 129 |
| GCCTX26PRCRX12QCY | 130 |
| GCCTDPX27CRX12QCY | 131 |
| GCCTX26X25RCRX12QCY | 132 |
| GCCTDX25X27CRX12QCY | 133 |
| GCCTX26X25X27CRX12QCY | 134 |
| PCCTDPRCRX12QCY | 135 |
| GCCTDPRCRX22QCW | 136 |
| X23CCTDPRCRX12QCW | 137 |
| X24CCTDPRCRX12QCW | 138 |
| GCCTDX25RCRX12QCW | 139 |
| GCCTX26PRCRX12QCW | 140 |
| GCCTDPX27CRX12QCW | 141 |
| GCCTX26X25RCRX12QCW | 142 |
| GCCTDX25X27CRX12QCW | 143 |
| GCCTX26X25X27CRX12QCW | 144 |
| PCCTDPRCRX12QCW | 145 |
| GX13CTDPRCX11X12QCY | 146 |
| GCX13TDPRCX11X12QCY | 147 |
| GCCTDPRX13X11X12QCY | 148 |
| GCCTDPRCX11X12QX13Y | 149 |
| GX13CTDPRX13X11X12QCY | 150 |
| GCX13TDPRCX11X12QX13Y | 151 |
| GX13X13TDPRCX11X12QCY | 152 |
| GCCTDPRX13X11X12QX13Y | 153 |
| GX13CTDPRCX11X12QX13Y | 154 |
| GX13X13TDPRX13X11X12QCY | 155 |
| GCX13TDPRX13X11X12QX13Y | 156 |
| GX13CTDPRX13X11X12QX13Y | 157 |
| GX13X13TDPRCX11X12QX13Y | 158 |
| GX13X13TDPRX13X11X12QX13Y | 159 |
| GX13CTDPRCRX12QCY | 160 |
| GCX13TDPRCRX12QCY | 161 |
| GCCTDPRX13RX12QCY | 162 |
| GCCTDPRCRX12QX13Y | 163 |
| GX13CTDPRX13RX12QCY | 164 |
| GCX13TDPRCRX12QX13Y | 165 |
| GX13X13TDPRCRX12QCY | 166 |
| GCCTDPRX13RX12QX13Y | 167 |

TABLE 4-continued

Modified peptide sequences with amino acid modifications

| Sequence | SEQ ID NO. |
|---|---|
| GX13CTDPRCRX12QX13Y | 168 |
| GX13X13TDPRX13RX12QCY | 169 |
| GCX13TDPRX13RX12QX13Y | 170 |
| GX13CTDPRX13RX12QX13Y | 171 |
| GX13X13TDPRCRX12QX13Y | 172 |
| GX13X13TDPRX13RX12QX13Y | 173 |

X11 = Citrulline
X12 = 3-iodo-Tyrosine
X13 = Selenocysteine
X14 = hydroxy-Pro
X15 = mono-halo Tyr including iodo-Tyr, bromo-Tyr
X16 = homo-Arg or ornithine
X17 = homocysteine
X18 = omega-nitro-Arg
X19 = D-Arg
X20 = γ-carboxy-Glu (Gla)
X21 = 7-carboxy-Glu
X22 = O-phospho-Tyr, O-sulfo-Tyr, or O-fluoro-Tyr
X23 = mono-fluoro-Glycine
X24 = di-fluoro-Glycine
X25 = D-Pro
X26 = D-Asp
X27 = D-Arg In various embodiments, linkers are added to RgIA analog peptides using standard peptide chemistry. The addition of one or more linkers around conserved regions that have been shown to be involved in target recognition increases the stability and binding affinity of RgIA analogs. Illustrative peptide sequences with such changes are described in Table 5.

TABLE 5

| Peptide sequences with added of linkers | |
|---|---|
| Sequence | SEQ ID NO. |
| X10X6X7X3[AEA]DPRX8X1X2X4X9X5 | 174 |
| X10X6X7X3D[AEA]PRX8X1X2X4X9X5 | 175 |
| X10X6X7X3DP[AEA]RX8X1X2X4X9X5 | 176 |
| X10X6X7X3DPR[AEA]X8X1X2X4X9X5 | 177 |
| X10X6X7X3[AEEA]DPRX8X1X2X4X9X5 | 178 |
| X10X6X7X3D[AEEA]PRX8X1X2X4X9X5 | 179 |
| X10X6X7X3DP[AEEA]RX8X1X2X4X9X5 | 180 |
| X10X6X7X3DPR[AEEA]X8X1X2X4X9X5 | 181 |
| X10X6X7X3[AEEEA]DPRX8X1X2X4X9X5 | 182 |
| X10X6X7X3D[AEEEA]PRX8X1X2X4X9X5 | 183 |

TABLE 5-continued

| Peptide sequences with added of linkers | |
|---|---|
| Sequence | SEQ ID NO. |
| X10X6X7X3DP[AEEEA]RX8X1X2X4X9X5 | 184 |
| X10X6X7X3DPR[AEEEA]X8X1X2X4X9X5 | 185 |

X1 = des-X1, Arg, citrulline, or ω-nitro-Arg
X2 = des-X2, Tyr, or mono-iodo-Tyr
X3 = des-X3, Ser, or Thr
X4 = des-X4, Arg or Gln
X5 = des-X5, Arg, Tyr, phenylalanine (Phe or F), tryptophan (Trp or W), Tyr-Tyr, Tyr-Arg, Arg-Arg-Arg, Arg-Arg, Arg-Tyr, Arg-Arg-Tyr, or Tyr-Arg-Arg
X6 = des-X6, Cys, or selenocysteine
X7 = des-X7, Cys, or selenocysteine
X8 = des-X8, Cys, or selenocysteine
X9 = des-X9, Cys, or selenocysteine
X10 = des-X10 or Gly
AEA = 2-amino ethoxyacetic acid
AEEA = 2-[2-[ethoxy]ethoxy]acetic acid
AEEEA = 2-[2-[2-[ethoxy]ethoxy]ethoxy]acetic acid In various embodiments the RgIA analogs may have a modification to the N-terminus and/or the C-terminus. Such modifications include: acylation of the N-terminal Gly and/or amidation of the C-terminus (Table 7); acylation of the N-terminal Gly, replacement of the C-terminal amino acid with the corresponding D-isomer (indicated by a lower case letter), and/or amidation of the C-terminus (Table 8). Selected illustrative peptide sequences with these changes are shown in Tables 7 and 8.

TABLE 7

| Peptide sequences with modification of the N-terminus or modification of the N- and C-terminus | |
|---|---|
| Sequence | SEQ ID NO. |
| Ac-GCCSDPRCRYRCR-COOH | 186 |
| Ac-GCCSDPRCRX3RCR-COOH | 187 |
| Ac-GCCTDPRCX2X3QCR-COOH | 188 |
| Ac-GCCTDPRCX2X3QCRRR-COOH | 189 |
| Ac-GCCTDPRCX2X3QCY-COOH | 190 |
| Ac-GX4CTDPRX4X2X3QCR-COOH | 191 |
| Ac-GCCTDPRCRX3QCF-COOH | 192 |
| Ac-GCCTDPRCRX3QCY-COOH | 193 |
| Ac-GCCTDPRCRX3QCW-COOH | 194 |
| Ac-GCCSDPRCRYRCR-amide | 195 |
| Ac-GCCSDPRCRX3RCR-amide | 196 |
| Ac-GCCTDPRCX2X3QCR-amide | 197 |
| Ac-GCCTDPRCX2X3QCRRR-amide | 198 |
| Ac-GCCTDPRCX2X3QCY-amide | 199 |
| Ac-GX4CTDPRX4X2X3QCR-amide | 200 |
| Ac-GCCTDPRCRX3QCF-amide | 201 |

TABLE 7-continued Peptide sequences with modification of the N-terminus or modification of the N- and C-terminus

| Sequence | SEQ ID NO. |
|---|---|
| Ac-GCCTDPRCRX3QCY-amide | 202 |
| Ac-GCCTDPRCRX3QCW-amide | 203 |

TABLE 8

Peptide sequences with replacement of the C-terminal D-amino acid with L-amino acid and modification of the N-terminus or modification of the N- and C-terminus

| Sequence | SEQ ID NO. |
|---|---|
| Ac-GCCSDPRCRYRCr-COOH | 204 |
| Ac-GCCSDPRCRX3RCr-COOH | 205 |
| Ac-GCCTDPRCX2X3QCr-COOH | 206 |
| Ac-GCCTDPRCX2X3QCRRr-COOH | 207 |
| Ac-GCCTDPRCX2X3QCy-COOH | 208 |
| Ac-GX4CTDPRX4X2X3QCr-COOH | 209 |
| Ac-GCCTDPRCRX3QCf-COOH | 210 |
| Ac-GCCTDPRCRX3QCy-COOH | 211 |
| Ac-GCCTDPRCRX3QCw-COOH | 212 |
| Ac-GCCSDPRCRYRCr-amide | 213 |
| Ac-GCCSDPRCRX3RCr-amide | 214 |
| Ac-GCCTDPRCX2X3QCr-amide | 215 |
| Ac-GCCTDPRCX2X3QCRRr-amide | 216 |
| Ac-GCCTDPRCX2X3QCr-amide | 217 |
| Ac-GX4CTDPRX4X2X3QCr-amide | 218 |
| Ac-GCCTDPRCRX3QCf-amide | 219 |
| Ac-GCCTDPRCRX3QCy-amide | 220 |
| Ac-GCCTDPRCRX3QCw-amide | 221 |

Figure 3A:
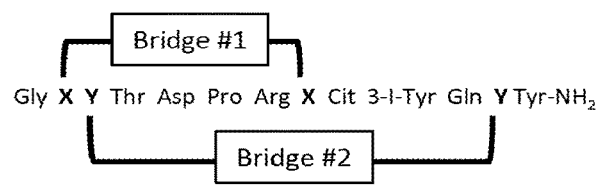
FIGS. 3A-3D show connectivity schemes of bridges in RgIA analogs. X and Y represent substitution of the amino acid residue with a naturally or unnaturally occurring amino acid in the R- or S-configuration (i.e., D- or L-amino acids) that are then coupled for bridge formation. In SEQ ID NO:25, the original amino acid at X and Y is cysteine, and the bridge is a disulfide bridge. The coupler can be a peptide, C1-C5 alkane, dialkylether, dialkyl thioether, repeating ethoxyether, alkene; or the bridging moiety may be connected directly to the peptide backbone. The bridging moiety can be diselenide, disulfide, 5- or 6-membered heterocyclic rings, an alkene, amide bond, carbamate, urea, thiourea, sulfonamide, sulfonylurea. Examples of 5-membered rings include 1,2-diazoles, oxazoles, and thiazoles, 1,3-diazoles, oxazoles and thiazoles, 1,2,3-triazoles, 1,2,4-triazoles, tetrazoles. Connectivity to the coupler units can be through the adjacent ring atoms (i.e. 1,2-, or 1,5-) or separated by one ring atom (i.e. 1,3- or 1,4-).
Figure 3B:
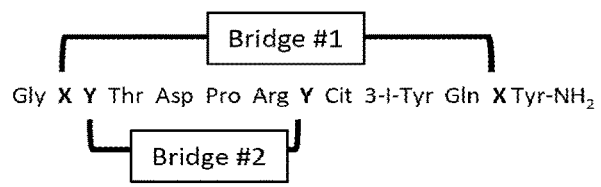
Figure 3C:
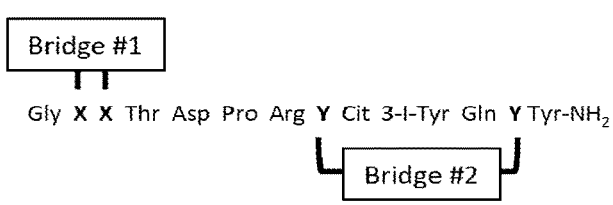
Figure 3D:
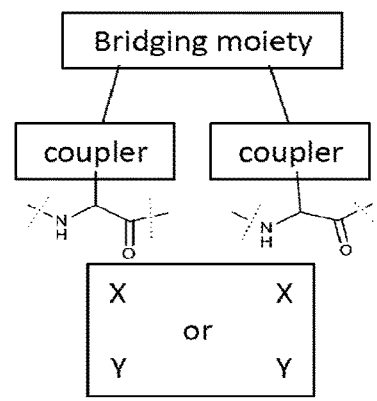
Figure 4:
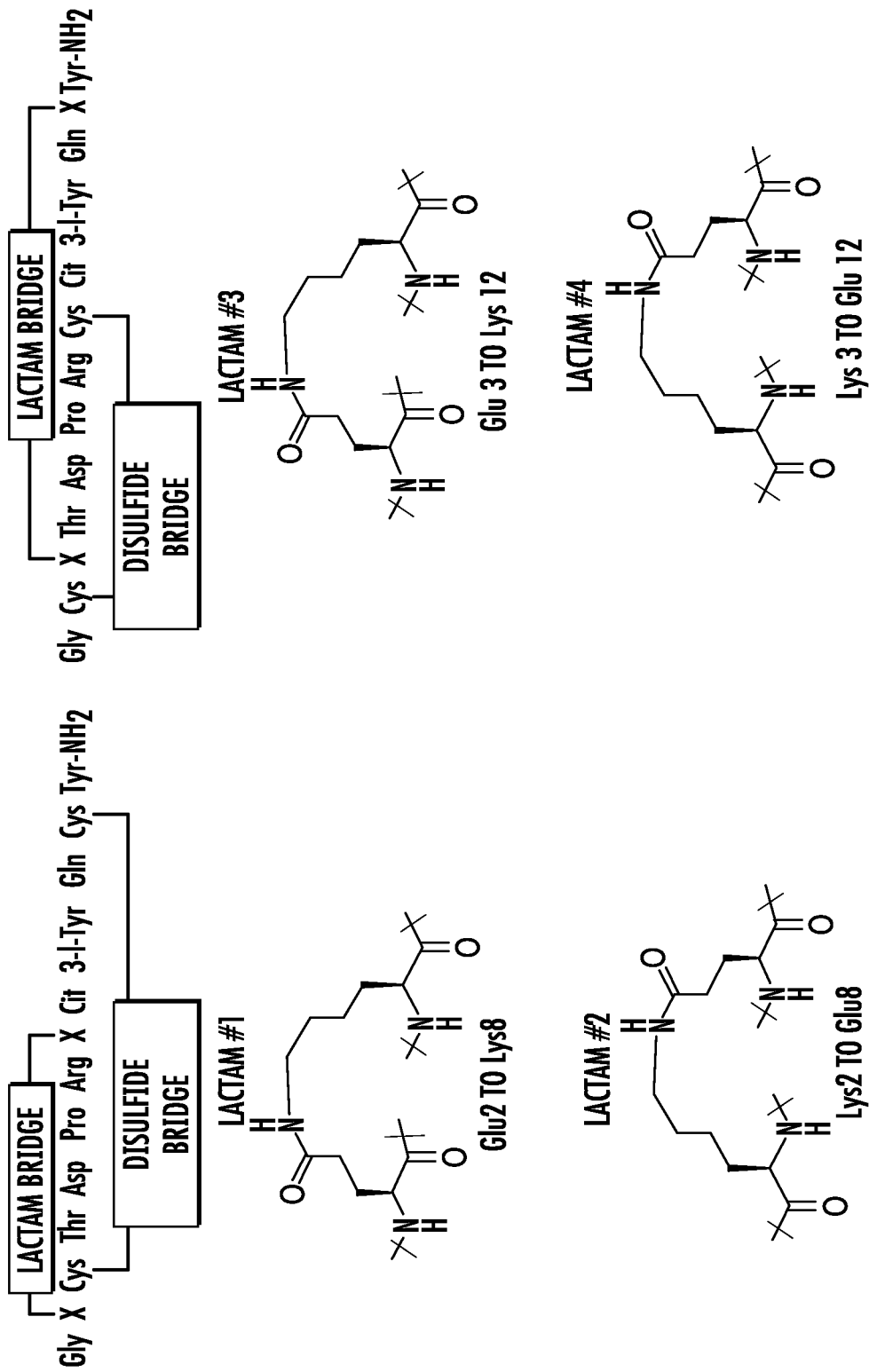
FIG. 4 shows four examples of peptides each bridged with one cysteine disulfide and one lactam bridge, the latter based on glutamic acid and lysine. Standard peptide synthesis methods are employed for the main peptide chain; the bridging amide can be formed selectively via use of protecting groups orthogonal to the chemistry employed for the main peptide chain. X designates replacement of the cysteine residue with a naturally or unnaturally occurring amino acid. The peptide sequence illustrated at the top left of FIG. 4 is SEQ ID NO:323; and the peptide sequence illustrated at the top right of FIG. 4 is SEQ ID NO:324. In the four examples shown here, cysteine is replaced with glutamic acid at position 2 and with lysine at position 8 (lactam #1; SEQ ID NO:325), cysteine is replaced with lysine at position 2 and with glutamic acid at position 8 (lactam #2; SEQ ID NO:326), cysteine is replaced with glutamic acid at position 3 and with lysine at position 12 (lactam #3; SEQ ID NO:327), cysteine is replaced with lysine at position 3 and with glutamic acid at position 12 (lactam #4; SEQ ID NO:328).
Figure 5:
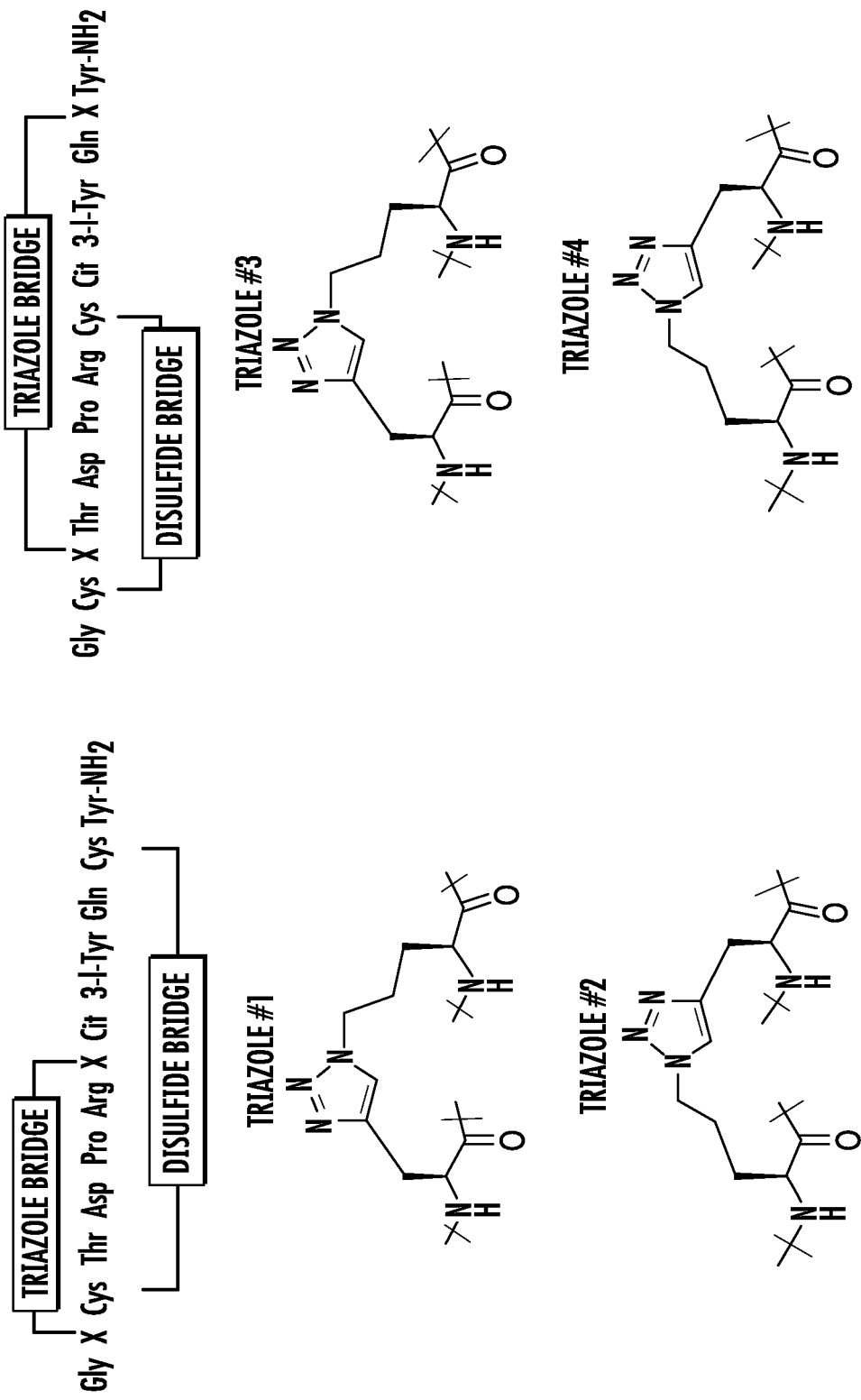
FIG. 5 shows two examples of peptides bridged with one cysteine disulfide and one triazole bridge, the latter formed from 1,3-dipolar cycloaddition reaction (i.e. "Click chemistry") from modified amino acids. X designates a modified amino acid that replaces a cysteine residue for bridge formation; in the examples given here, the modified amino acids are (S)-propargyl glycine and (S)-azidonorvaline, which have been coupled to form the 1,2,3-triazole ring shown. The peptide sequence illustrated at the top left of FIG. 5 is SEQ ID NO:329; and the peptide sequence illustrated at the top right of FIG. 5 is SEQ ID NO:330. Peptide with Triazole #1: SEQ ID NO:331; peptide with Triazole #2: SEQ ID NO:332; peptide with Triazole #3: SEQ ID NO:333; peptide with Triazole #4: SEQ ID NO:334.

In various embodiments RgIA analogs may be modified by addition of bridges such as lactam bridges or triazole bridges. As an example, FIGS. 3-5 show bridge structures formed by modifications to the peptide of SEQ ID NO:25. FIGS. 3A-3C show three different connectivity schemes for bridges in RgIA analogs. In the connectivity schemes for bridges as applied to SEQ ID NO:25, X designates cysteine residues that are each substituted with a naturally or unnaturally occurring amino acid residue. Bridges #1 and #2 are formed from bridging moieties as shown in FIG. 3D. For a given peptide, bridge #1 and #2 may be formed from the same or different bridging moieties. RgIA analogs may have both bridges #1 and #2 formed from disulfide bridges.

The RgIA analogs may have either one or both of the disulfide bridges replaced by a lactam bridge. FIG. 4 shows examples of 4 configurations of such lactam bridge replacements in RgIA analog CSP-4-NH2 (SEQ ID NO: 25). The X at positions 2, 3, 8, and 12 designates a cysteine residue replaced with a different natural amino acid or with an unnatural amino acid. Standard peptide synthesis methods are employed for the main peptide chain; the bridging amide can be formed selectively via use of protecting groups orthogonal to the chemistry employed for the main peptide chain.

The RgIA analogs may also have one cysteine disulfide and one triazole bridge. Each of the cysteine residues are replaced with an amino acid that is a bridge precursor component and contains an alkyne group or an azide group in its side chain, wherein the alkyne group and azide group are coupled to form a 1,2,3-triazole via 1,3-dipolar cycloaddition chemistry. The triazole bridge is formed from a 1,3 dipolar cycloaddition reaction, e.g., "click chemistry." FIG. 5 shows examples of 4 configurations of such triazole bridge replacements in RgIA analog CSP-4-NH2 (SEQ ID NO:25). In the examples given here, each X in the peptide represents a cysteine residue replaced with (S)-propargyl glycine or (S)-azidonorvaline.

"Variants" of RgIA analogs disclosed herein include peptides having one or more amino acid additions, deletions, stop positions, or substitutions, as compared to an analog conotoxin peptide disclosed herein.

An amino acid substitution can be a conservative or a non-conservative substitution. Variants of RgIA analogs disclosed herein can include those having one or more conservative amino acid substitutions. As used herein, a "conservative substitution" involves a substitution found in one of the following conservative substitutions groups: Group 1: alanine (Ala or A), glycine (Gly or G), serine (Ser or S), threonine (Thr or T); Group 2: aspartic acid (Asp or D), glutamic acid (Glu or E); Group 3: asparagine (Asn or N), glutamine (Gln or Q); Group 4: arginine (Arg or R), lysine (Lys or K), histidine (His or H); Group 5: isoleucine (Ile or I), leucine (Leu or L), methionine (Met or M), valine (Val or V); and Group 6: phenylalanine (Phe or F), tyrosine (Tyr or Y), tryptophan (Trp or W).

Additionally, amino acids can be grouped into conservative substitution groups by similar function, chemical structure, or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cys; acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

Variants of analog conotoxin peptide sequences disclosed or referenced herein also include sequences with at least 70% sequence identity, at least 80% sequence identity, at least 85% sequence, at least 90% sequence identity, at least 95% sequence identity, at least 96% sequence identity, at least 97% sequence identity, at least 98% sequence identity, or at least 99% sequence identity to a peptide sequence disclosed or referenced herein. More particularly, variants of the RgIA analogs disclosed herein include peptides that share: 70% sequence identity with any of SEQ ID NO:1-319; 80% sequence identity with any of SEQ ID NO:1-319; 81% sequence identity with any of SEQ ID NO:1-319; 82% sequence identity with any of SEQ ID NO:1-319; 83% sequence identity with any of SEQ ID NO:1-319; 84% sequence identity with any of SEQ ID NO:1-319; 85% sequence identity with any of SEQ ID NO:1-319; 86% sequence identity with any of SEQ ID NO:1-319; 87% sequence identity with any of SEQ ID NO:1-319; 88% sequence identity with any of SEQ ID NO:1-319; 89% sequence identity with any of SEQ ID NO:1-319; 90% sequence identity with any of SEQ ID NO:1-319; 91% sequence identity with any of SEQ ID NO:1-319; 92% sequence identity with any of SEQ ID NO:1-319; 93% sequence identity with any of SEQ ID NO:1-319; 94% sequence identity with any of SEQ ID NO:1-319; 95% sequence identity with any of SEQ ID NO:1-319; 96% sequence identity with any of SEQ ID NO:1-319; 97% sequence identity with any of SEQ ID NO:1-319; 98% sequence identity with any of SEQ ID NO:1-319; or 99% sequence identity with any of SEQ ID NO:1-319.

"% sequence identity" refers to a relationship between two or more sequences, as determined by comparing the sequences. In the art, "identity" also means the degree of sequence relatedness between peptide sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters which originally load with the software when first initialized.

"D-substituted analogs" include RgIA analogs disclosed herein having one or more L-amino acids substituted with D-amino acids. The D-amino acid can be the same amino acid type as that found in the analog sequence or can be a different amino acid. Accordingly, D-analogs are also variants.

"Modifications" include RgIA analogs disclosed herein wherein one or more amino acids have been replaced with a non-amino acid component, or where the amino acid has been conjugated to a functional group or a functional group has been otherwise associated with an amino acid. The modified amino acid may be, e.g., a glycosylated amino acid, a PEGylated amino acid (covalent and non-covalent attachment or amalgamation of polyethylene glycol (PEG) polymers), a farnesylated amino acid, an acetylated amino acid, an acylated amino acid, a biotinylated amino acid, a phosphorylated amino acid, an amino acid conjugated to a lipid moiety such as a fatty acid, or an amino acid conjugated to an organic derivatizing agent. The presence of modified amino acids may be advantageous in, for example, (a) increasing polypeptide serum half-life and/or functional in vivo half-life, (b) reducing polypeptide antigenicity, (c) increasing polypeptide storage stability, (d) increasing peptide solubility, (e) prolonging circulating time, and/or (f) increasing bioavailability, e.g. increasing the area under the curve ($AUC_{sc}$). Amino acid(s) can be modified, for example, co-translationally or post-translationally during recombinant production (e.g., N-linked glycosylation at N-X-S/T motifs during expression in mammalian cells) or modified by synthetic means. The modified amino acid can be within the sequence or at the terminal end of a sequence. Modifications can include derivatives as described elsewhere herein.

Peptides are cleared by the kidneys or phagocytes readily and shortly after administration. Moreover, peptides are susceptible to degradation by proteolytic enzymes. Linking of conotoxin peptides to fatty acyl chains (lipidation) of different lengths and structures can increase the half-life of peptides in circulation by promoting interaction with proteins in the blood such as albumin, which act as carriers. Suitable lipidated moieties include fully saturated lipids as well as unsaturated lipids such as mono-, bis-, tris-, and poly-unsaturated lipids. In some embodiments a core lipid moiety may be conjugated with more than one conotoxin peptide. For example, two of the same conotoxin peptides may be conjugated to a single lipid moiety.

An activated ester of a fatty acid, such as a N-Hydroxysuccinimidyl ester or other activated ester derived from a fatty acid with a free carboxylic acid and a commercially available peptide coupling reagent, is mixed with the conotoxin peptide of interest that contains a free amine such as N-terminal glycine in a solvent such as dimethylformamide and a base like diisopropylethylamine. The mixture is stirred in the dark for 12-16 hours and the lipidated conotoxin peptide product is isolated by semi-preparative reversed phase chromatography.

Modifications of RgIA analogs described herein also include fusion of the peptide to the Fc domain of IgG, thus combining the biological activity of the RgIA peptides with the stability of monoclonal antibodies. As described herein, these RgIA peptibodies would be generated by recombinant technology by fusing an RgIA analog in-frame with the Fc portion of human IgG. These peptide-Fc fusion proteins generally have a molecular weight of less than 60-70 kDa, or approximately half the weight of monoclonal antibodies. Incorporation of the Fc portion of IgG in peptibodies can prolong the half-life through FcRn protection. Dimerization of two Fc regions increases the number of active peptides interacting with the target up to two-fold (Wu et al., 2014).

In certain embodiments, the peptide is fused to other domains of IgG or to albumin.

The presence of modified amino acids may be advantageous in, for example, (a) increasing peptide serum half-life and/or functional in vivo half-life, (b) reducing peptide immunogenicity, (c) increasing peptide storage stability, (d) increasing peptide solubility, (e) prolonging circulating time, (f) increasing bioavailability, e.g. increasing the area under the curve ($AUC_{sc}$), and/or (g) increased buccal or oral bioavailability by increasing mucosal absorption. Amino acid(s) can be modified, for example, co-translationally or post-translationally during recombinant production (e.g., N-linked glycosylation at N-X-S/T motifs during expression in mammalian cells) or modified by synthetic means. The modified amino acid can be within the sequence or at the terminal end of a sequence. Modifications can include derivatives as described elsewhere herein.

The C-terminus may be a carboxylic acid or an amide group. The present disclosure also relates to the RgIA analogs further modified by (i) additions made to the C-terminus, such as Tyr, iodo-Tyr, a fluorescent tag, and/or (ii) additions made to the N-terminus, such as Tyr, iodo-Tyr, pyroglutamate, or a fluorescent tag.

In addition, residues or groups of residues known to the skilled artisan to improve stability can be added to the C-terminus and/or N-terminus. Also, residues or groups of residues known to the skilled artisan to improve oral availability can be added to the C-terminus and/or N-terminus.

In certain embodiments, modification of the N-terminus includes acylation including N-formyl, N-acetyl, N-propyl, and long chain fatty acid groups. In certain embodiments modification of the N-terminus includes addition of a PYRO group. In certain embodiments, modification of the C-terminus and/or N-terminus includes fattylation by the addition of fatty acids 4 to 24, 10 to 18, or 12 to 16 carbon atoms in length.

In certain embodiments, modification of the peptide includes linkage of the peptide to fluorescent labels, including fluorescent dyes.

In certain embodiments, modification of the peptide includes replacement of one or more of the disulfide bonds with one or more of the following: dicarba bridges as alkane (via hydrogenation of alkene), Z-alkene, E-alkene, thioether, selenoether, trisulfide, tetrasulfide, polyethoxy ether, aliphatic linkers, and/or a combination of aliphatic linker with one or more alkene moieties (Z- or E-isomers) that are synthesized via ring-closing metathesis reactions.

In certain embodiments, modification of the peptide includes PEGylation. PEGylation consists of the addition of one or more poly-(ethylene glycol) (PEG) molecules to a peptide or protein, and often enhances protein and peptide delivery (Davies et al., 1977). Peptides are cleared by the kidneys phagocytes readily and shortly after administration. Moreover, peptides are susceptible to degradation by proteolytic enzymes in the blood. Linking of conopeptides to polyethyelen glycol (PEG) of different lengths and structures can increase the half-life of peptides in circulation. PEGylation increases the molecular weight of the peptide and thus reduces the rate with which it is filtrated in the kidneys; PEGylation can also shield the peptide from proteases and macrophages and other cells of the reticuloendothelial system (RES) that can remove it. In addition, PEGylation may reduce any immunogenicity associated with a foreign peptide.

An example of how conotoxin peptides can be conjugated to PEG is conjugation of a methoxy poly(ethylene glycol)-succinimidyl valerate to conotoxin peptide RgIA analog CSP-4-NH2 (SEQ ID NO:25). 5-10 mg of conotoxin peptide and mPEG-butyraldehyde are reacted at a 1.5:1 molar ratio by stirring in 0.25 mL of anhydrous dimethyl formamide in the presence of 0.0026 mL N,N-diisopropylethylamine at room temperature for 16 hours in the dark. Reaction completeness and the concentration of PEGylated conotoxin peptide is measured by reverse phase chromatography using a Poroshell C18 column. In another type of PEG conjugation reaction, a methoxy poly(ethylene glycol) (i.e., PEG)-butyr-aldehyde is joined to a conotoxin peptide. 5-10 mg of conotoxin peptide CSP-4-NH2 and mPEG-butyraldehyde are reacted at a 1.5:1 molar ratio by stirring in 0.2 mL of 100% methanol at room temperature for 15 minutes. An aqueous solution of sodium cyanoborohydride to a final concentration of 1 mg/mL, followed by mixing 16 hours at room temperature in the dark. Reaction completeness and the concentration of PEGylated-conotoxin peptide is measured by reverse phase chromatography using a Poroshell C18 column. mPEG-conjugated conotoxin peptides are purified by removal of excess conotoxin peptide by centrifugation in a desalting column. Samples are centrifuged at 1000×g for 2 minutes in a methanol-equilibrated Zeba Spin desalting column, (2 mL volume, 7,000 molecular weight cut-off, ThermoScientific). Reaction completeness and the concentration of PEGylated conotoxin peptide in spun-through material is measured by reverse phase chromatography using a Poroshell C18 column.

The present disclosure is further directed to derivatives of the disclosed RgIA analogs. Derivatives include RgIA analogs having cyclic permutations in which the cyclic permutants retain the native bridging pattern of native conotoxin peptide (Craik, et al. (2001)), e.g., a cyclized conotoxin peptide having an amide cyclized backbone such that the conotoxin peptide has no free N- or C-terminus in which the conotoxin peptide includes the native disulfide bonds (U.S. Pat. No. 7,312,195). In one embodiment, the cyclized conotoxin peptide includes a linear conotoxin peptide and a peptide linker, wherein the N- and C-termini of the linear conotoxin peptide are linked via the peptide linker to form the amide cyclized peptide backbone. In some embodiments, the peptide linker includes amino acids selected from Gly, Ala and combinations thereof.

Various cyclization methods can be applied to the RgIA analogs described herein. The RgIA analogs described herein can be readily cyclized using alanine bridges as described in, for example, in Clark, et al., 2013, and Clark, et al., 2012. Cyclizing RgIA analogs can improve their oral bioavailability and reduce the susceptibility to proteolysis, without affecting the affinity of the RgIA analogs for their specific targets. Cyclization occurs between the N- and C-termini and disulfide bridges between C1-C3 and C2-C4, respectively, where the GAAGAG cyclization linker can be of any length between 1 and 8 amino acids and can be composed of any amino acid sequence. In certain embodiments, cyclization is done using alternative linkers such as non-peptide linkers including Polyethoxy ethers, aliphatic linkers, and/or any combination of aliphatic linker with one or more alkene moieties (Z- or E-isomers) in the hydrocarbon chain that can be synthesized via ring-closing methesis reactions.

TABLE 3

Cyclized sequences of RgIA analogs

| Sequence | SEQ ID NO. |
|---|---|
| GCCSDPRCRX3RCRGAAGAG | 13 |
| GCCTDPRCX2X3QCRGAAGAG | 14 |
| GCCTDPRCX2X3QCRRGAAGAG | 15 |
| GCCTDPRCX2X3QCYGAAGAG | 16 |
| GX4CTDPRX4X2X3QCRGAAGAG | 17 |
| GCCTDPRCRX3QCFGAAGAG | 18 |

TABLE 3-continued

Cyclized sequences of RgIA analogs

| Sequence | SEQ ID NO. |
|---|---|
| GCCTDPRCRX3QCYGAAGAG | 19 |
| GCCTDPRCRX3QCWGAAGAG | 20 |

X3 = des-X3, Ser, or Thr

Embodiments disclosed herein include the RgIA analogs described herein as well as variants, D-substituted analogs, modifications, and derivatives of the RgIA analogs described herein. In some embodiments, variants, D-substituted analogs, modifications, and derivatives have 1, 2, 3, 4, 5, 6, 7, 8, 9, 10, 11, 12, 13, 14, 15, 16, 17, or 18 sequence additions, deletions, stop positions, substitutions, replacements, conjugations, associations, or permutations. Each conotoxin peptide disclosed herein may also include additions, deletions, stop positions, substitutions, replacements, conjugations, associations, or permutations at any position including positions 1, 2, 3, 4, 5, 6, 7, 8, 9, 10, 11, 12, 13, 14, 15, 16, 17, or 18 of an analog conotoxin peptide sequence disclosed herein.

In some embodiments an Xaa position can be included in any position of an analog conotoxin peptide, wherein Xaa represents an addition, deletion, stop position, substitution, replacement, conjugation, association or permutation. In particular embodiments, each analog conotoxin peptide has 1, 2, 3, 4, 5, 6, 7, 8, 9, 10, 11, 12, 13, 14, 15, 16, 17, or 18 Xaa positions at one or more of positions 1, 2, 3, 4, 5, 6, 7, 8, 9, 10, 11, 12, 13, 14, 15, 16, 17, or 18.

An analog can have more than one change (addition, deletion, stop position, substitution, replacement, conjugation, association, or permutation) and qualify as one or more of a variant, D-substituted analog, modification, and/or derivative. That is, inclusion of one classification of analog, variant, D-substituted analog, modification and/or derivative is not exclusive to inclusion in other classifications and all are collectively referred to as "conotoxin peptides" herein.

The conotoxin peptides can be prepared using recombinant DNA technology. Conotoxin peptides may also be prepared using Merrifield solid-phase synthesis, although other equivalent chemical syntheses known in the art can also be used. Solid-phase synthesis is commenced from the C-terminus of the conotoxin peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or para-methylbenzhydrylamine (MBHA) resin. Preparation of the hydroxymethyl resin is described by Bodansky et al. (1966). Chloromethylated resins are commercially available from Bio Rad Laboratories (Richmond, Calif.). The preparation of such a resin is described by Stewart and Young (1969). BHA and MBHA resin supports are commercially available, and are generally used when the desired conotoxin peptide being synthesized has an unsubstituted amide at the C-terminus. Thus, solid resin supports may be any of those known in the art, such as one having the formulae —O—CH2-resin support, —NH BHA resin support, or —NH-MBHA resin support. When the unsubstituted amide is desired, use of a BHA or MBHA resin can be advantageous because cleavage directly gives the amide. In case the N-methyl amide is desired, it can be generated from an N-methyl BHA resin. Should other substituted amides be desired, the teaching of U.S. Pat. No. 4,569,967 can be used, or should still other groups than the free acid be desired at the C-terminus, it is possible to synthesize the conotoxin peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in Horiki et al. (1978), using KF in dimethylformamide (DMF) at about 60° C. for 24 hours with stirring, when a conotoxin peptide having free acid at the C-terminus is to be synthesized. Following the coupling of the BOC-protected amino acid to the resin support, the α-amino protecting group can be removed, as by using trifluoroacetic acid (TFA) in methylene chloride or TFA alone. The deprotection can be carried out at a temperature between 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids can be coupled step-wise in the desired order to obtain an intermediate compound or as an alternative to adding each amino acid separately in the synthesis, some of them may be coupled to one another prior to addition to the solid phase reactor. Selection of an appropriate coupling reagent is within the skill of the art. Illustrative coupling reagents include N,N'-dicyclohexylcarbodiimide (DCC, DIC, HBTU, HATU, TBTU in the presence of HoBt or HoAt).

The activating reagents used in the solid phase synthesis of peptides including conotoxin peptides are well known in the art. Examples of suitable activating reagents include carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence can be introduced into the solid-phase reactor in a twofold or more excess, and the coupling may be carried out in a medium of DMF:CH2Cl2 (1:1) or in DMF or CH2Cl2 alone. In cases where intermediate coupling occurs, the coupling procedure can be repeated before removal of the α-amino protecting group prior to the coupling of the next amino acid. The success of the coupling reaction at each stage of the synthesis, if performed manually, can be monitored by the ninhydrin reaction, as described by Kaiser, et al. (1970). Coupling reactions can be performed automatically, as on a Beckman 990 automatic synthesizer, using a program such as that reported in Rivier, et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group can be first removed using TFA/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide can be included in the reaction vessel.

Cyclization of the linear conotoxin peptide can be effected, as opposed to cyclizing the conotoxin peptide while a part of the peptido-resin, to create bonds between Cys residues. To effect such a disulfide cyclizing linkage, a fully protected conotoxin peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the conotoxin peptide from the above resins or a benzhydrylamine (BHA) resin or a methylbenzhydrylamine (MBHA), can take place at 0° C. with hydrofluoric acid (HF) or TFA, followed by oxidation as described above.

The conotoxin peptides can also be synthesized using an automatic synthesizer. In these embodiments, amino acids can be sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodiimide in N-methylpyrrolidinone (NMP) or by 2-(1H-benzotriazole-1-yl)-1,1,3,3-tetramethyluronium hexafluorophosphate (HBTU) and diethylisopropylethylamine (DIEA). The Fmoc protecting group can be removed by treatment with a 20% solution of piperidine in dimethylformamide (DMF). Resins are subsequently washed with DMF (twice), followed by methanol and NMP.

Conotoxin peptides can be formulated within pharmaceutical compositions. "Pharmaceutical compositions" mean physically discrete coherent units suitable for medical administration. "Pharmaceutical composition in dosage unit form" means physically discrete coherent units suitable for medical administration, each containing a therapeutically effective amount, or a multiple (up to four times) or sub-multiple (down to a fortieth) of a therapeutically effective amount of a conotoxin peptide with a pharmaceutically acceptable carrier. Whether the pharmaceutical composition contains a daily dose, or for example, a half, a third or a quarter of a daily dose, will depend on whether the pharmaceutical composition is to be administered once or, for example, twice, three times, or four times a day, respectively.

The amount and concentration of a conotoxin peptide in a pharmaceutical composition, as well as the quantity of the pharmaceutical composition can be selected based on clinically relevant factors, the solubility of the conotoxin peptide in the pharmaceutical composition, the potency and activity of the conotoxin peptide, and the manner of administration of the pharmaceutical composition. It is only necessary that the conotoxin peptide constitute a therapeutically effective amount, i.e., such that a suitable effective dosage will be consistent with the dosage form employed in single or multiple unit doses.

The pharmaceutical compositions will generally contain from 0.0001 to 99 wt. %, preferably 0.001 to 50 wt. % or from 0.01 to 10 wt. % of the conotoxin peptide by weight of the total composition. In addition to the conotoxin peptide, the pharmaceutical compositions can also contain other drugs or agents. Examples of other drugs or agents include analgesic agents, cytokines, and therapeutic agents in all of the major areas of clinical medicine. When used with other drugs or agents, the conotoxin peptides may be delivered in the form of drug cocktails. A cocktail is a mixture of any one of the conotoxin peptides with another drug or agent. In this embodiment, a common administration vehicle (e.g., pill, tablet, implant, pump, injectable solution, etc.) would contain both the conotoxin peptide in combination with the other drugs or agents. The individual components of the cocktail can each be administered in therapeutically effective amounts or their administration in combination can create a therapeutically effective amount.

Pharmaceutical compositions include pharmaceutically acceptable carriers including those that do not produce significantly adverse, allergic, or other untoward reactions that outweigh the benefit of administration, whether for research, prophylactic, and/or therapeutic treatments. Illustrative pharmaceutically acceptable carriers and formulations are disclosed in Remington, 2005. Moreover, pharmaceutical compositions can be prepared to meet sterility, pyrogenicity, and/or general safety and purity standards as required by U.S. Food and Drug Administration (FDA) Office of Biological Standards, and/or other relevant regulatory agencies.

Typically, a conotoxin peptide will be admixed with one or more pharmaceutically acceptable carriers chosen for the selected mode of administration. For examples of delivery methods see U.S. Pat. No. 5,844,077.

Illustrative generally used pharmaceutically acceptable carriers include any and all bulking agents, fillers, solvents, co-solvents, dispersion media, coatings, surfactants, antioxidants, preservatives, isotonic agents, releasing agents, absorption delaying agents, salts, stabilizers, buffering agents, chelating agents, gels, binders, disintegration agents, wetting agents, emulsifiers, lubricants, coloring agents, flavoring agents, sweetening agents, and perfuming agents.

Illustrative buffering agents include citrate buffers, succinate buffers, tartrate buffers, fumarate buffers, gluconate buffers, oxalate buffers, lactate buffers, acetate buffers, phosphate buffers, histidine buffers, and trimethylamine salts.

Illustrative preservatives include phenol, benzyl alcohol, meta-cresol, methyl paraben, propyl paraben, octadecyldimethylbenzyl ammonium chloride, benzalkonium halides, hexamethonium chloride, alkyl parabens, methyl paraben, propyl paraben, catechol, resorcinol, cyclohexanol, and 3-pentanol.

Illustrative isotonic agents include polyhydric sugar alcohols, trihydric sugar alcohols, or higher sugar alcohols, such as glycerin, erythritol, arabitol, xylitol, sorbitol, and mannitol.

Illustrative stabilizers include organic sugars, polyhydric sugar alcohols, polyethylene glycol, sulfur-containing reducing agents, amino acids, low molecular weight peptides, immunoglobulins, hydrophilic polymers, and polysaccharides.

Illustrative antioxidants include ascorbic acid, methionine, vitamin E, cysteine hydrochloride, sodium bisulfite, sodium metabisulfite, sodium sulfite, oil soluble antioxidants, ascorbyl palmitate, butylated hydroxyanisole (BHA), butylated hydroxytoluene (BHT), lecithin, propyl gallate, alpha-tocopherol, metal chelating agents, citric acid, ethylenediamine tetraacetic acid (EDTA), sorbitol, tartaric acid, and phosphoric acid.

Illustrative lubricants include sodium lauryl sulfate and magnesium stearate.

Illustrative pharmaceutically acceptable salts include acidic and/or basic salts, formed with inorganic or organic acids and/or bases, preferably basic salts. While pharmaceutically acceptable salts are preferred, particularly when employing the conotoxin peptides as medicaments, other salts find utility, for example, in processing these conotoxin peptides, or where non-medicament-type uses are contemplated. Salts of these conotoxin peptides may be prepared by techniques recognized in the art.

Illustrative pharmaceutically acceptable salts include inorganic and organic addition salts, such as hydrochloride, sulphates, nitrates, phosphates, acetates, trifluoroacetates, propionates, succinates, benzoates, citrates, tartrates, fumarates, maleates, methane-sulfonates, isothionates, theophylline acetates, and salicylates. Lower alkyl quaternary ammonium salts can also be used.

For oral administration, the conotoxin peptides can be formulated into solid or liquid preparations such as capsules, pills, tablets, lozenges, melts, powders, suspensions, or emulsions. In preparing the compositions in oral dosage form, any of the usual pharmaceutically acceptable carriers may be employed, such as, for example, carriers such as starches, sugars, diluents, granulating agents, lubricants, binders, disintegrating agents, and the like in the case of oral solid preparations (such as, for example, powders, capsules and tablets); or water, glycols, oils, alcohols, flavoring agents, preservatives, coloring agents, suspending agents, and the like in the case of oral liquid preparations (such as, for example, suspensions, elixirs and solutions). Because of their ease in administration, tablets and capsules can represent an advantageous oral dosage unit form, in which case solid pharmaceutical carriers are obviously employed. If desired, tablets may be sugar-coated or enteric-coated by standard techniques. The conotoxin peptide can be encapsulated to make it stable to passage through the gastrointestinal tract while at the same time, in certain embodiments, allowing for passage across the blood brain barrier. See for example, WO 96/11698.

For parenteral administration, the conotoxin peptides may be dissolved in a pharmaceutically acceptable carrier and administered as either a solution or a suspension. Illustrative pharmaceutically acceptable carriers include water, saline, dextrose solutions, fructose solutions, ethanol, or oils of animal, vegetative, or synthetic origin. The carrier may also contain other ingredients, for example, preservatives, suspending agents, solubilizing agents, buffers, and the like.

The conotoxin peptides can be in powder form for reconstitution in the appropriate pharmaceutically acceptable carrier at the time of delivery. In another embodiment, the unit dosage form of the conotoxin peptide can be a solution of the conotoxin peptide, or a pharmaceutically acceptable salt thereof, in a suitable diluent in sterile, hermetically sealed ampoules or sterile syringes.

Conotoxin peptides can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts.

Additionally, conotoxin peptides can be formulated as sustained-release systems utilizing semipermeable matrices of solid polymers containing at least one compound. Various sustained-release materials have been established and are well known by those of ordinary skill in the art. Sustained-release systems may, depending on their chemical nature, release conotoxin peptides following administration for a few weeks up to over 100 days.

Administration of the conotoxin peptide can also be achieved using pumps (see, e.g., Luer et al., (1993), Zimm, et al. (1984) and Ettinger, et al. (1978)); microencapsulation (see, e.g., U.S. Pat. Nos. 4,352,883, 4,353,888, and 5,084,350); continuous release polymer implants (see, e.g., U.S. Pat. No. 4,883,666); and macroencapsulation (see, e.g., U.S. Pat. Nos. 5,284,761, 5,158,881, 4,976,859, and 4,968,733 and published PCT patent applications WO92/19195, WO 95/05452);

When the conotoxin peptides are administered intrathecally, they may also be dissolved in cerebrospinal fluid.

Naked or unencapsulated cell grafts to the CNS can also be used. See, e.g., U.S. Pat. Nos. 5,082,670 and 5,618,531.

The conotoxin peptides of the present disclosure, and pharmaceutical compositions thereof, are useful in methods of treating conditions associated with the α9α10 receptor subtype of the nicotinic acetylcholine receptor (nAChR) in a subject. The activity of certain α-conotoxins, including RgIA and its analogs, in blocking the α9α10 subtype of nAChR has been shown herein in studies using oocytes that express different subtypes of the nAChR (Ellison et al., 2006; Vincler et al., 2006; WO 2008/011006; US 2009/0203616; US 2012/0220539). The activity of α-conotoxins, including RgIA, as an antinociceptive and an analgesic has been shown in studies of chronic constriction injury (Vincler, et al., 2006; WO 2008/011006; US 2009/0203616). The activity of α-conotoxins, including RgIA, in inhibiting migration of immune cells has been shown in studies of chronic constriction injury (Vincler, et al., 2006; WO 2008/011006; US 2009/0203616).

Methods described herein include administering to a subject in need thereof a therapeutically effective amount of a disclosed conotoxin peptide or a pharmaceutically acceptable salt thereof, wherein the disclosed conotoxin peptide blocks the α9α10 subtype of the nAChR. Conotoxin peptides that block the α9α10 subtype of nAChR are useful for treating pain, for treating inflammation and/or inflammatory conditions and for treating cancers and/or cancer related pain. In certain embodiments, the conotoxin peptides are effective based on their ability to inhibit the migration of immune cells. In other embodiments, the compounds are effective based on their ability to slow demyelination and/or increase the number of intact nerve fibers.

Methods disclosed herein include treating subjects (humans, veterinary animals (dogs, cats, reptiles, birds, etc.), livestock (horses, cattle, goats, pigs, chickens, etc.), and research animals (monkeys, rats, mice, fish, etc.)) with conotoxin peptides disclosed herein including pharmaceutically-acceptable salts and prodrugs thereof. Treating subjects includes delivering therapeutically effective amounts of the disclosed conotoxin peptides. Therapeutically effective amounts include those that provide effective amounts, prophylactic treatments, and/or therapeutic treatments.

An "effective amount" is the amount of a conotoxin peptide necessary to result in a desired physiological change in the subject. Effective amounts are often administered for research purposes. Effective amounts disclosed herein result in a desired physiological change in a research assay intended to study the effectiveness of a conotoxin peptide in the treatment of pain, inflammatory conditions, inflammation, and/or cancer.

A "prophylactic treatment" includes a treatment administered to a subject who does not display signs or symptoms of pain, an inflammatory condition, inflammation, and/or cancer or a subject who displays only early signs or symptoms of pain, an inflammatory condition, inflammation, and/or cancer such that treatment is administered for the purpose of diminishing, preventing, or decreasing the risk of developing the pain, inflammatory condition, inflammation, and/or cancer further. Thus, a prophylactic treatment functions as a preventative treatment against pain, an inflammatory condition, inflammation, and/or cancer.

A "therapeutic treatment" includes a treatment administered to a subject who displays symptoms or signs of pain, an inflammatory condition, inflammation, and/or cancer and is administered to the subject for the purpose of diminishing or eliminating those signs or symptoms of the pain, inflammatory condition, inflammation, and/or cancer. The therapeutic treatment can reduce, control, or eliminate the presence or activity of pain, an inflammatory condition, inflammation, and/or cancer and/or reduce control or eliminate side effects of pain, an inflammatory condition, inflammation, and/or cancer.

Illustrative types of pain that can be treated include general pain, chronic pain, neuropathic pain, nociceptive pain, and inflammatory pain. In addition, these types of pain can be associated with and/or induced by causes including: peripheral nerve or nociceptor damage, inflammatory conditions, metabolic disorders, virus infection, cancers, pain induced by chemotherapeutic agents, pain induced after surgical procedure, and pain induced by burn or other physical tissue injury.

Therapeutically effective amounts in the treatment of chemotherapy-induced neuropathic pain (CINP) can include those that decrease mechanical hyperalgesia, mechanical allodynia (pain due to a stimulus that does not normally cause pain), thermal (heat-induced) hyperalgesia, thermal (cold-induced) allodynia, the number of migrating immune cells, levels of inflammatory mediators, and/or subject-reported subjective pain levels.

Therapeutically effective amounts in the treatment of burn-induced neuropathic pain can include those that decrease mechanical hyperalgesia, mechanical allodynia, thermal (heat-induced) hyperalgesia, thermal (cold-induced) allodynia, the number of migrating immune cells, levels of inflammatory mediators, and/or subject-reported subjective pain levels.

Therapeutically effective amounts in the treatment of post-operative neuropathic pain can include those that decrease mechanical hyperalgesia, mechanical allodynia, thermal (heat-induced) hyperalgesia, thermal (cold-induced) allodynia, the number of migrating immune cells, levels of inflammatory mediators, and/or subject-reported subjective pain levels.

Illustrative inflammatory conditions that can be treated include inflammation, chronic inflammation, rheumatic diseases (including arthritis, lupus, ankylosing spondylitis, fibromyalgia, tendonitis, bursitis, scleroderma, and gout), sepsis, fibromyalgia, inflammatory bowel disease (including ulcerative colitis and Crohn's disease), sarcoidosis, endometriosis, uterine fibroids, inflammatory skin diseases (including psoriasis and impaired wound healing), inflammatory conditions of the lungs (including asthma and chronic obstructive pulmonary disease), diseases associated with inflammation of the nervous system (including multiple sclerosis, Parkinson's Disease and Alzheimer's Disease), periodontal disease, and cardiovascular disease.

Therapeutically effective amounts in the treatment of inflammatory conditions can include those that decrease levels of inflammatory markers at the gene expression or protein level and/or reduce the number of migrating immune cells. In addition, pain associated with inflammatory conditions can be treated by therapeutically effective amounts that result in the decrease of mechanical hyperalgesia, mechanical allodynia, thermal (heat-induced) hyperalgesia, thermal (cold-induced) allodynia, and/or subject-reported subjective pain levels.

Illustrative cancers that can be treated include breast cancers. $\alpha$9-nAChR is overexpressed in human breast tumor tissue (Lee et al., 2010a) and receptor inhibition by siRNA or other mechanism reduced in vitro and in vivo carcinogenic properties of breast cancer cells, including inhibition of cancer cell proliferation (Chen et al., 2011). In certain embodiments, RgIA analogs are used in therapeutic amounts in order to inhibit tumor growth by inhibition of $\alpha$9-nAChR.

Therapeutically effective amounts in the treatment of cancers, such as breast cancers, can include those that decrease a number of tumor cells, decrease the number of metastases, decrease tumor volume, increase life expectancy, induce apoptosis of cancer cells, induce cancer cell death, induce chemo- or radiosensitivity in cancer cells, inhibit angiogenesis near cancer cells, inhibit cancer cell proliferation cells, inhibit tumor growth cells, prevent metastasis, prolong a subject's life, reduce cancer-associated pain, and/or reduce relapse or re-occurrence of the cancer in a subject following treatment.

For administration, therapeutically effective amounts can be initially estimated based on results from in vitro assays and/or animal model studies. For example, a dose can be formulated in animal models to achieve a circulating concentration range that includes an IC50 as determined in cell culture against a particular target. Such information can be used to more accurately determine therapeutically effective amounts in subjects of interest.

The actual amount administered to a particular subject as a therapeutically effective amount can be determined by a physician, veterinarian, or researcher taking into account parameters such as physical and physiological factors including target; body weight; severity of condition; type of pain, inflammatory condition, or cancer; previous or concurrent therapeutic interventions; idiopathy of the subject; and route of administration.

Dosage may be adjusted appropriately to achieve desired conotoxin peptide levels, locally or systemically. Typically the conotoxin peptides of the present disclosure exhibit their effect at a dosage range from 0.001 mg/kg to 250 mg/kg, preferably from 0.01 mg/kg to 100 mg/kg of the conotoxin peptide, more preferably from 0.05 mg/kg to 75 mg/kg. A suitable dose can be administered in multiple sub-doses per day. Typically, a dose or sub-dose may contain from 0.1 mg to 500 mg of the conotoxin peptide per unit dosage form. A more preferred dosage will contain from 0.5 mg to 100 mg of conotoxin peptide per unit dosage form.

Additional doses which are therapeutically effective amounts can often range from 0.1 to 5 μg/kg or from 0.5 to 1 μg/kg. In other examples, a dose can include 1 μg/kg, 5 μg/kg, 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, 80 μg/kg, 85 μg/kg, 90 μg/kg, 95 μg/kg, 100 μg/kg, 150 μg/kg, 200 μg/kg, 250 μg/kg, 350 μg/kg, 400 μg/kg, 450 μg/kg, 500 μg/kg, 550 μg/kg, 600 μg/kg, 650 μg/kg, 700 μg/kg, 750 μg/kg, 800 μg/kg, 850 μg/kg, 900 μg/kg, 950 μg/kg, 1000 μg/kg, 0.1 to 5 mg/kg, or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or more.

In particular embodiments, dosages can be initiated at lower levels and increased until desired effects are achieved. In the event that the response in a subject is insufficient at such doses, even higher doses (or effective higher doses by a different, more localized delivery route) may be employed to the extent that subject tolerance permits. Continuous dosing over, for example, 24 hours, or multiple doses per day are contemplated to achieve appropriate systemic levels of conotoxin peptide.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months, or yearly.

A variety of administration routes are available. The particular mode selected can depend upon the particular conotoxin peptide delivered, the severity of pain, inflammatory condition or cancer being treated, and the dosage required to provide a therapeutically effective amount. Any mode of administration that is medically acceptable, meaning any mode that provides a therapeutically effective amount of the conotoxin peptide without causing clinically unacceptable adverse effects that outweigh the benefits of administration according to sound medical judgment, can be used. Illustrative routes of administration include intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual administration and more particularly by intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual injection.

In one embodiment, the conotoxin peptide is delivered directly into the central nervous system (CNS), preferably to the brain ventricles, brain parenchyma, the intrathecal space, or other suitable CNS location.

Alternatively, targeting therapies may be used to deliver the conotoxin peptide more specifically to certain types of cell, by the use of targeting systems such as antibodies or cell specific ligands.

Conotoxin peptides can also be administered in a cell based delivery system in which a nucleic acid sequence encoding the conotoxin peptide is introduced into cells designed for implantation in the body of the subject. In particular embodiments, this delivery method can be used in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959, and WO 97/12635.

Suitable nucleic acid sequences can be prepared synthetically for each conotoxin peptide on the basis of the disclosed sequences and the known genetic code. In some embodiments, the polynucleotide includes a plasmid, a cDNA, or an mRNA that can include, e.g., a sequence (e.g., a gene) for expressing a conotoxin peptide. Suitable plasmids include standard plasmid vectors and minicircle plasmids that can be used to transfer a gene to a cell. The polynucleotides (e.g., minicircle plasmids) can further include any additional sequence information to facilitate transfer of the genetic material (e.g., a sequence encoding a conotoxin peptide) to a cell. For example, the polynucleotides can include promoters, such as general promoters, tissue-specific promoters, cell-specific promoters, and/or promoters specific for the nucleus or cytoplasm. Promoters and plasmids (e.g., minicircle plasmids) are generally well known in the art and can be prepared using conventional techniques. As described further herein, the polynucleotides can be used to transfect cells. Unless otherwise specified, the terms transfect, transfected, or transfecting can be used to indicate the presence of exogenous polynucleotides or the expressed polypeptide therefrom in a cell. A number of vectors are known to be capable of mediating transfer of genes to cells, as is known in the art.

Briefly, the term "gene" refers to a nucleic acid sequence that encodes a conotoxin peptide. This definition includes various sequence polymorphisms, mutations, and/or sequence variants wherein such alterations do not affect the function of the encoded conotoxin peptide. The term "gene" may include not only coding sequences but also regulatory regions such as promoters, enhancers, and termination regions. "Gene" further can include all introns and other DNA sequences spliced from the mRNA transcript, along with variants resulting from alternative splice sites. Nucleic acid sequences encoding the conotoxin peptide can be DNA or RNA that directs the expression of the conotoxin peptide. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Gene sequences to encode conotoxin peptide disclosed herein are available in publicly available databases and publications.

As stated, conotoxin peptides disclosed herein block the α9α10 subtype of the nAChR. Blocking can be measured by any effective means. In one embodiment, blocking is measured as the displacement of labeled RgIA from the α9α10 subtype of the nAChR by a conotoxin peptide disclosed herein. In one embodiment, blocking can be a 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% displacement of labeled RgIA from the α9α10 subtype of the nAChR by a conotoxin peptide disclosed herein.

In a second embodiment, blocking can be measured by conducting a biological assay on a conotoxin peptide disclosed herein to determine its therapeutic activity as compared to the results obtained from the biological assay of RgIA. In one embodiment, blocking can be 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% greater therapeutic activity of conotoxin peptide disclosed herein when compared to RgIA as measured by the biological assay.

In a third embodiment, the binding affinity of a conotoxin peptide disclosed herein to the α9α10 subtype of the nAChR can be measured and compared to the binding affinity of RgIA to the α9α10 subtype of the nAChR. In one embodiment, blocking can be a 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% greater binding affinity of the conotoxin peptide disclosed herein over RgIA.

In a fourth embodiment, the effect of a conotoxin peptide disclosed herein on the function of the α9α10 subtype of the nAChR is analyzed by measuring the effect in functional assays, such as electrophysiological assays, calcium imaging assays, and the like. In one embodiment, blocking includes a 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% reduction in the function of the α9α10 subtype of the nAChR as measured by a functional assay when compared to RgIA.

Conotoxin peptides disclosed herein are also useful in methods of identifying drug candidates for use in treating conditions associated with the α9α10 subtype of the nAChR. These methods include screening a drug candidate for its ability to block the activity of the α9α10 subtype of the nAChR.

"Drug candidate" refers to any peptide (including antibodies or antibody fragments) or compound (small molecule or otherwise) that may block or otherwise interfere with the activity of a target (i.e. the α9α10 subtype). Small molecules may belong to any chemical class suspected to interact with a peptide complex and expected to be pharmaceutically acceptable. Drug candidates can be found in nature, synthesized by combinatorial chemistry approaches, and/or created via rational drug design.

Blocking can be measured as described elsewhere herein except that the drug candidate can be compared to conotoxin peptides disclosed herein rather than or in addition to RgIA. Conotoxin peptides are useful in methods of identifying drug candidates that mimic the therapeutic activity of the conotoxin peptide. Such methods include the steps of: (a) conducting a biological assay on a drug candidate to determine its therapeutic activity; and (b) comparing the results obtained from the biological assay of the drug candidate to the results obtained from the biological assay of a conotoxin peptides disclosed herein.

Drug candidates may also interfere with the activity of the α9α10 subtype through interaction with polynucleotides (e.g. DNA and/or RNA), and/or enzymes. Such drug candidates can be known or potential DNA modifying agents, including DNA damaging agents (e.g. intercalating agents that interfere with the structure of nucleic acids); DNA binding agents; mismatch binding proteins; and/or alkylating agents.

One goal of rational drug design is to identify drug candidates which are, for example, more active or stable forms of the conotoxin peptide, or which, e.g., enhance or interfere with the function of a peptide in vivo. Several approaches for use in rational drug design include analysis of three-dimensional structure, alanine scans, molecular modeling, and use of anti-id antibodies. Such techniques may include providing atomic coordinates defining a three-dimensional structure of a protein complex formed by the conotoxin peptide and the α9α10 subtype of the nAChR, and designing or selecting drug candidates capable of interfering with the interaction between a conotoxin peptide and the α9α10 subtype of the nAChR based on the atomic coordinates.

Once a drug candidate is selected for further study or development, its structure can be modeled according to its physical properties, e.g., stereochemistry, bonding, size, and/or charge, using data from a range of sources, e.g., spectroscopic techniques, x-ray diffraction data, and NMR. Computational analysis, similarity mapping (which models the charge and/or volume of a drug candidate, rather than the bonding between atoms), and other techniques can be used in this modeling process.

When a drug candidate is selected, attachment of further chemical groups can be evaluated. Chemical groups can be selected so that the drug candidate is easy to synthesize, is likely to be pharmacologically acceptable, and does not degrade in vivo, while, in some embodiments, retaining or improving the biological activity of a lead conotoxin peptide. Alternatively, where the drug candidate is peptide-based, further stability can be achieved by cyclizing the peptide, which increases its rigidity. The drug candidates with attached chemical groups can be further screened to see ensure they retain target properties. Further optimization or modification can then be carried out to arrive at one or more final drug candidates for in vivo or clinical testing.

Following selection and optimization of a drug candidate, the selected and optimized drug candidate may be manufactured and/or used in a pharmaceutical composition for administration to subjects.

The Examples below are included to demonstrate particular embodiments. Those of ordinary skill in the art should recognize in light of the present disclosure that many changes can be made to the specific embodiments disclosed herein and still obtain a like or similar result without departing from the spirit and scope of the disclosure.

EXAMPLES

Example 1. Amidation of the C-Terminus Increases the Stability of RgIA Analogs

Figure 2A:
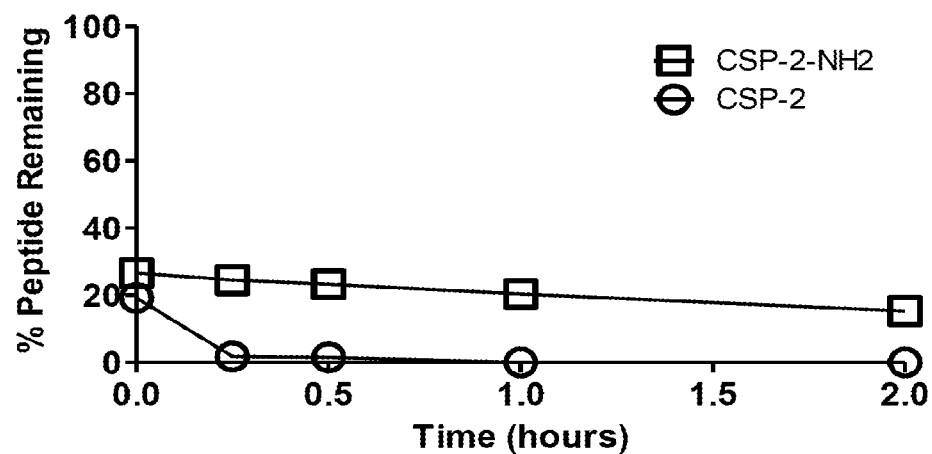
FIG. 2A and FIG. 2B show increased stability of CSP-2 (SEQ ID NO:3) and CSP-4 (SEQ ID NO:5), respectively, in serum following amidation of the C-terminus.

The replacement of the hydroxyl group in the carboxyl group of the C-terminus of peptides by an amide group was done for two RgIA analogs to increase stability. CSP-2 (SEQ ID NO:3) was considerably more stable, as evidenced by the higher percentage of the peptide remaining, in a biological matrix when the C-terminus was amidated (i.e., addition of NH2 to the C-terminus) compared to the original carboxyl group (FIG. 2A). A similar finding was made with CSP-4 (SEQ ID NO:5) and shown in FIG. 2B.

Selected illustrative peptide sequences with amidation of the C-terminus to increase stability are described in Table 6.

TABLE 6

Peptide sequences with amidation of C-terminus

| Sequence | SEQ ID NO. |
|---|---|
| GCCSDPRCRYRCR-amide | 21 |
| GCCSDPRCRX12RCR-amide | 22 |
| GCCTDPRCX11X12QCR-amide | 23 |
| GCCTDPRCX11X12QCRRR-amide | 24 |
| GCCTDPRCX11X12QCY-amide | 25 |
| GX13CTDPRX13X11X12QCR-amide | 26 |
| GCCTDPRCRX12QCF-amide | 27 |
| GCCTDPRCRX12QCY-amide | 28 |
| GCCTDPRCRX12QCW-amide | 29 |

X11 = Citrulline
X12 = 3-iodo-Tyrosine
X13 = Selenocysteine

Example 2. Lipidation of Conotoxin Peptides

Lipidated-succinimidyl valerate was conjugated CSP-4-NH2 (SEQ ID NO:25). 5-10 mg of conotoxin peptide and lipidated succinimidyl valerate were reacted at a 1.5:1 molecular weight ratio by stirring in 0.25 mL of anhydrous dimethyl formamide in the presence 0.0026 mL N,N-diisopropylethylamine at room temperature for 16 hours in the dark. Reaction completeness and the concentration of lipidated conotoxin peptide is measured by reverse phase chromatography using a Poroshell C18 column. Lipidated conotoxin peptide in dimethyl formamide is purified by reverse phase chromatography over a Hypersep C18 column with a gravity feed. The sample is loaded onto a calibrated column in 95% H$_2$O/5% methanol/0.1% formic acid. The column is loaded in the same buffer. The sample is eluted in four bed-volume fractions of 95% methanol/5% H$_2$O/0.1% formic acid. Fractions shown to contain lipidated conotoxin peptide by reverse phase chromatography using a Poroshell C18 column are pooled, lyophilized, and resuspended in methanol.

Figure 2B:
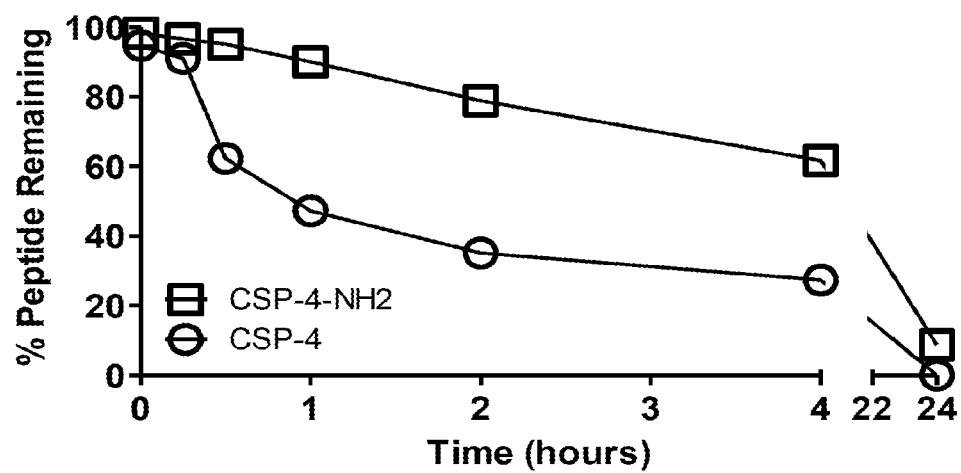
Figure 6:
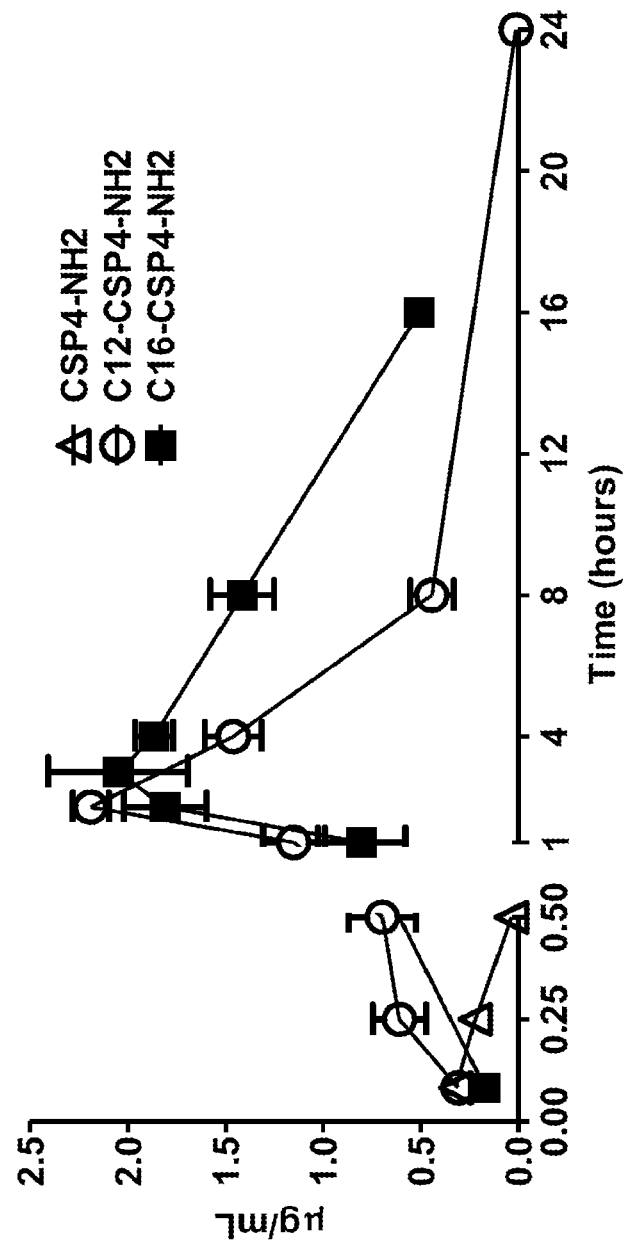
FIG. 6 shows pharmacokinetics of CSP-4-NH2 and lipidated analogs of CSP-4-NH2 measured in plasma. CSP-4-NH2 (Δ), C12-CSP-4-NH2 (○) and C16-CSP-4-NH2 (■) were administered subcutaneously to mice (500 mg/Kg). Mice, n=3. Error bars represent Standard Error of the Mean (S.E.M.) of the three samples. CX- represents a lipid moiety of length X conjugated to the CSP.

FIG. 6 shows the pharmacokinetic and pharmacodynamic properties of peptide drugs increased by lipidation. FIG. 6 shows an increased in concentration of CSP-4-NH2 when conjugated to a 12 or 16 carbon lipid. Stability of CSP-4-NH2 is also shown in FIG. 2B. Lipidation of CSP-4-NH2 by an activated ester of a 12 carbon fatty acid creates C12-CSP-4-NH2 and lipidation by an activated ester of a 16 carbon fatty acid creates C16-CSP-4-NH2. C12-CSP-4-NH2 could be detected for up 16 h, while C16-CSP-4-NH2 could be detected for up to 24 h.

Example 3. Evaluation of Lipidated CSP-4 in Capsaicin Model

Figure 7A:
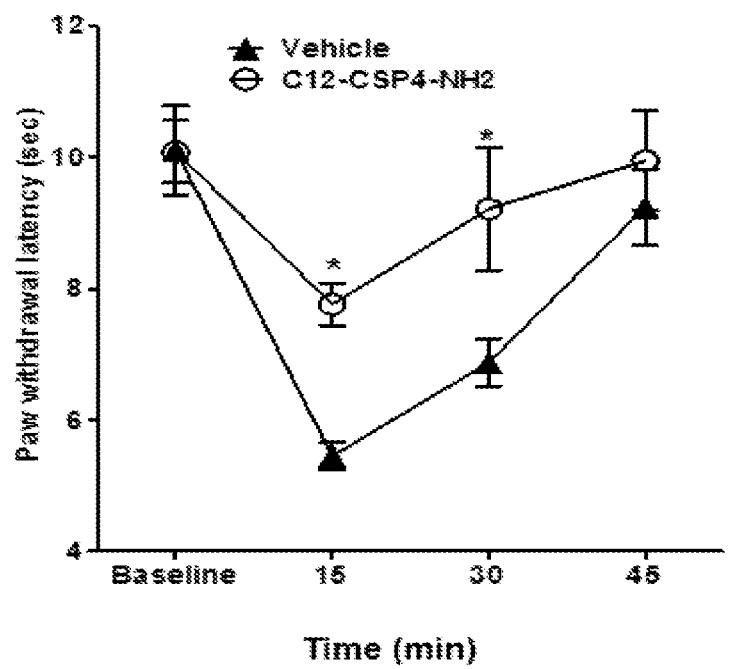
FIGS. 7A AND 7B show efficacy of lipidated CSP-4-NH2 analogs in capsaicin model of neuropathic pain. Subcutaneous administration of 500 mg/kg C12-CSP-4-NH2 (FIG. 7A) and C16-CSP-4-NH2 (FIG. 7B) was effective in reducing capsaicin-induced thermal hyperalgesia (Hargreaves test). * designates values significantly different than vehicle. $P<0.05$. Rats, n=6. Error bars represent S.E.M. of the six samples.
Figure 7B:
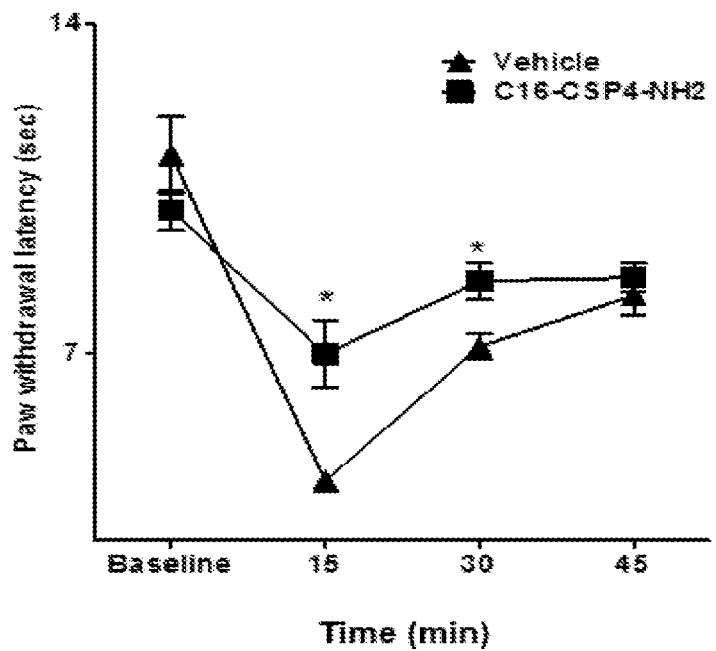

The capsaicin model of neuropathic pain was used to evaluate the therapeutic potential of RgIA analogs to treat neuropathic pain. In this model, 30 µg of Capsaicin were injected intraplantarly in the rat hindpaw to create capsaicin induced pain in the rats. Thermal hyperalgesia as measured by the Hargreaves test (a measure of sensitivity to pain; Hargreaves, et al., 1988) was performed at 15, 30, and 45 min following capsaicin injection. Paw withdrawal latency was measured prior to capsaicin injection (Baseline). C12-CSP-4-NH2, C16-CSP-4-NH2, or vehicle without peptide was subcutaneously injected 2-3 hours before the capsaicin injection. As can be seen in FIGS. 7A and 7B, injection of lipidated C12-CSP-4-NH2 and C16-CSP-4-NH2 resulted in reduction of capsaicin-induced thermal hyperalgesia.

Example 4. Evaluation of Lipidated and PEGylated CSP-4 in CINP Model

Figure 8:
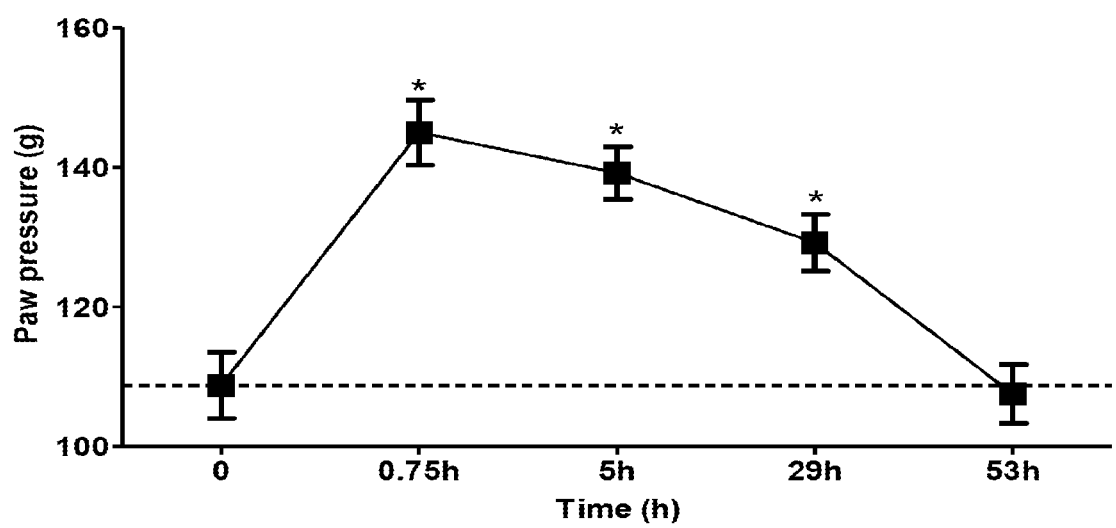
FIG. 8 shows efficacy of lipidated analog, C12-CSP-4-NH2 in a chemotherapy induced neuropathy model in rats. Mechanical hyperalgesia (t=0; Randal Selitto test) was reduced following a single subcutaneous injection of C12-CSP-4-NH2 (500 mg/Kg) that lasted 53 hours. * designates values significantly different than at time 0. $P<0.05$. Rats, n=8. Error bars represent S.E.M. of the eight samples.
Figure 9:
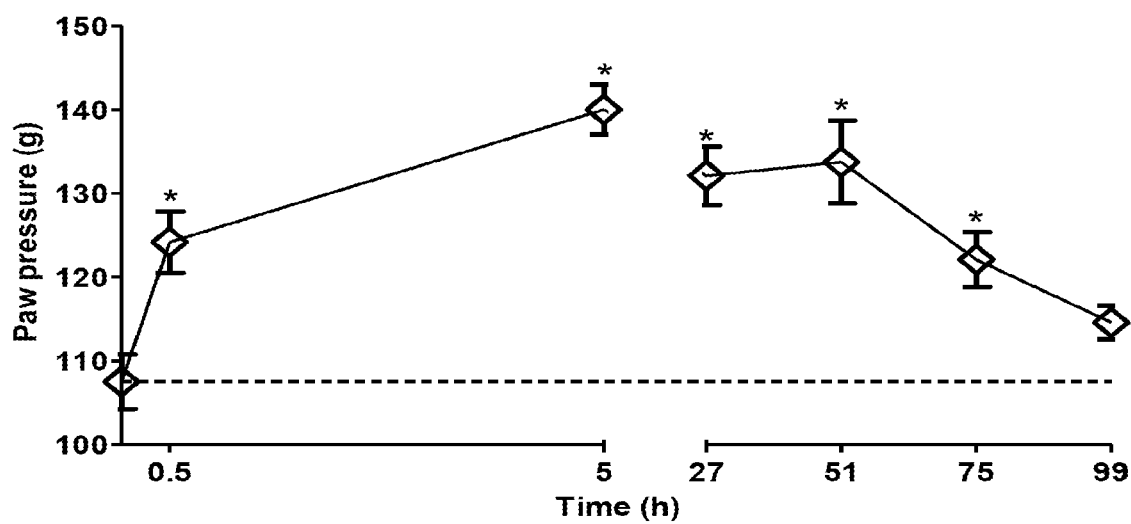
FIG. 9 shows extended pharmacotherapeutic effect of PEGylated analog of CSP-4-NH2 in chemotherapy induced neuropathic pain model. PEG-SVA-CSP-4-NH2, was effective in reducing chemotherapy-induced neuropathic pain (CINP)-mechanical hyperalgesia (t=0; Randal-Selitto test) following a single subcutaneous injection of PEG-SVA-CSP-4-NH2 (500 mg/Kg). Effect lasted 75 hours. * designates values significantly different than at time 0. $P<0.05$. Rats, n=8. Error bars represent S.E.M. of the eight samples.

CINP was induced in rats via intravenous injection of the platinum salt oxaliplatin (2.4 mg/kg) twice a week during 3 weeks. Mechanical hyperalgesia is commonly induced in the CINP model by day 14 in which the therapeutic regimen initiates. Mechanical hyperalgesia was assessed using the Randall-Selitto test. The Randall-Selitto test is a measure of sensitivity to pain. As seen in FIGS. 8 and 9, lipidation and PEGylation, respectively, resulted in a reduction in hyperalgesia in this rat model of neuropathic pain. Lipidation of CSP-4-NH2 (FIG. 8) with an activated ester of dodecanoic acid to create C12-CSP-4-NH2 provided a therapeutic benefit that lasted 29 h. PEGylation of CSP-4-NH2 (FIG. 9) with PEG-SVA to create PEG-SVA-CSP-4-NH2 extended this pharmacological therapeutic effect to over 3 days.

Exemplary Embodiments

Embodiment 1. A conotoxin peptide comprising the formula of SEQ ID NO:10.

Embodiment 2. A conotoxin peptide of embodiment 1, comprising the formula of SEQ ID NO:11.

Embodiment 3. A conotoxin peptide of embodiment 2, comprising the formula of SEQ ID NO:12.

Embodiment 4. A conotoxin peptide comprising the formula of any one from: SEQ ID NO:13-20.

Embodiment 5. A conotoxin peptide comprising the formula of any one from: SEQ ID NO: 174-185.

Embodiment 6. A conotoxin peptide of any of embodiments 1-5, wherein the C-terminus of the peptide is an amide group (—NH2).

Embodiment 7. A conotoxin peptide of any of embodiments 1-6, wherein the peptide is linked to a fatty acid.

Embodiment 8. A conotoxin peptide of embodiment 7, wherein the fatty acid is a 3 to 60 carbon fatty acid.

Embodiment 9. A conotoxin peptide of any of embodiments 1-8, wherein the amino acid at the C terminus of the conotoxin peptide is replaced by the D-amino acid stereoisomer.

Embodiment 10. A conotoxin peptide of any of embodiments 1-9, wherein the N-terminal amino acid is an acetylated amino acid.

Embodiment 11. A conotoxin peptide of any of embodiments 1-10, wherein the peptide is biotinylated.

Embodiment 12. A conotoxin peptide of any of embodiments 1-11, wherein the peptide is methylated.

Embodiment 13. A conotoxin peptide of any of embodiments 1-12, wherein the peptide is phosphorylated at one or more sites.

Embodiment 14. A conotoxin peptide of any of embodiments 1-13, wherein the peptide is glycosylated.

Embodiment 15. A conotoxin peptide of any of embodiments 1-14, wherein the peptide is linked to a fluorescent dye or a fluorescent protein.

Embodiment 16. A conotoxin peptide of any of embodiments 1-15, wherein two cysteine residues are each replaced with a natural or unnatural amino acid that are then coupled for bridge formation.

Embodiment 17. A conotoxin peptide of embodiment 16, wherein each of the cysteine residues is replaced with an (R)- or (S)-version of a naturally occurring amino acid selected from aspartic acid, glutamic acid or lysine.

Embodiment 18. A conotoxin peptide of embodiment 16, wherein a first of the two cysteine residues is replaced with an unnatural amino acid containing carboxylic acid in a side chain and a second of the two cysteine residues is replaced with an unnatural amino acid containing an amine group in a side chain.

Embodiment 19. A conotoxin peptide of embodiment 16, wherein each of the cysteine residues is replaced with (S)-propargyl glycine or (S)-azidonorvaline.

Embodiment 20. A conotoxin peptide of any of embodiments 16-19, wherein the bridge is a lactam bridge or a triazole bridge.

Embodiment 21. A conotoxin peptide of any of embodiments 1-14, wherein a linker is introduced so as to generate an N-terminus to C-terminus cyclized peptide.

Embodiment 22. A conotoxin peptide of embodiment 21, wherein the linker consists of a sequence of 1 to 100 amino acids.

Embodiment 23. A conotoxin peptide of embodiment 21, wherein the linker is non-peptidic.

Embodiment 24. A conotoxin peptide of any of embodiments 1-14, wherein the peptide is linked to polyethylene glycol polymers.

Embodiment 25. A conotoxin peptide of any of embodiments 1-14, wherein the peptide is expressed as a fusion to a protein.

Embodiment 26. A conotoxin peptide of embodiment 25, wherein the protein is the Fc portion of immunoglobulin G (IgG).

Embodiment 27. A pharmaceutical composition comprising the conotoxin peptide of any of embodiments 1-26.

Embodiment 28. A pharmaceutically acceptable salt comprising the conotoxin peptide of any of embodiments 1-26.

Embodiment 29. A method for treating at least one condition associated with the $\alpha9\alpha10$ subtype of the nicotinic acetylcholine receptor (nAChR) in a subject in need thereof comprising administering to the subject a therapeutically effective amount of a conotoxin peptide, a composition comprising the conotoxin peptide, or a pharmaceutically acceptable salt comprising the conotoxin peptide, wherein the conotoxin peptide is the conotoxin peptide of any of embodiments 1-26, thereby treating the condition.

Embodiment 30. A method of embodiment 29, wherein at least one condition is pain.

Embodiment 31. A method of embodiment 30, wherein the pain is general pain, chronic pain, neuropathic pain, nociceptive pain, inflammatory pain, pain induced by peripheral nerve damage, pain induced by an inflammatory disorder, pain induced by a metabolic disorder, pain induced by cancer, pain induced by chemotherapy, pain induced by a surgical procedure, and/or pain induced by a burn.

Embodiment 32. A method of embodiment 31, wherein the pain is cancer-related chronic pain and/or cancer-related neuropathy.

Embodiment 33. A method of embodiment 29, wherein the at least one condition is an inflammatory condition.

Embodiment 34. A method of embodiment 33, wherein the inflammatory condition is inflammation, chronic inflammation, a rheumatic disease, sepsis, fibromyalgia, inflammatory bowel disease, sarcoidosis, endometriosis, uterine fibroids, an inflammatory skin disease, an inflammatory condition of the lungs, a disease associated with inflammation of the nervous system, periodontal disease, or cardiovascular disease.

Embodiment 35. A method of any of embodiments 33-34, wherein the inflammatory condition is mediated by immune cells.

Embodiment 36. A method of any of embodiments 33-35, wherein the inflammatory condition is long-term inflammation and peripheral neuropathy following injury.

Embodiment 37. A method of embodiment 29, wherein the at least one condition is pain and inflammation.

Embodiment 38. A method of embodiment 29, wherein the at least one condition is inflammation and neuropathy.

Embodiment 39. A conotoxin peptide of any of embodiments 1-14, wherein the peptide bond between the aspartate residue and the proline residue in the Asp-Pro-Arg region is replaced by a non-peptidic bond in which a methylene group is incorporated between the carbonyl of aspartate and the nitrogen of proline.

Embodiment 40. A conotoxin peptide of any of embodiments 1-14, wherein the aspartate in the Asp-Pro-Arg region is replaced by amino malonic acid.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The practice of the present disclosure employs, unless otherwise indicated, conventional techniques of chemistry, molecular biology, microbiology, recombinant DNA, genetics, immunology, cell biology, cell culture, and transgenic biology, which are within the skill of the art. See, e.g., Maniatis et al., Molecular Cloning (Cold Spring Harbor Laboratory Press, Cold Spring Harbor, N.Y., 1982); Sambrook et al., Molecular Cloning, 2nd Ed. (Cold Spring Harbor Laboratory Press, Cold Spring Harbor, N.Y., 1989); Sambrook and Russell, Molecular Cloning, 3rd Ed. (Cold Spring Harbor Laboratory Press, Cold Spring Harbor, N.Y., 2001); Ausubel et al., Current Protocols in Molecular Biology (John Wiley & Sons, updated through 2005); Glover, DNA Cloning (IRL Press, Oxford, 1985); Anand, Techniques for the Analysis of Complex Genomes, (Academic Press, New York, 1992); Guthrie and Fink, Guide to Yeast Genetics and Molecular Biology (Academic Press, New York, 1991); Harlow and Lane, Antibodies, (Cold Spring Harbor Laboratory Press, Cold Spring Harbor, N.Y., 1998); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, (Blackwell Scientific Publications, Oxford, 1988); Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), 4th Ed., (Univ. of Oregon Press, Eugene, Oreg., 2000).

As will be understood by one of ordinary skill in the art, each embodiment disclosed herein can comprise, consist essentially of, or consist of its particular stated element, step, ingredient, or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transitional phrase "consisting essentially of" limits the scope of the embodiment to the specified elements, steps, ingredients, or components and to those that do not materially affect the embodiment.

Unless otherwise indicated, all numbers used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or illustrative language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to publications, patents, and/or patent applications (collectively "references") throughout this specification. Each of the cited references is individually incorporated herein by reference for their particular cited teachings.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A conotoxin peptide of Formula (I):

Formula (I)

Gly Cys X Thr Asp Pro Arg Cys Cit 3-I-Tyr Gln X Tyr,
with a Triazole Bridge and a Disulfide Bridge wherein the triazole bridge is

[triazole bridge structure]

wherein each X represents

[amino acid residue structure with NH and C=O]

and
wherein the C-terminus is a carboxylic acid or an amide group;
or a variant thereof that differs from the conotoxin peptide only in having one conservative amino acid substitution, wherein the variant comprises said triazole bridge, said disulfide bridge, and each said X represented by

[amino acid residue structure with NH and C=O]

or a pharmaceutically acceptable salt of the conotoxin peptide or variant.

2. The variant or pharmaceutically acceptable salt of the variant of claim 1.

3. A PEGylated conotoxin peptide, wherein the PEGylated conotoxin peptide is of Formula (I) covalently attached to one or more polyethylene glycol (PEG) polymers:

Formula (I)

Gly Cys X Thr Asp Pro Arg Cys Cit 3-I-Tyr Gln X Tyr,
with a Triazole Bridge and a Disulfide Bridge wherein the triazole bridge is

[triazole bridge structure]

wherein each X represents

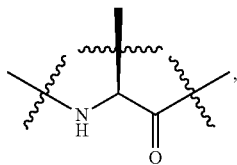 [SMILES: *N[C@@H](C)C(*)=O]

and
wherein the C-terminus is a carboxylic acid or an amide group;
or a PEGylated variant thereof that differs from the PEGylated conotoxin peptide only in having one conservative amino acid substitution, wherein the PEGylated variant comprises said triazole bridge, said disulfide bridge, each said X represented by

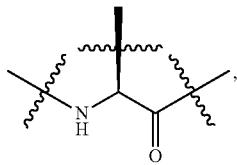 [SMILES: *N[C@@H](C)C(*)=O]

and said one or more covalently attached PEG polymers;
or a pharmaceutically acceptable salt of the PEGylated conotoxin peptide or the PEGylated variant.

4. The PEGylated variant or pharmaceutically acceptable salt of the PEGylated variant of claim 3.

5. A pharmaceutical composition comprising the conotoxin peptide or variant, or pharmaceutically acceptable salt of the conotoxin peptide or variant, of claim 1, and a pharmaceutically acceptable carrier.

6. A pharmaceutical composition comprising the variant or pharmaceutically acceptable salt of the variant of claim 2, and a pharmaceutically acceptable carrier.

7. A pharmaceutical composition comprising the PEGylated conotoxin peptide or PEGylated variant, or pharmaceutically acceptable salt of the PEGylated conotoxin peptide or PEGylated variant, of claim 3, and a pharmaceutically acceptable carrier.

8. A pharmaceutical composition comprising the PEGylated variant or pharmaceutically acceptable salt of the PEGylated variant of claim 4, and a pharmaceutically acceptable carrier.

9. A method of treating pain, an inflammatory condition, pain and inflammation, or inflammation and neuropathy comprising administering to a subject in need thereof a therapeutically effective amount of the conotoxin peptide or variant, or pharmaceutically acceptable salt of the conotoxin peptide or variant, of claim 1.

10. The method of claim 9, which is a method of treating pain, or pain and inflammation, wherein the pain is general pain, chronic pain, neuropathic pain, nociceptive pain, inflammatory pain, pain induced by peripheral nerve damage, pain induced by an inflammatory disorder, pain induced by a metabolic disorder, pain induced by cancer, pain induced by chemotherapy, pain induced by a surgical procedure, and/or pain induced by a burn.

11. The method of claim 9, which is a method of treating an inflammatory condition, wherein the inflammatory condition is inflammation, chronic inflammation, a rheumatic disease, sepsis, fibromyalgia, inflammatory bowel disease, sarcoidosis, endometriosis, uterine fibroids, an inflammatory skin disease, an inflammatory condition of the lungs, a disease associated with inflammation of the nervous system, periodontal disease, or cardiovascular disease.

12. A method of treating pain, an inflammatory condition, pain and inflammation, or inflammation and neuropathy comprising administering to a subject in need thereof a therapeutically effective amount of the variant or pharmaceutically acceptable salt of the variant of claim 2.

13. The method of claim 12, which is a method of treating pain, or pain and inflammation, wherein the pain is general pain, chronic pain, neuropathic pain, nociceptive pain, inflammatory pain, pain induced by peripheral nerve damage, pain induced by an inflammatory disorder, pain induced by a metabolic disorder, pain induced by cancer, pain induced by chemotherapy, pain induced by a surgical procedure, and/or pain induced by a burn.

14. The method of claim 12, which is a method of treating an inflammatory condition, wherein the inflammatory condition is inflammation, chronic inflammation, a rheumatic disease, sepsis, fibromyalgia, inflammatory bowel disease, sarcoidosis, endometriosis, uterine fibroids, an inflammatory skin disease, an inflammatory condition of the lungs, a disease associated with inflammation of the nervous system, periodontal disease, or cardiovascular disease.

15. A method of treating pain, an inflammatory condition, pain and inflammation, or inflammation and neuropathy comprising administering to a subject in need thereof a therapeutically effective amount of the PEGylated conotoxin peptide or PEGylated variant, or pharmaceutically acceptable salt of the PEGylated conotoxin peptide or PEGylated variant, of claim 3.

16. The method of claim 15, which is a method of treating pain, or pain and inflammation, wherein the pain is general pain, chronic pain, neuropathic pain, nociceptive pain, inflammatory pain, pain induced by peripheral nerve damage, pain induced by an inflammatory disorder, pain induced by a metabolic disorder, pain induced by cancer, pain induced by chemotherapy, pain induced by a surgical procedure, and/or pain induced by a burn.

17. The method of claim 15, which is a method of treating an inflammatory condition, wherein the inflammatory condition is inflammation, chronic inflammation, a rheumatic disease, sepsis, fibromyalgia, inflammatory bowel disease, sarcoidosis, endometriosis, uterine fibroids, an inflammatory skin disease, an inflammatory condition of the lungs, a disease associated with inflammation of the nervous system, periodontal disease, or cardiovascular disease.

18. A method of treating pain, an inflammatory condition, pain and inflammation, or inflammation and neuropathy comprising administering to a subject in need thereof a therapeutically effective amount of the PEGylated variant or pharmaceutically acceptable salt of the PEGylated variant of claim 4.

19. The method of claim 18, which is a method of treating pain, or pain and inflammation, wherein the pain is general pain, chronic pain, neuropathic pain, nociceptive pain, inflammatory pain, pain induced by peripheral nerve damage, pain induced by an inflammatory disorder, pain induced by a metabolic disorder, pain induced by cancer, pain induced by chemotherapy, pain induced by a surgical procedure, and/or pain induced by a burn.

20. The method of claim 18, which is a method of treating an inflammatory condition, wherein the inflammatory condition is inflammation, chronic inflammation, a rheumatic disease, sepsis, fibromyalgia, inflammatory bowel disease, sarcoidosis, endometriosis, uterine fibroids, an inflammatory skin disease, an inflammatory condition of the lungs, a disease associated with inflammation of the nervous system, periodontal disease, or cardiovascular disease.

* * * * *